United States Patent
Cook et al.

(10) Patent No.: US 9,745,267 B2
(45) Date of Patent: Aug. 29, 2017

(54) COMPOUNDS AS MODULATORS OF RORC

(71) Applicants: Brian Nicholas Cook, Danbury, CT (US); John D. Huber, Trumbull, CT (US); Robert Owen Hughes, Newtown, CT (US); Thomas Martin Kirrane, Jr., Danbury, CT (US); Celina Lasota, White Plains, NY (US); Xiang Li, New Milford, CT (US); Shuang Liang, Roseville, MN (US); Ingo Andreas Mugge, New Haven, CT (US); Qiang Zhang, Ridgefield, CT (US)

(72) Inventors: Brian Nicholas Cook, Danbury, CT (US); John D. Huber, Trumbull, CT (US); Robert Owen Hughes, Newtown, CT (US); Thomas Martin Kirrane, Jr., Danbury, CT (US); Celina Lasota, White Plains, NY (US); Xiang Li, New Milford, CT (US); Shuang Liang, Roseville, MN (US); Ingo Andreas Mugge, New Haven, CT (US); Qiang Zhang, Ridgefield, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 14/916,576

(22) PCT Filed: Sep. 4, 2014

(86) PCT No.: PCT/US2014/054070
§ 371 (c)(1),
(2) Date: Mar. 4, 2016

(87) PCT Pub. No.: WO2015/035032
PCT Pub. Date: Mar. 12, 2015

(65) Prior Publication Data
US 2016/0251310 A1 Sep. 1, 2016

Related U.S. Application Data

(60) Provisional application No. 61/874,005, filed on Sep. 5, 2013.

(51) Int. Cl.
| | |
|---|---|
| *C07D 401/02* | (2006.01) |
| *C07D 209/96* | (2006.01) |
| *C07D 401/04* | (2006.01) |
| *C07D 401/10* | (2006.01) |
| *C07D 403/04* | (2006.01) |
| *C07D 413/10* | (2006.01) |
| *C07D 417/10* | (2006.01) |
| *C07D 209/10* | (2006.01) |
| *C07D 209/08* | (2006.01) |
| *C07D 401/14* | (2006.01) |
| *C07D 403/10* | (2006.01) |

(52) U.S. Cl.
CPC ......... *C07D 209/96* (2013.01); *C07D 209/08* (2013.01); *C07D 209/10* (2013.01); *C07D 401/02* (2013.01); *C07D 401/04* (2013.01); *C07D 401/10* (2013.01); *C07D 401/14* (2013.01); *C07D 403/04* (2013.01); *C07D 403/10* (2013.01); *C07D 413/10* (2013.01); *C07D 417/10* (2013.01)

(58) Field of Classification Search
CPC .. C07D 401/02; C07D 401/04; C07D 401/10; C07D 401/14
See application file for complete search history.

(56) References Cited

FOREIGN PATENT DOCUMENTS

| | | |
|---|---|---|
| WO | 2011014775 | 2/2011 |
| WO | 2012106995 | 8/2012 |
| WO | 2013019653 | 2/2013 |

OTHER PUBLICATIONS

International Search Report for PCT/US2010/043907, PCT/ISA/210, mailed Nov. 29, 2010.

*Primary Examiner* — Craig Ricci
*Assistant Examiner* — Christopher R Stone
(74) *Attorney, Agent, or Firm* — Paula K. Witmayer; Usha R. Patel

(57) ABSTRACT

The present invention encompasses compounds of the formula (I): wherein the variables are defined herein which are suitable for the modulation of RORC and the treatment of diseases related to the modulation of RORC. The present invention also encompasses processes of making compounds of formula (I) and pharmaceutical preparations containing them.

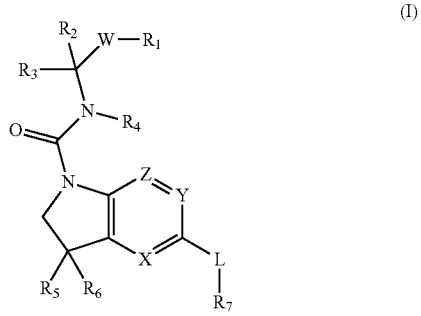

12 Claims, No Drawings

COMPOUNDS AS MODULATORS OF RORC

BACKGROUND OF THE INVENTION

1. Technical Field

The present invention relates to novel compounds which modulate the activity of RORC and their use as medicaments.

2. Background Information

RORγt (retinoid-related orphan receptor γt) (also referred to herein as "RORC") is a transcription factor belonging to the steroid hormone receptor superfamily (reviewed in Jetten 2006. Adv. Dev Biol. 16: 313-355.). RORγt has been identified as a transcriptional factor that is required for the differentiation of T cells and secretion of Interluekin 17 (IL-17) from a subset of T cells termed $Th_{17}$ cells (Ivanov, Cell 2006, 126, 1121-1133). The rationale for the use of a RORγt targeted therapy for the treatment of chronic inflammatory diseases is based on the emerging evidence that $Th_{17}$ cells and the cytokine IL-17 contribute to the initiation and progression of the pathogenesis of several autoimmune diseases including psoriasis, ankylosing spondylitis, rheumatoid arthritis, multiple sclerosis and Crohn's disease (reviewed in Miossec, Nature Drug Discovery 2012, 11, 763-776; see also Khan et al., Bioorganic & Medicinal Chemistry Letters 23 (2013), 532-536). The outcome of recent clinical trials with neutralizing antibodies to IL-17 and its receptor IL-17RA (Leonardi 2012, New England Journal of Medicine, 366, 1190-1199; Papp 2012, New England Journal of Medicine 366, 1181-1189) in psoriasis highlight the role of IL-17 in the pathogenesis of this disease. As such, attenuation of IL-17 secretion from activated Th17 T cells via inhibition of RORγt may offer similar therapeutic benefit.

SUMMARY OF THE INVENTION

The invention comprises a novel class of heteroaromatic compounds and methods for making and using the same. These compounds are useful for the treatment of autoimmune and allergic disorders in that they exhibit good modulatory effect upon RORC.

DETAILED DESCRIPTION OF THE INVENTION

In the first embodiment of the invention there is provided a compound of the following formula (I):

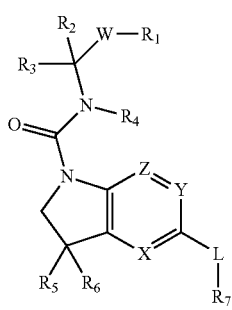

(I)

$R_1$ is: —CN, —S(O)$_m$C$_{1-6}$alkyl, —S(O)$_m$C$_{1-6}$cyanoalkyl —S(O)$_m$C$_{1-6}$haloalkyl, —S(O)$_m$C$_{3-6}$cycloalkyl, —S(O)$_m$C$_{1-6}$ hydroxyalkyl, —S(O)$_m$C$_{1-6}$alkyloxy, —SO$_2$NR$_a$R$_b$, —NR$_a$S(O)$_m$C$_{1-6}$alkyl, —NR$_a$S(O)$_m$C$_{3-6}$cycloalkyl, —S(O)(NRc)C$_{1-6}$alkyl —S(O)(NRc)C$_{3-6}$cycloalkyl or —S(O)(NRc) NR$_a$R$_b$, wherein R$_a$ and R$_b$ are each independently H, NR$_a$R$_b$ C$_{1-6}$alkyl, C$_{3-6}$cycloalkyl, C$_{1-6}$haloalkyl, C$_{1-6}$cyanoalkyl, or C$_{1-6}$alkyloxy or; R$_a$ and R$_b$ taken together with the nitrogen to which they are attached form a C$_{2-6}$ heterocyclic ring optionally containing 1-4 additional groups selected from NH, O and S; and m is 0, 1 or 2; and R$_c$ is each independently H, C$_{1-6}$alkyl, C$_{3-6}$cycloalkyl, or C$_{1-6}$alkyloxy; W is: C$_{6-14}$ aryl, a C$_{2-10}$ heteroaryl containing 1-4 groups selected from N, NH, O and S, saturated and partially saturated C$_{2-10}$ heterocyclyl containing 1-4 groups selected from N, NH, O and S, or saturated and partially saturated C$_{3-12}$ cycloalkyl ring, wherein each W is optionally substituted with 0-4 substituents selected from the group consisting of cyano, halo, hydroxy, C$_{1-6}$alkyl, C$_{1-6}$ haloalkyl, C$_{1-6}$ hydroxyalkyl, C$_{1-6}$ alkenyl, C$_{1-6}$ haloalkenyl, C$_{1-6}$ alkynyl, C$_{1-6}$ haloalkynyl, C$_{3-6}$ cycloalkyl, C$_{3-6}$ heterocycle containing 1-4 groups selected from NH, O and S, C$_{1-6}$ alkoxy, C$_{3-6}$ cycloalkyl-oxy, —S(O)$_m$C$_{1-6}$ alkyl, —S(O)$_m$C$_{3-6}$ cycloalkyl, CN, —C(O)—NR$_c$R$_d$, —C(O)—OR$_c$, —NR$_c$R$_d$, NR$_c$R$_d$—C$_{1-6}$alkyl-, and R$_e$O—C$_{1-6}$alkoxy NR$_c$R$_d$—C$_{1-6}$alkoxy-, wherein R$_c$ and R$_d$ is each independently H, C$_{1-6}$ alkyl, C$_{1-6}$ alkenyl, C$_{1-6}$ alkynyl, C$_{3-12}$ cycloalkyl, C$_{6-14}$ aryl, C$_{2-6}$ heterocycle containing 1-4 groups selected from NH, O and S, or a C$_{2-10}$heteroaryl containing 1-4 groups selected from N, NH, O and S, or Rc and R$_d$ taken together with the nitrogen to which they are attached form a C$_{2-6}$ heterocyclic ring optionally containing 1-4 additional groups selected from NH, O and S;
$R_2$ is: —C$_{1-6}$alkyl, —C$_{3-6}$cycloalkyl, —C$_{1-6}$alkyloxy, —C$_{1-6}$ hydroxyalkyl, —C$_{1-6}$haloalkyl, —H, —C(O)OR$_e$, or —C(O)NR$_e$R$_f$, wherein R$_e$ and R$_f$ is each independently H or C$_{1-6}$ alkyl;
$R_3$ is: —C$_{1-6}$alkyl, —C$_{3-6}$cycloalkyl, —C$_{1-6}$alkyloxy; —H, —C(O)OR$_e$, or C(O)NR$_e$R$_f$, wherein R$_e$ and R$_f$ is each independently H or C$_{1-6}$ alkyl; or $R_2$ and $R_3$ taken together with the carbon to which they are attached form a C$_{3-12}$ carbocyclic ring or a C$_{2-10}$ heterocyclic containing 1-4 groups selected from NH, O and S; $R_4$ is: —H, —C$_{1-6}$alkyl, —C$_{1-6}$alkyloxy, or —C$_{3-6}$cycloalkyl;
X, Y and Z are chosen independently from CR$_e$ and R$_e$ is: —H, -halo, —C$_{1-6}$alkyl, —C$_{1-6}$ haloalkyl, —C$_{1-6}$ haloalkenyl, —C$_{1-6}$ haloalkynyl, —C$_{3-6}$ cycloalkyl, —C$_{1-6}$ alkoxy, —C$_{3-6}$ cycloalkyloxy, —OC$_{1-6}$alkyl, —OC$_{3-6}$ cycloalkyl, —S(O)$_m$C$_{1-6}$ alkyl, —S(O)$_m$C$_{3-6}$ cycloalkyl, CN, —C(O)—NR$_f$R$_g$, —C(O)—OR$_f$, or —NR$_f$R$_g$, wherein R$_f$ and R$_g$ is each independently H or —C$_{1-6}$ alkyl; C$_{1-6}$ alkenyl, C$_{1-6}$ alkynyl, C$_{3-12}$ cycloalkyl, C$_{6-14}$ aryl, C$_{3-6}$ heterocycle containing 1-4 groups selected from N, NH, O and S, or a C$_{2-10}$ heteroaryl containing 1-4 groups selected from N, NH, O and S;
$R_5$ is: —H-halo, —C$_{1-6}$ alkyl, C$_{1-6}$ alkenyl, —C$_{1-6}$ alkoxy, —S(O)$_m$C$_{1-6}$alkyl, —C$_{6-14}$ aryl, —C$_{2-10}$ heterocyclyl containing 1-4 groups selected from N, NH, O and S, —C$_{2-10}$ heteroaryl containing 1-4 groups selected from N, NH, O and S, —CN, —C$_3$-C$_6$cycloalkyl, or —C$_{1-6}$haloalkyl, wherein R$_5$ may be optionally substituted with 0-5 halo, C$_{1-6}$ alkyl, C$_{1-6}$ alkoxy, —S(O)$_m$C$_{1-6}$alkyl, C$_{6-14}$ aryl, C$_{2-10}$ heterocyclyl containing 1-4 groups selected from N, NH, O and S, or a C$_{2-10}$ heteroaryl containing 1-4 groups selected from N, NH, O and S, CN, C$_3$-C$_6$cycloalkyl, OH or —C(O)—NR$_a$R$_b$, $R_6$ is: -halo, —C$_{1-6}$ alkyl, C$_{1-6}$ alkenyl, —C$_{1-6}$ alkoxy, —S(O)$_m$C$_{1-6}$alkyl, —C$_{6-14}$ aryl, —C$_{2-10}$ heterocyclyl containing 1-4 groups selected from N, NH, O and S, —C$_{2-10}$ heteroaryl containing 1-4 groups selected from N, NH, O and S, —H, —CN, —C$_3$-C$_6$cycloalkyl, or —$C_{1-6}$haloalkyl, wherein $R_6$ may be optionally substituted with 0-5 halo, $C_{1-6}$ alkyl, $C_{1-6}$ alkoxy, —$S(O)_mC_{1-6}$alkyl, $C_{6-14}$ aryl, $C_{2-10}$ heterocyclyl containing 1-4 groups selected from N, NH, O and S, or a $C_{2-10}$ heteroaryl containing 1-4 groups selected from N, NH, O and S, CN, —$C_3$-$C_6$cycloalkyl, OH or —C(O)—$NR_aR_b$, or $R_5$ and $R_6$ taken together with the carbon to which they attached form a $C_{3-12}$ carbocyclic ring or a $C_{2-10}$ heterocyclic containing 1-4 groups selected from N, NH, O and S; L is: a direct bond, —C=C—

—$S(O)_m$—, —$NR_aS(O)_m$, —$S(O)_mNR_a$— —O—, —C(O)—, —$(CH_2)_n$—, —O—$(CH_2)_n$—, —$N(R_a)$—, —$N(R_a)$—$(CH_2)_n$—, —$(CH_2)_n$—$N(R_a)$—, —C(O)—N(Ra)—, —C(O)—$N(R_a)$—$(CH_2)_n$— or —$N(R_a)$—C(O)—$N(R_b)$—; wherein $R_a$ and $R_b$ is each independently H or $C_{1-3}$ alkyl;

$R_7$ is: halo, cycloalkyl, cycloalkenyl,

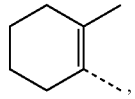

—$C_{6-14}$ aryl, —$C_{2-10}$ heterocyclyl containing 1-4 groups selected from N, NH, O and S, —$C_{2-10}$ heteroaryl containing 1-4 groups selected from N, NH, O and S, wherein $R_7$ may be optionally substituted with 0-5 substituents selected from the group consisting of halogen, hydroxy, $C_{1-6}$alkyl, $C_{1-6}$ haloalkyl, $C_{1-6}$ hydroxyalkyl, $C_{1-6}$ haloalkenyl, $C_{1-6}$ haloalkynyl, $C_{3-6}$ cycloalkyl, $C_{3-7}$ heterocycle containing 1-4 groups selected from N, NH, O and S, $C_{6-14}$ aryl, $C_{2-10}$ heteroaryl containing 1-4 groups selected from N, NH, O and S, $C_{1-6}$ alkoxy, $C_{1-6}$ haloalkoxy, $C_{3-6}$ cycloalkyloxy, —$S(O)_mC_{1-6}$ alkyl, —$S(O)_mC_{3-6}$ cycloalkyl, CN, —C(O)—$NR_cR_d$, —C(O)—$OR_c$, $NR_cR_d$ and $NR_cR_dC_{1-6}$alkyl-, wherein $R_c$ and $R_d$ is each independently H, $C_{1-6}$ alkyl, $C_{1-6}$ alkenyl, $C_{1-6}$ alkynyl, cycloalkyl, —$C_{6-14}$ aryl, $C_{2-10}$ heterocyclyl containing 1-4 groups selected from N, NH, O and S, or a $C_{2-10}$ heteroaryl containing 1-4 groups selected from N, NH, O and S, wherein each heterocyclyl, aryl or heteroaryl is optionally substituted by $C_{1-6}$ alkyl, $C_{1-6}$ alkoxy; or Rc and Rd—together with the nitrogen to which they are attached form a $C_{2-6}$ heterocyclic ring optionally containing 1-4 additional groups selected from N, NH, O and S; each n is independently 1-4; each m is independently 0-2; or a pharmaceutically acceptable salt thereof.

Additional subgeneric embodiments for $R_1$, $R_2$, $R_3$, $R_4$, $R_5$, $R_6$, $R_7$, W, X, Y, Z and L in formula (I) set forth above are as described below:

The compound according to the first embodiment described above and wherein:

$R_1$ is: —$S(O)_mC_{1-6}$alkyl, —$S(O)_mC_{1-6}$haloalkyl, —$S(O)_m$$C_{3-6}$cycloalkyl, —$SO_2NR_aR_b$ wherein $R_a$ and $R_b$ are each independently H, $C_{3-6}$cycloalkyl, or $C_{1-6}$alkyloxy, or $R_a$ and $R_b$ taken together with the nitrogen to which they are attached form a —$C_{2-6}$ heterocyclic ring optionally containing 1-4 additional groups selected from NH, O and S; —$S(O)(NRc)C_{1-6}$alkyl, —$S(O)(NRc)C_{3-6}$cycloalkyl, wherein $R_c$ is each independently H, $C_{1-6}$alkyl, $C_{3-6}$cycloalkyl, or $C_{1-6}$alkyloxy or —CN; and each m is independently 0-2; or a pharmaceutically acceptable salt thereof.

The compound according to the first embodiment described above and wherein:

$R_1$ is: —$S(O)_2C_{1-6}$alkyl, or —$SO_2NR_aR_b$ wherein $R_a$ and $R_b$ are independently H and $C_{1-6}$alkyl; or a pharmaceutically acceptable salt thereof.

The compound according to the first embodiment described above and wherein:

$R_1$ is: —$S(O)_2C_{1-3}$alkyl or —$SO_2NR_aR_b$ wherein $R_a$ and $R_b$ are independently chosen from H and $C_{1-3}$alkyl; or a pharmaceutically acceptable salt thereof.

The compound according to the first embodiment described above and wherein:

W is: $C_{6-14}$ aryl, $C_{2-10}$ heteroaryl containing 1-4 groups selected from N, NH, O and S, or bicyclo [1.1.1] pentane wherein each W is optionally substituted with 0-4 substituents selected from the group consisting of halo, hydroxy, $C_{1-6}$alkyl, $C_{1-6}$ haloalkyl, $C_{1-6}$ haloalkenyl, $C_{1-6}$ haloalkynyl, $C_{3-6}$ cycloalkyl, $C_{1-6}$ alkoxy, $C_{3-6}$ cycloalkyloxy, —$S(O)_mC_{1-6}$ alkyl, —$S(O)_mC_{3-6}$ cycloalkyl, CN, —C(O)—$NR_cR_d$, —C(O)—$OR_c$, and $NR_cR_d$ wherein $R_c$ and $R_d$ is each independently H, $C_{1-6}$ alkyl, $C_{1-6}$ alkenyl, $C_{1-6}$ alkynyl, cycloalkyl, —$C_{6-14}$ aryl, $C_{2-10}$ heterocycyl containing 1-4 groups selected from NH, O and S, or a $C_{2-10}$ heteroaryl containing 1-4 groups selected from N, NH, O and S; or a pharmaceutically acceptable salt thereof.

The compound according to the first embodiment described above and wherein: W is: phenyl, or monocyclic $C_{3-5}$ heteroaryl containing 1-2 nitrogens as the only heteroatoms in the ring, wherein each W is optionally substituted with 0-4 substituents selected from the group consisting of halo, $C_{1-6}$alkyl, $C_{1-6}$ haloalkyl, $C_{1-6}$ haloalkenyl, $C_{1-6}$ haloalkynyl, $C_{3-6}$ cycloalkyl, $C_{1-6}$ alkoxy, $C_{3-6}$ cycloalkyloxy, —$S(O)_mC_{1-6}$ alkyl, —$S(O)_mC_{3-6}$ cycloalkyl, —CN, —C(O)—$NR_cR_d$, —C(O)—$OR_c$, and $NR_cR_d$, wherein $R_c$ and $R_d$ is each independently H, $C_{1-6}$ alkyl, $C_{1-6}$ alkenyl, $C_{1-6}$ alkynyl, or cycloalkyl; or a pharmaceutically acceptable salt thereof.

The compound according to the first embodiment described above and wherein:

W is: phenyl, or $C_{4-5}$ monocyclic heteroaryl containing 1-2 nitrogens as the only heteroatoms in the ring, wherein each W is optionally substituted with 0-4 substituents selected from the group consisting of halo, $C_{1-6}$alkyl, $C_{1-6}$ haloalkyl, $C_{1-6}$ haloalkenyl, $C_{1-6}$ haloalkynyl, $C_{3-6}$ cycloalkyl, $C_{1-6}$ alkoxy, $C_{3-6}$ cycloalkyloxy, —$S(O)_mC_{1-6}$ alkyl, —$S(O)_m$$C_{3-6}$ cycloalkyl, —CN, —C(O)—$NR_cR_d$, —C(O)—$OR_c$, and $NR_cR_d$, wherein $R_c$ and $R_d$ is H, $C_{1-6}$ alkyl, $C_{1-6}$ alkenyl, $C_{1-6}$ alkynyl, or cycloalkyl; or a pharmaceutically acceptable salt thereof.

The compound according to the first embodiment described above and wherein:

$R_2$ is: H, or $C_{1-6}$alkyl; and $R_3$ is: H, or $C_{1-6}$alkyl; or R2 and R3 taken together form a cyclopropane ring or a pharmaceutically acceptable salt thereof.

The compound according to the first embodiment described above and wherein:

$R_2$ and $R_3$ are H; or a pharmaceutically acceptable salt thereof.

The compound according to the first embodiment described above and wherein:

$R_4$ is: H, or $C_{1-6}$alkyl; or a pharmaceutically acceptable salt thereof.

The compound according to the first embodiment described above and wherein:

$R_4$ is H; or a pharmaceutically acceptable salt thereof.

The compound according to the first embodiment described above and wherein:

$R_5$ is: H; $C_{1-6}$ alkyl, or $C_3$-$C_6$cycloalkyl; wherein $R_5$ may be optionally substituted with 0-5 halo, $C_{1-6}$ alkyl, $C_{1-6}$ alkoxy, —S(O)$_m$C$_{1-6}$alkyl, —S(O)$_m$C$_{1-6}$alkyl, —C$_{6-14}$ aryl, $C_{2-10}$ heterocycyl containing 1-4 groups selected from NH, O and S, $C_{2-10}$ heteroaryl containing 1-4 groups selected from N, NH, O and S; CN, or $C_3$-$C_6$cycloalkyl; $R_6$ is: H; $C_{1-6}$ alkyl, or $C_3$-$C_6$cycloalkyl;

wherein $R_6$ may be optionally substituted optionally substituted with 0-5 substituents selected from the group consisting of halogen, $C_{1-6}$ haloalkyl, $C_{1-6}$ haloalkenyl, $C_{1-6}$ haloalkynyl, $C_{3-6}$ cycloalkyl, $C_{1-6}$ alkoxy, $C_{3-6}$ cycloalkyloxy, —S(O)$_m$C$_{1-6}$ alkyl, —S(O)$_m$C$_{3-6}$ cycloalkyl, —CN, —C(O)—NR$_c$R$_d$, —C(O)—OR$_c$, and NR$_c$R$_d$ wherein R$_c$ and R$_d$ is H, $C_{1-6}$ alkyl. $C_{1-6}$ alkenyl, $C_{1-6}$ alkynyl, cycloalkyl, —C$_{6-14}$ aryl, $C_{2-10}$ heterocycyl containing 1-4 groups selected from NH, O and S, $C_{2-10}$ heteroaryl containing 1-4 groups selected from N, NH, O and S; or $R_5$ and $R_6$ taken together with the carbon to which they attached form a $C_{3-12}$ carbocyclic ring or a $C_{2-10}$ heterocyclic ring containing 1-4 groups selected from NH, O and S; or a pharmaceutically acceptable salt thereof.

The compound according to the first embodiment described above and wherein: $R_5$ is: H; or $C_{1-3}$ alkyl; $R_6$ is: H; or $C_{1-3}$ alkyl; or $R_5$ and $R_6$ taken together with the carbon to which they attached may form a $C_{5-6}$ carbocyclic ring; or a pharmaceutically acceptable salt thereof.

The compound according to the first embodiment described above and wherein: $R_5$ and $R_6$ are each independently —$C_{1-3}$ alkyl; or $R_5$ and $R_6$ taken together with the carbon to which they attached may form a $C_{3-6}$ carbocyclic ring or a $C_{2-5}$ heterocyclic ring containing 1-4 groups selected from NH, O and S; or a pharmaceutically acceptable salt thereof.

The compound according to the first embodiment described above and wherein:
L is: a bond, —O— or —O—(CH$_2$)$_n$—; or a pharmaceutically acceptable salt thereof.

The compound according to the first embodiment described above and wherein:
L is a bond; or a pharmaceutically acceptable salt thereof.

The compound according to the first embodiment described above and wherein:
$R_7$ is: halo, $C_{6-14}$ aryl or $C_{2-10}$ heteroaryl containing 1-4 groups selected from N, NH, O and S; wherein $R_7$ may be optionally substituted with 0-5 substituents selected from the group consisting of halogen, hydroxy, $C_{1-6}$ alkyl, $C_{1-6}$ haloalkyl, $C_{1-6}$ hydroxyalkyl, $C_{1-6}$ haloalkenyl, $C_{1-6}$ haloalkynyl, $C_{3-6}$ cycloalkyl, $C_{1-6}$ alkoxy, $C_{1-6}$ haloalkoxy, $C_{3-6}$ cycloalkyloxy, —S(O)$_m$C$_{1-6}$ alkyl, —S(O)$_m$C$_{3-6}$ cycloalkyl, —CN, —C(O)—NR$_c$R$_d$, —C(O)—OR$_c$, and NR$_c$R$_d$, wherein R$_c$ and R$_d$ is H, $C_{1-6}$ alkyl, $C_{1-6}$ alkenyl, $C_{1-6}$ alkynyl, $C_{3-12}$ cycloalkyl, $C_{6-14}$ aryl, $C_{2-6}$ heterocycyl containing 1-4 groups selected from NH, O and S, or a $C_{2-10}$ heteroaryl containing 1-4 groups selected from N, NH, O and S;
each m is independently 0-2; or a pharmaceutically acceptable salt thereof.

The compound according to the first embodiment described above and wherein:
$R_7$ is: phenyl, bi-phenyl, naphthyl, $C_{4-5}$ monocyclic heteroaryl, $C_{8-9}$ fused heteroaryl or $C_{10-11}$ bi-heteroaryl wherein said heteroaryls contain 1-2 nitrogens as the only heteroatoms in the ring; wherein $R_7$ may be optionally substituted optionally substituted with 0-5 substituents selected from the group consisting of halogen, hydroxy, $C_{1-6}$alkyl, $C_{1-6}$ haloalkyl, $C_{1-6}$ hydroxyalkyl, $C_{1-6}$ haloalkenyl, $C_{1-6}$ haloalkynyl, $C_{3-6}$ cycloalkyl, $C_{1-6}$ alkoxy, $C_{3-6}$ cycloalkyloxy, —S(O)$_m$C$_{1-6}$ alkyl, —S(O)$_m$C$_{3-6}$ cycloalkyl, —CN, —C(O)—NR$_c$R$_d$, —C(O)—OR$_c$, and NR$_c$R$_d$ wherein R$_c$ and R$_d$ is each independently H, $C_{1-6}$ alkyl, $C_{1-6}$ alkenyl, $C_{1-6}$ alkynyl or cycloalkyl;
each m is independently 0-2; or a pharmaceutically acceptable salt thereof.

The compound according to the first embodiment described above and wherein:
$R_7$ is: phenyl, or a $C_{4-5}$ monocyclic heteroaryl containing 1-2 nitrogens as the only heteroatoms in the ring; wherein $R_7$ may be optionally substituted with 0-5 substituents selected from the group consisting of halogen, hydroxy, $C_{1-6}$alkyl, $C_{1-6}$ haloalkyl, $C_{1-6}$ haloalkenyl, $C_{1-6}$ haloalkynyl, $C_{3-6}$ cycloalkyl, $C_{1-6}$ alkoxy, $C_{3-6}$ cycloalkyloxy, —S(O)$_m$C$_{1-6}$ alkyl, —S(O)$_m$C$_{3-6}$ cycloalkyl, —CN, —C(O)—NR$_c$R$_d$, —C(O)—OR$_c$, and NR$_c$R$_d$, wherein each R$_c$ and R$_d$ is independently H, $C_{1-6}$ alkyl, $C_{1-6}$ alkenyl, $C_{1-6}$ alkynyl or $C_{3-12}$ cycloalkyl; each m is independently 0-2; or a pharmaceutically acceptable salt thereof.

The compound according to the first embodiment described above and wherein:
$R_1$ is: —S(O)$_m$C$_{1-6}$alkyl, —S(O)$_m$C$_{3-6}$cycloalkyl, —SO$_2$NR$_a$R$_b$ wherein R$_a$ and R$_b$ are each independently H, $C_{1-6}$alkyl, $C_{3-6}$cycloalkyl, or $C_{1-6}$alkyloxy, or R$_a$ and R$_b$ taken together with the nitrogen to which they are attached form a $C_{2-6}$ heterocyclic ring optionally containing 1-4 additional groups selected from NH, O and S; or —CN; W is:
$C_{6-14}$ aryl or a $C_{2-10}$ heteroaryl containing 1-4 groups selected from N, NH, O and S, wherein each W is optionally substituted with 0-4 substituents selected from the group consisting of halo, hydroxy, $C_{1-6}$alkyl, $C_{1-6}$ haloalkyl, $C_{1-6}$ haloalkenyl, $C_{1-6}$ haloalkynyl, $C_{3-6}$ cycloalkyl, $C_{1-6}$ alkoxy, $C_{3-6}$ cycloalkyloxy, —S(O)$_m$C$_{1-6}$ alkyl, —S(O)$_m$C$_{3-6}$ cycloalkyl, CN, —C(O)—NR$_c$R$_d$, —C(O)—OR$_c$, and NR$_c$R$_d$ wherein R$_c$ and R$_d$ is each independently H, $C_{1-6}$ alkyl, $C_{1-6}$ alkenyl, $C_{1-6}$ alkynyl, $C_{3-12}$ cycloalkyl, $C_{6-14}$ aryl, $C_{2-6}$ heterocycyl containing 1-4 groups selected from NH, O and S, or a $C_{2-10}$ heteroaryl containing 1-4 groups selected from N, NH, O and S; $R_2$ is: H, or $C_{1-6}$alkyl; $R_3$ is: H, or $C_{1-6}$alkyl; $R_4$ is: H, or $C_{1-6}$alkyl;
X is CR$_e$; and R$_e$ is: H, halo, $C_{1-6}$alkyl, $C_{1-6}$ haloalkyl, $C_{1-6}$ haloalkenyl, $C_{1-6}$haloalkynyl, $C_{3-6}$ cycloalkyl, $C_{1-6}$ alkoxy, $C_{3-6}$ cycloalkyloxy, —S(O)$_m$C$_{1-6}$ alkyl, —S(O)$_m$C$_{3-6}$ cycloalkyl, —CN, —C(O)—NR$_f$R$_g$, —C(O)—OR$_f$, or —NR$_f$R$_g$, wherein R$_f$ and R$_g$ is H or $C_{1-6}$ alkyl, —$C_{1-6}$ alkenyl, —$C_{1-6}$ alkynyl, or —$C_{3-12}$ cycloalkyl;
$R_5$ is: H; $C_{1-6}$ alkyl, or $C_3$-$C_6$cycloalkyl; wherein $R_5$ may be optionally substituted with 0-5 halo, $C_{1-6}$ alkyl, $C_{1-6}$ alkoxy, —S(O)$_m$C$_{1-6}$alkyl, —S(O)$_m$C$_{1-6}$alkyl, —C$_{6-14}$ aryl, $C_{2-10}$ heterocycyl containing 1-4 groups selected from NH, O and S, $C_{2-10}$ heteroaryl containing 1-4 groups selected from N, NH, O and S, CN, or $C_3$-$C_6$cycloalkyl; $R_6$ is: H; $C_{1-6}$ alkyl, or $C_3$-$C_6$cycloalkyl; wherein $R_6$ may be optionally substituted optionally substituted with 0-5 substituents selected from the group consisting of halogen, $C_{1-6}$ haloalkyl, $C_{1-6}$ haloalkenyl, $C_{1-6}$ haloalkynyl, $C_{3-6}$ cycloalkyl, $C_{1-6}$ alkoxy, $C_{3-6}$ cycloalkyloxy, —S(O)$_m$C$_{1-6}$ alkyl, —S(O)$_m$C$_{3-6}$ cycloalkyl, —CN, —C(O)—NR$_c$R$_d$, —C(O)—OR$_c$, and NR$_c$R$_d$ wherein R$_c$ and R$_d$ is H, $C_{1-6}$ alkyl, $C_{1-6}$ alkenyl, $C_{1-6}$ alkynyl, $C_{3-12}$ cycloalkyl, $C_{6-14}$ aryl, $C_{2-6}$ heterocycyl containing 1-4 groups selected from NH, O and S, or a $C_{2-10}$ heteroaryl containing 1-4 groups selected from N, NH, O and S; or $R_5$ and $R_6$ taken together with the carbon to which they attached form a $C_{3-12}$ carbocyclic ring; L is: a bond, —O— or —O—(CH$_2$)$^n$; R$_7$ is: halo, C$_{6-14}$ aryl or C$_{2-10}$ heteroaryl containing 1-4 groups selected from N, NH, O and S;

wherein R$_7$ may be optionally substituted with 0-5 substituents selected from the group consisting of halogen, hydroxy, C$_{1-6}$ alkyl, C$_{1-6}$ haloalkyl, C$_{1-6}$ hydroxyalkyl, C$_{1-6}$ haloalkenyl, C$_{1-6}$ haloalkynyl, C$_{3-6}$ cycloalkyl, C$_{1-6}$ alkoxy, C$_{1-6}$ haloalkoxy, C$_{3-6}$ cycloalkyloxy, —S(O)$_m$C$_{1-6}$ alkyl, —S(O)$_m$C$_{3-6}$ cycloalkyl, —CN, —C(O)—NR$_c$R$_d$, —C(O)—OR$_c$, and NR$_c$R$_d$, wherein R$_c$ and R$_d$ is H, C$_{1-6}$ alkyl, C$_{1-6}$ alkenyl, C$_{1-6}$ alkynyl, C$_{3-12}$ cycloalkyl, C$_{6-14}$ aryl, C$_{2-6}$ heterocycyl containing 1-4 groups selected from NH, O and S, or a C$_{2-10}$ heteroaryl containing 1-4 groups selected from N, NH, O and S;

each m is independently 0-2; or a pharmaceutically acceptable salt thereof.

The compound according to the first embodiment described above and wherein: R$_1$ is: —S(O)$_2$C$_{1-3}$alkyl, or —SO$_2$NR$_a$R$_b$ wherein R$_a$ and R$_b$ are independently H and C$_{1-6}$alkyl; W is: phenyl, or C$_{4-5}$ heteroaryl containing 1-2 nitrogens as the only heteroatoms in the ring, wherein each W is optionally substituted with 0-4 substituents selected from the group consisting of halo, C$_{1-6}$alkyl, C$_{1-6}$ haloalkyl, C$_{1-6}$ haloalkenyl, C$_{1-6}$ haloalkynyl, C$_{3-6}$ cycloalkyl, C$_{1-6}$ alkoxy, C$_{3-6}$ cycloalkyloxy, —S(O)$_m$C$_{1-6}$ alkyl, —S(O)$_m$C$_{3-6}$ cycloalkyl, —CN, —C(O)—NR$_c$R$_d$, —C(O)—OR$_c$, and NR$_c$R$_d$, wherein R$_c$ and R$_d$ is each independently H, C$_{1-6}$ alkyl, C$_{1-6}$ alkenyl, C$_{1-6}$ alkynyl, or C$_{3-12}$ cycloalkyl; R$_2$ is: —H, or —C$_{1-3}$alkyl; R$_3$ is: —H, or —C$_{1-3}$alkyl; R$_4$ is: —H, or —C$_{1-3}$alkyl; X is CR$_e$; and R$_e$ is: H, halo, C$_{1-6}$alkyl, or C$_{3-12}$ cycloalkyl; R$_5$ is: H; or C$_{1-3}$ alkyl; R$_6$ is: H; or C$_{1-3}$ alkyl;

or R$_5$ and R$_6$ taken together with the carbon to which they attached form a C$_{5-6}$ carbocyclic ring; L is: a bond; R$_7$ is: phenyl, or C$_{4-5}$ heteroaryl containing 1-2 nitrogens as the only heteroatoms in the ring; wherein R$_7$ may be optionally substituted optionally substituted with 0-5 substituents selected from the group consisting of halogen, hydroxy, C$_{1-6}$alkyl, C$_{1-6}$ haloalkyl, C$_{1-6}$ hydroxyalkyl, C$_{1-6}$ haloalkenyl, C$_{1-6}$ haloalkynyl, C$_{3-6}$ cycloalkyl, C$_{1-6}$ alkoxy, C$_{3-6}$ cycloalkyloxy, —S(O)$_m$C$_{1-6}$ alkyl, —S(O)$_m$C$_{3-6}$ cycloalkyl, —CN, —C(O)—NR$_c$R$_d$, —C(O)—OR$_c$, and NR$_c$R$_d$ wherein R$_c$ and R$_d$ is each independently H, C$_{1-6}$ alkyl, C$_{1-6}$ alkenyl, C$_{1-6}$ alkynyl or C$_{3-12}$ cycloalkyl; each m is independently 0-2; or a pharmaceutically acceptable salt thereof.

The compound according to the first embodiment described above and wherein: R$_1$ is: —S(O)$_2$C$_{1-3}$alkyl, or —SO$_2$NR$_a$R$_b$ wherein R$_a$ and R$_b$ are independently chosen from H and C$_{1-3}$alkyl; W is: phenyl, or C$_{4-5}$ heteroaryl containing 1-2 nitrogens as the only heteroatoms in the ring, wherein each W is optionally substituted with 0-4 substituents selected from the group consisting of halo, C$_{1-6}$alkyl, C$_{1-6}$ haloalkyl, C$_{1-6}$ haloalkenyl, C$_{1-6}$ haloalkynyl, C$_{3-6}$ cycloalkyl, C$_{1-6}$ alkoxy, C$_{3-6}$ cycloalkyloxy, —S(O)$_m$C$_{1-6}$ alkyl, —S(O)$_m$C$_{3-6}$ cycloalkyl, —CN, —C(O)—NR$_c$R$_d$, —C(O)—OR$_c$, and NR$_c$R$_d$, wherein each R$_c$ and R$_d$ is independently H, C$_{1-6}$ alkyl, C$_{1-6}$ alkenyl, C$_{1-6}$ alkynyl, or C$_{3-12}$ cycloalkyl; R$_2$, R$_3$ and R$_4$ are H; X is CR$_e$; and R$_e$ is: —H, or —C$_{1-6}$alkyl; R$_5$ and R$_6$ are each independently —C$_{1-3}$ alkyl; or R$_5$ and R$_6$ taken together with the carbon to which they attached form a C$_5$ carbocyclic ring; L is: a bond; R$_7$ is: phenyl, or a C$_{4-5}$ heteroaryl containing 1-2 nitrogens as the only heteroatoms in the ring; wherein R$_7$ may be optionally substituted with 0-5 substituents selected from the group consisting of halogen, hydroxy, C$_{1-6}$alkyl, C$_{1-6}$ haloalkyl, C$_{1-6}$ haloalkenyl, C$_{1-6}$ haloalkynyl, C$_{3-6}$ cycloalkyl, C$_{1-6}$ alkoxy, C$_{3-6}$ cycloalkyloxy, —S(O)$_m$C$_{1-6}$ alkyl, —S(O)$_m$C$_{3-6}$ cycloalkyl, —CN, —C(O)—NR$_c$R$_d$, —C(O)—OR$_c$, and NR$_c$R$_d$, wherein each R$_c$ and R$_d$ is independently H, C$_{1-6}$ alkyl, C$_{1-6}$ alkenyl, C$_{1-6}$ alkynyl or C$_{3-12}$ cycloalkyl; each m is independently 0-2; or a pharmaceutically acceptable salt thereof.

Additional embodiments include any possible combinations of the above sub-embodiments for R$_1$, R$_2$, R$_3$, R$_4$, R$_5$, R$_6$, R$_7$, W, X, Y, Z and L.

In another embodiment, the invention provides made compounds in Table I which can be made in view of the general schemes, examples and methods as described herein.

TABLE I

| Example | Structure | RT (min) | m/z [M + H]$^+$ | HPLC Method |
|---|---|---|---|---|
| 1 | 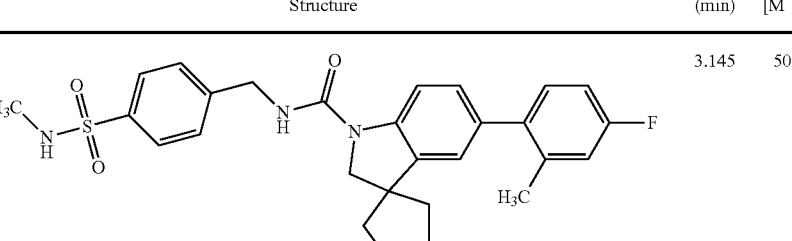 | 3.145 | 508.15 | C |
| 2 | 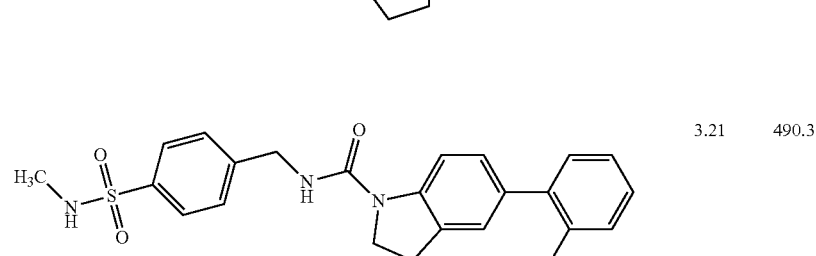 | 3.21 | 490.3 | C |

TABLE I-continued

| Example | Structure | RT (min) | m/z [M + H]+ | HPLC Method |
|---|---|---|---|---|
| 3 | 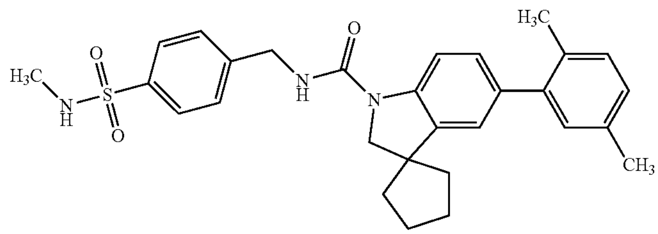 | 3.23 | 504.2 | C |
| 4 | 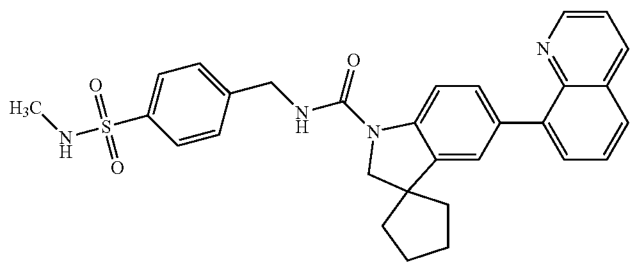 [SMILES: CNS(=O)(=O)c1ccc(CNC(=O)N2CC3(CCCC3)c3cc(-c4cccc5cccnc45)ccc32)cc1] | 2.97 | 527.2 | C |
| 5 | 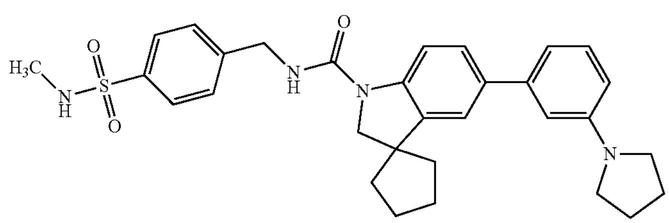 [SMILES: CNS(=O)(=O)c1ccc(CNC(=O)N2CC3(CCCC3)c3cc(-c4cccc(N5CCCC5)c4)ccc32)cc1] | 3.26 | 545.2 | C |
| 6 | 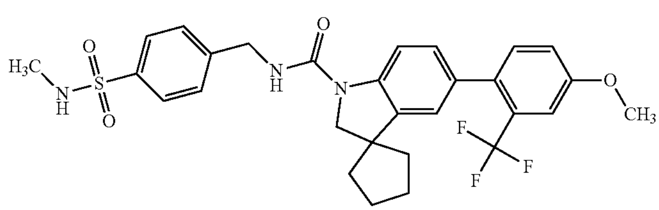 | 3.22 | 574.2 | C |
| 7 | 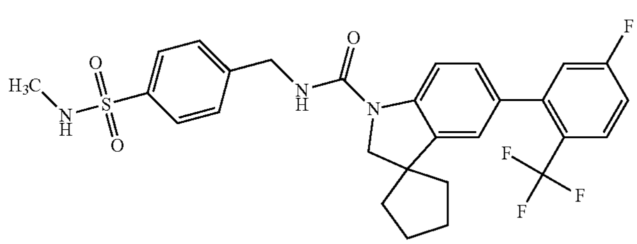 [SMILES: CNS(=O)(=O)c1ccc(CNC(=O)N2CC3(CCCC3)c3cc(-c4cc(F)ccc4C(F)(F)F)ccc32)cc1] | 3.22 | 562.2 | C |
| 8 | 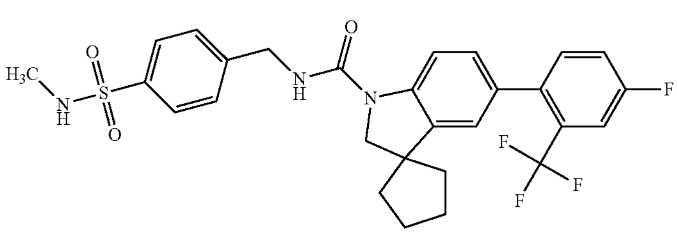 [SMILES: CNS(=O)(=O)c1ccc(CNC(=O)N2CC3(CCCC3)c3cc(-c4ccc(F)cc4C(F)(F)F)ccc32)cc1] | 3.23 | 562.2 | C |

TABLE I-continued

| Example | Structure | RT (min) | m/z [M + H]⁺ | HPLC Method |
|---|---|---|---|---|
| 9 | 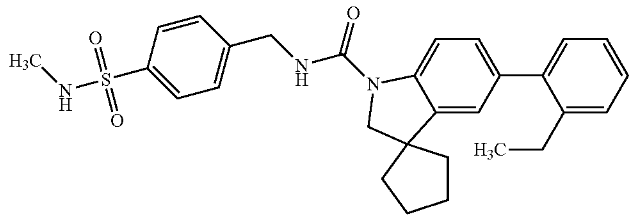 [SMILES: CCc1ccccc1-c1ccc2c(c1)C1(CCCC1)CN2C(=O)NCc1ccc(S(=O)(=O)NC)cc1] | 3.25 | 504.2 | C |
| 10 | 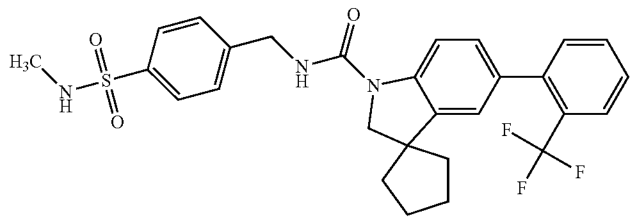 [SMILES: CNS(=O)(=O)c1ccc(CNC(=O)N2CC3(CCCC3)c3cc(-c4ccccc4C(F)(F)F)ccc32)cc1] | 3.21 | 544.3 | C |
| 11 | 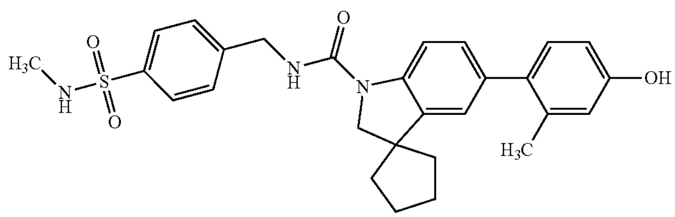 [SMILES: CNS(=O)(=O)c1ccc(CNC(=O)N2CC3(CCCC3)c3cc(-c4ccc(O)cc4C)ccc32)cc1] | 0.90 | 505.6 | A |
| 12 | 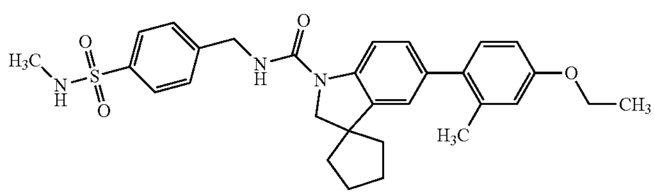 [SMILES: CCOc1ccc(-c2ccc3c(c2)C2(CCCC2)CN3C(=O)NCc2ccc(S(=O)(=O)NC)cc2)c(C)c1] | 3.24 | 534.3 | C |
| 13 | 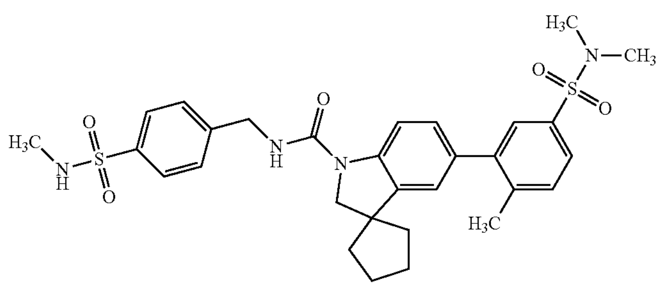 | 3.09 | 597.3 | C |
| 14 | 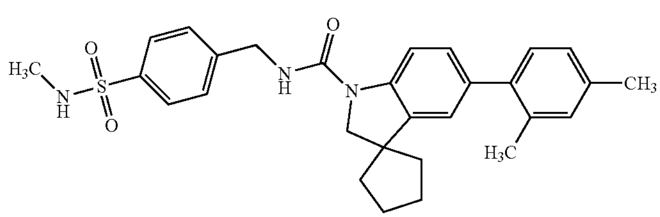 | 3.28 | 504.2 | C |
| 15 | 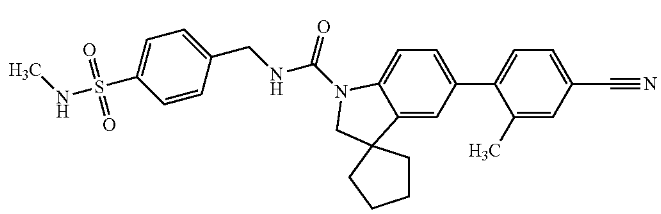 [SMILES: CNS(=O)(=O)c1ccc(CNC(=O)N2CC3(CCCC3)c3cc(-c4ccc(C#N)cc4C)ccc32)cc1] | 3.15 | 515.2 | C |

TABLE I-continued

| Example | Structure | RT (min) | m/z [M + H]⁺ | HPLC Method |
|---|---|---|---|---|
| 16 | 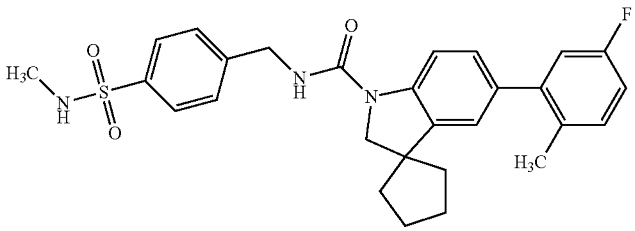 [SMILES: CNS(=O)(=O)c1ccc(CNC(=O)N2CC3(CCCC3)c3cc(-c4cc(F)ccc4C)ccc32)cc1] | 3.22 | 508.2 | C |
| 17 | 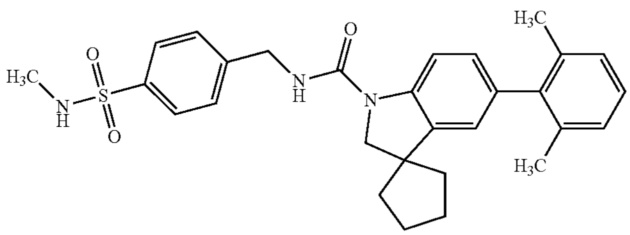 [SMILES: CNS(=O)(=O)c1ccc(CNC(=O)N2CC3(CCCC3)c3cc(-c4c(C)cccc4C)ccc32)cc1] | 3.26 | 504.2 | C |
| 18 | 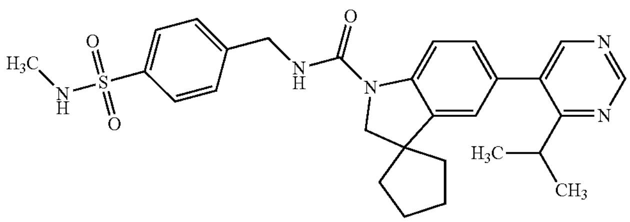 [SMILES: CNS(=O)(=O)c1ccc(CNC(=O)N2CC3(CCCC3)c3cc(-c4cncnc4C(C)C)ccc32)cc1] | 3.11 | 520.3 | C |
| 19 | 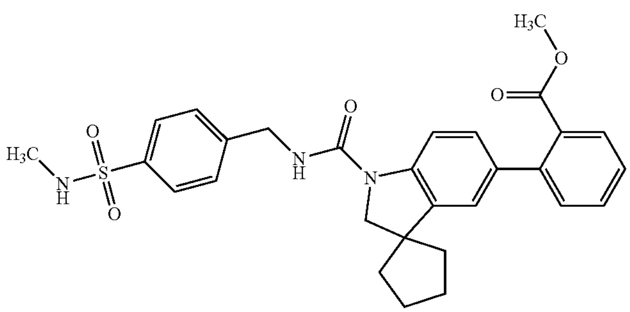 [SMILES: CNS(=O)(=O)c1ccc(CNC(=O)N2CC3(CCCC3)c3cc(-c4ccccc4C(=O)OC)ccc32)cc1] | 3.09 | 534.3 | C |
| 20 | 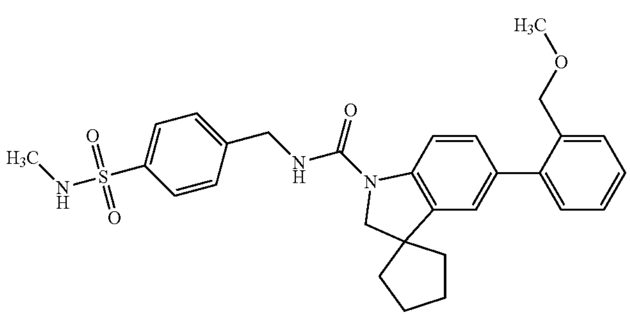 [SMILES: CNS(=O)(=O)c1ccc(CNC(=O)N2CC3(CCCC3)c3cc(-c4ccccc4COC)ccc32)cc1] | 3.14 | 520.3 | C |
| 21 | 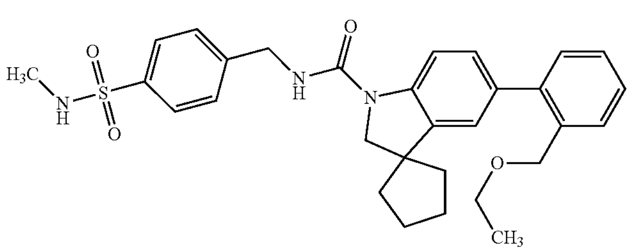 [SMILES: CCOCc1ccccc1-c1ccc2c(c1)C1(CCCC1)CN2C(=O)NCc1ccc(S(=O)(=O)NC)cc1] | 0.25 | 534.2 | C |

TABLE I-continued

| Example | Structure | RT (min) | m/z [M + H]+ | HPLC Method |
|---|---|---|---|---|
| 22 | 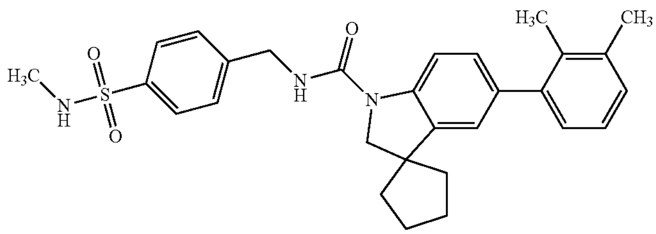 | 3.27 | 504.2 | C |
| 23 | 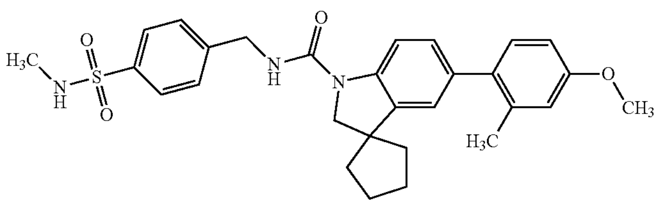 | 3.18 | 520.3 | C |
| 24 | 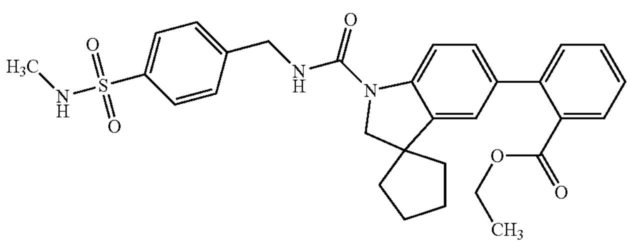 [SMILES: CCOC(=O)c1ccccc1-c1ccc2c(c1)C1(CCCC1)CN2C(=O)NCc1ccc(S(=O)(=O)NC)cc1] | 3.14 | 548.3 | C |
| 25 | 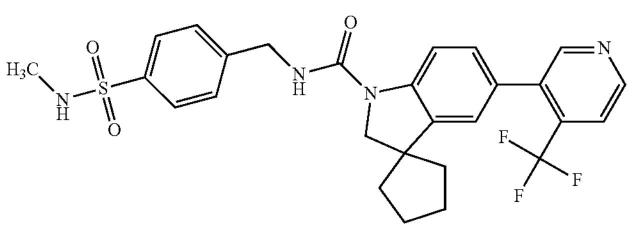 [SMILES: CNS(=O)(=O)c1ccc(CNC(=O)N2CC3(CCCC3)c3cc(-c4cnccc4C(F)(F)F)ccc32)cc1] | 3.1 | 545.3 | C |
| 26 | 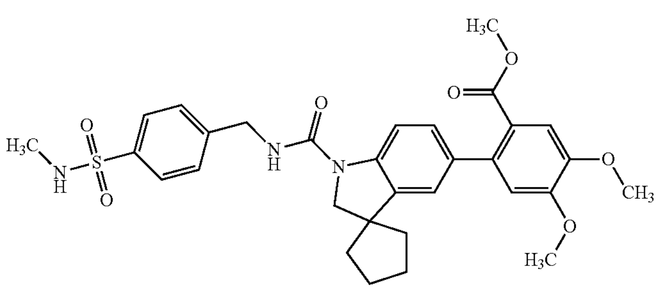 | 3.03 | 594.3 | C |
| 27 | 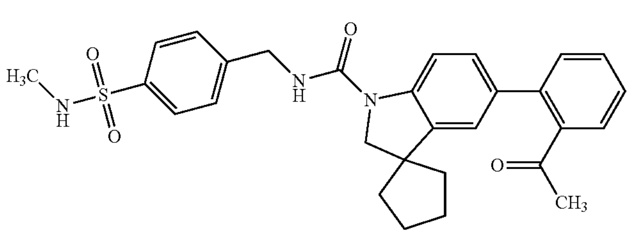 [SMILES: CNS(=O)(=O)c1ccc(CNC(=O)N2CC3(CCCC3)c3cc(-c4ccccc4C(C)=O)ccc32)cc1] | 3.08 | 518.2 | C |

TABLE I-continued

| Example | Structure | RT (min) | m/z [M + H]+ | HPLC Method |
|---|---|---|---|---|
| 28 | 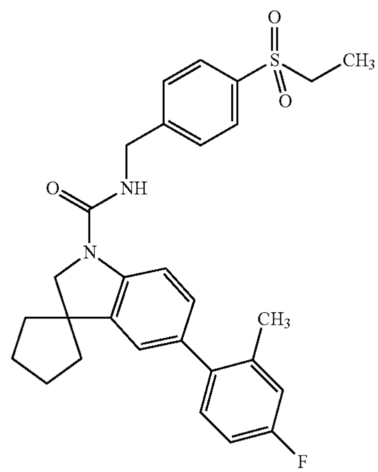 [SMILES: CCS(=O)(=O)c1ccc(CNC(=O)N2CC3(CCCC3)c3cc(-c4ccc(F)cc4C)ccc32)cc1] | 3.26 | 507.3 | C |
| 29 | 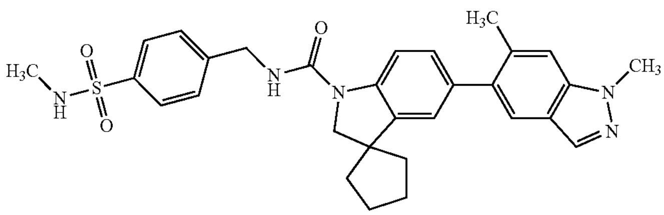 | 3.18 | 544.3 | C |
| 30 | 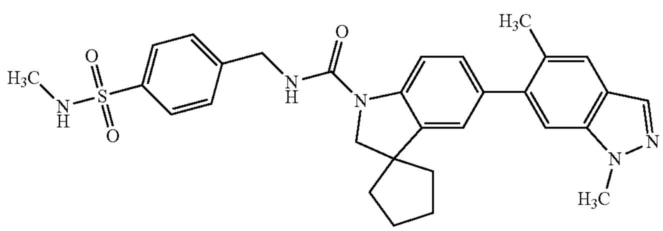 [SMILES: CNS(=O)(=O)c1ccc(CNC(=O)N2CC3(CCCC3)c3cc(-c4cc5c(cnn5C)cc4C)ccc32)cc1] | 3.2 | 544.3 | C |
| 31 | 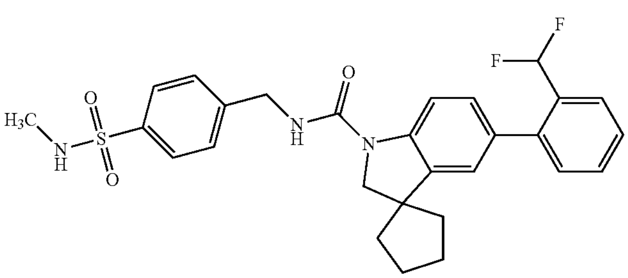 [SMILES: CNS(=O)(=O)c1ccc(CNC(=O)N2CC3(CCCC3)c3cc(-c4ccccc4C(F)F)ccc32)cc1] | 3.17 | 526.3 | C |
| 32 | 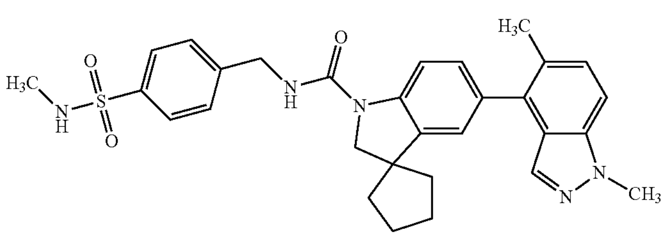 | 3.17 | 544.3 | C |

TABLE I-continued

| Example | Structure | RT (min) | m/z [M + H]+ | HPLC Method |
|---|---|---|---|---|
| 33 | 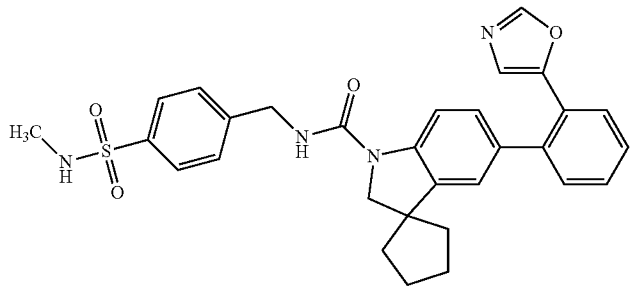 [SMILES: CNS(=O)(=O)c1ccc(CNC(=O)N2CC3(CCCC3)c3cc(-c4ccccc4-c4cnco4)ccc32)cc1] | 3.13 | 543.3 | C |
| 34 | 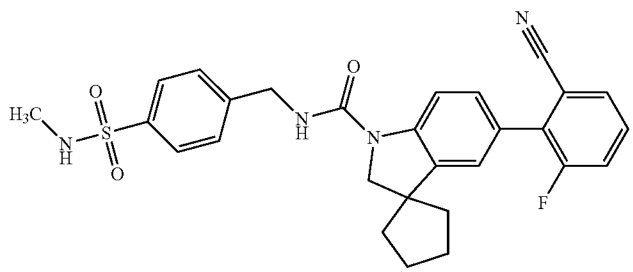 [SMILES: CNS(=O)(=O)c1ccc(CNC(=O)N2CC3(CCCC3)c3cc(-c4c(F)cccc4C#N)ccc32)cc1] | 3.07 | 519.3 | C |
| 35 | 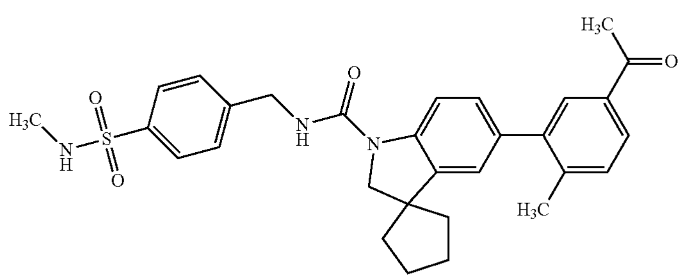 [SMILES: CNS(=O)(=O)c1ccc(CNC(=O)N2CC3(CCCC3)c3cc(-c4cc(C(C)=O)ccc4C)ccc32)cc1] | 3.12 | 532.3 | C |
| 36 | 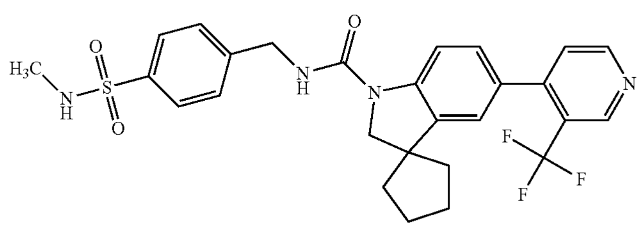 [SMILES: CNS(=O)(=O)c1ccc(CNC(=O)N2CC3(CCCC3)c3cc(-c4ccncc4C(F)(F)F)ccc32)cc1] | 3.11 | 545.3 | C |
| 37 | 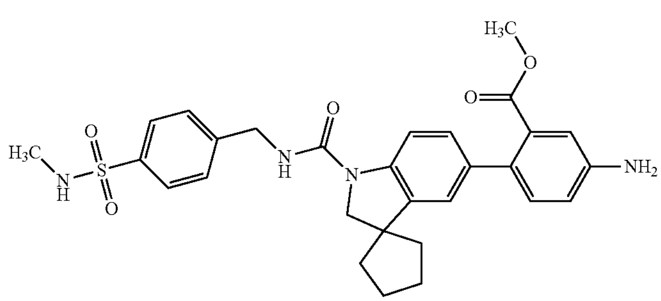 [SMILES: CNS(=O)(=O)c1ccc(CNC(=O)N2CC3(CCCC3)c3cc(-c4ccc(N)cc4C(=O)OC)ccc32)cc1] | 2.92 | 549.3 | C |

TABLE I-continued

| Example | Structure | RT (min) | m/z [M + H]+ | HPLC Method |
|---|---|---|---|---|
| 38 | 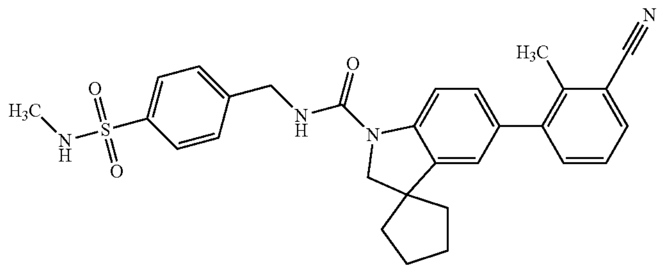 [SMILES: CNS(=O)(=O)c1ccc(CNC(=O)N2CC3(CCCC3)c3cc(-c4cccc(C#N)c4C)ccc32)cc1] | 3.14 | 515.2 | C |
| 39 | 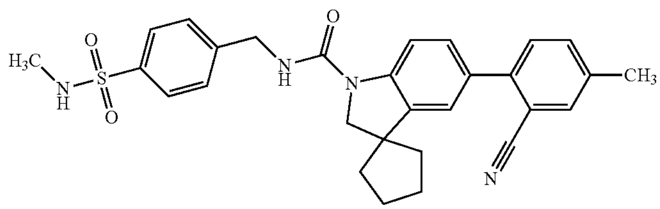 | 3.15 | 515.2 | C |
| 40 | 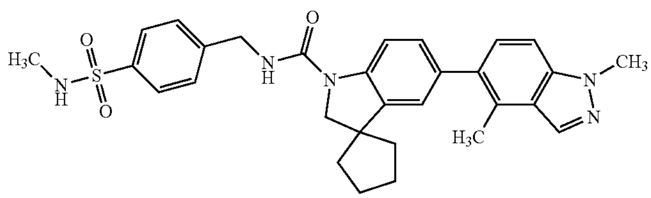 | 3.19 | 544.3 | C |
| 41 | 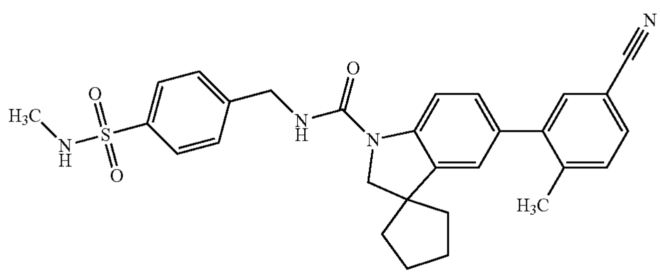 [SMILES: CNS(=O)(=O)c1ccc(CNC(=O)N2CC3(CCCC3)c3cc(-c4cc(C#N)ccc4C)ccc32)cc1] | 3.14 | 515.2 | C |
| 42 | 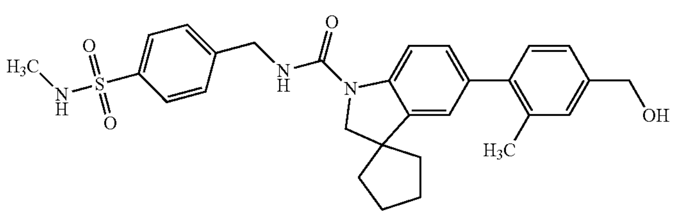 [SMILES: CNS(=O)(=O)c1ccc(CNC(=O)N2CC3(CCCC3)c3cc(-c4ccc(CO)cc4C)ccc32)cc1] | 2.99 | 520.3 | C |
| 43 | 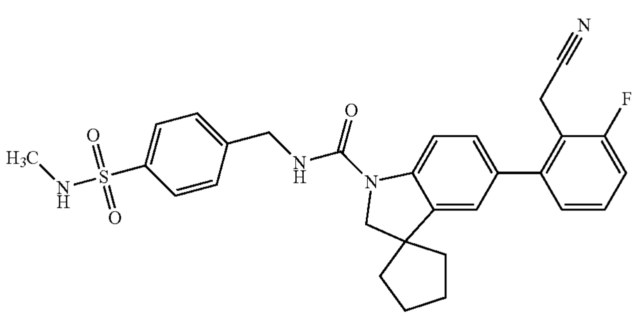 [SMILES: CNS(=O)(=O)c1ccc(CNC(=O)N2CC3(CCCC3)c3cc(-c4cccc(F)c4CC#N)ccc32)cc1] | 3.08 | 533.3 | C |

TABLE I-continued

| Example | Structure | RT (min) | m/z [M + H]+ | HPLC Method |
|---------|-----------|----------|--------------|-------------|
| 44 | 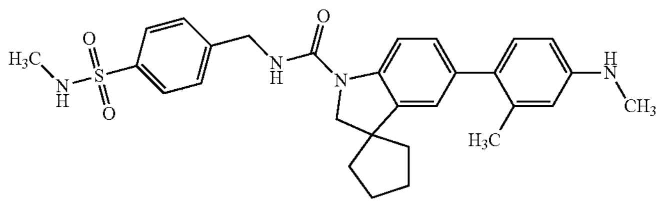 | 2.9 | 519.1 | C |
| 45 | 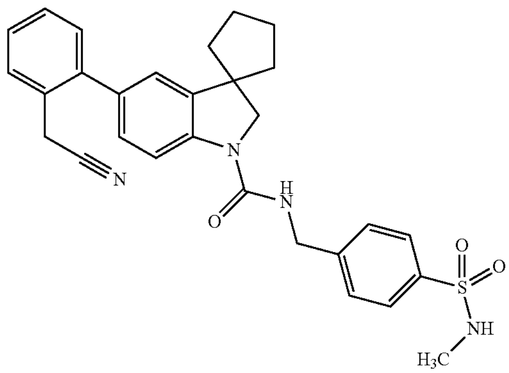 [SMILES: CNS(=O)(=O)c1ccc(CNC(=O)N2CC3(CCCC3)c3cc(-c4ccccc4CC#N)ccc32)cc1] | 3.07 | 515.2 | C |
| 46 | 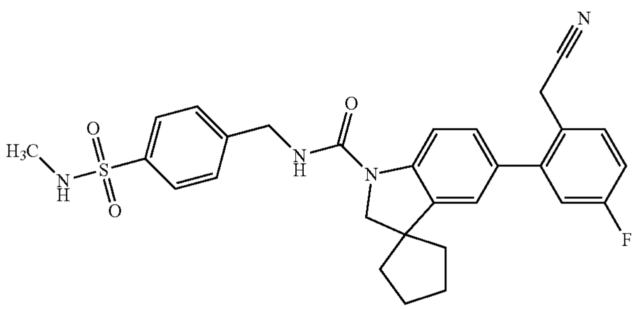 [SMILES: CNS(=O)(=O)c1ccc(CNC(=O)N2CC3(CCCC3)c3cc(-c4cc(F)ccc4CC#N)ccc32)cc1] | 3.09 | 533.3 | C |
| 47 | 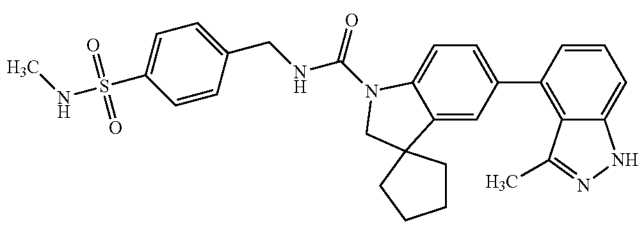 [SMILES: CNS(=O)(=O)c1ccc(CNC(=O)N2CC3(CCCC3)c3cc(-c4cccc5[nH]nc(C)c45)ccc32)cc1] | 3.03 | 530.2 | C |
| 48 | 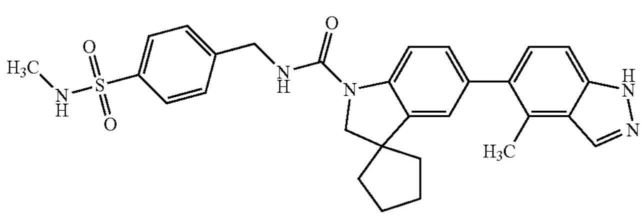 [SMILES: CNS(=O)(=O)c1ccc(CNC(=O)N2CC3(CCCC3)c3cc(-c4ccc5[nH]ncc5c4C)ccc32)cc1] | 3.06 | 530.3 | C |
| 49 | 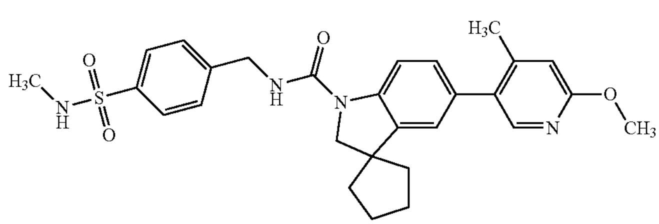 | 3.12 | 521.3 | C |

TABLE I-continued

| Example | Structure | RT (min) | m/z [M + H]+ | HPLC Method |
|---|---|---|---|---|
| 50 | 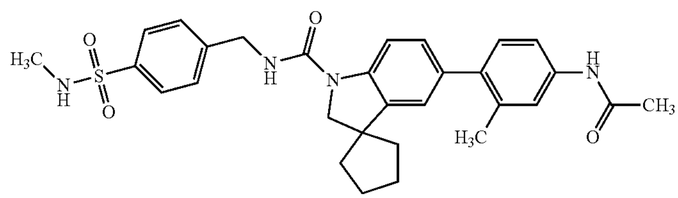 [SMILES: CNS(=O)(=O)c1ccc(CNC(=O)N2CC3(CCCC3)c3cc(-c4ccc(NC(C)=O)cc4C)ccc32)cc1] | 3.0 | 547.3 | C |
| 51 | 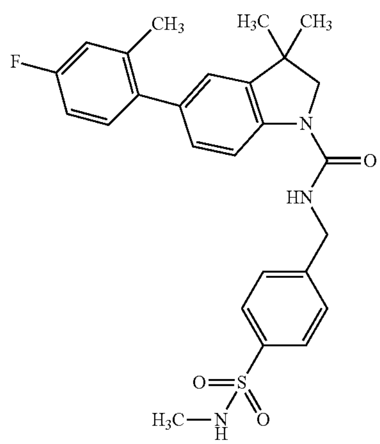 [SMILES: CNS(=O)(=O)c1ccc(CNC(=O)N2CC(C)(C)c3cc(-c4ccc(F)cc4C)ccc32)cc1] | 3.05 | 482.3 | C |
| 52 | 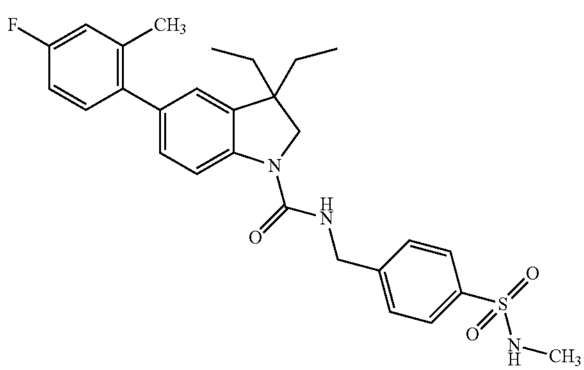 [SMILES: CCC1(CC)CN(C(=O)NCc2ccc(S(=O)(=O)NC)cc2)c2ccc(-c3ccc(F)cc3C)cc21] | 3.21 | 510.3 | C |
| 53 | 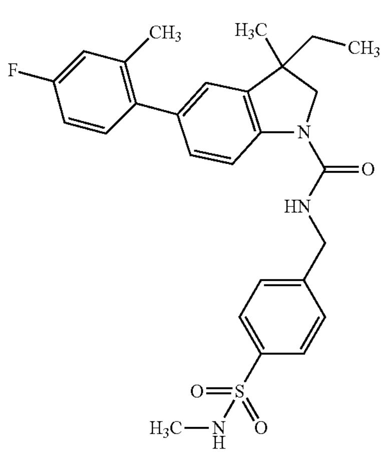 [SMILES: CCC1(C)CN(C(=O)NCc2ccc(S(=O)(=O)NC)cc2)c2ccc(-c3ccc(F)cc3C)cc21] | 3.11 | 496.3 | C |

TABLE I-continued

| Example | Structure | RT (min) | m/z [M + H]+ | HPLC Method |
|---|---|---|---|---|
| 54 | 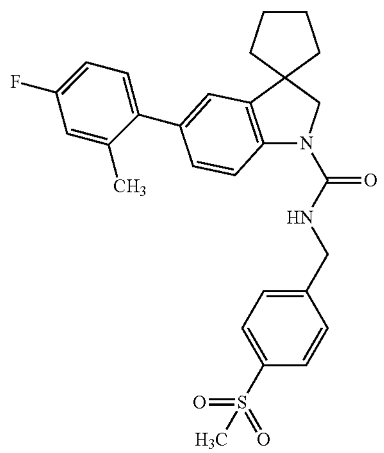 [SMILES: Cc1cc(F)ccc1-c1ccc2c(c1)C1(CCCC1)CN2C(=O)NCc1ccc(S(C)(=O)=O)cc1] | 3.16 | 493.3 | C |
| 55 | 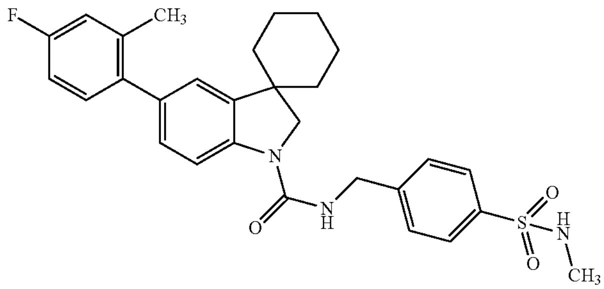 [SMILES: CNS(=O)(=O)c1ccc(CNC(=O)N2CC3(CCCCC3)c3cc(-c4ccc(F)cc4C)ccc32)cc1] | 3.2 | 522.3 | C |
| 56 | 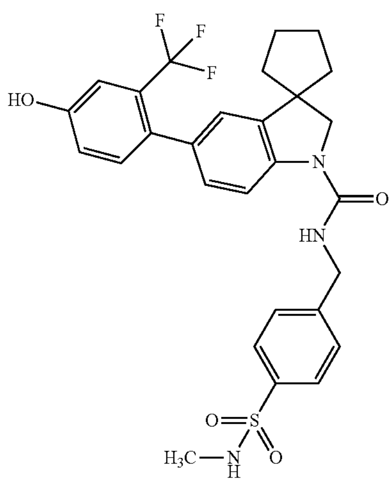 [SMILES: CNS(=O)(=O)c1ccc(CNC(=O)N2CC3(CCCC3)c3cc(-c4ccc(O)cc4C(F)(F)F)ccc32)cc1] | 3.02 | 560.3 | C |
| 57 | 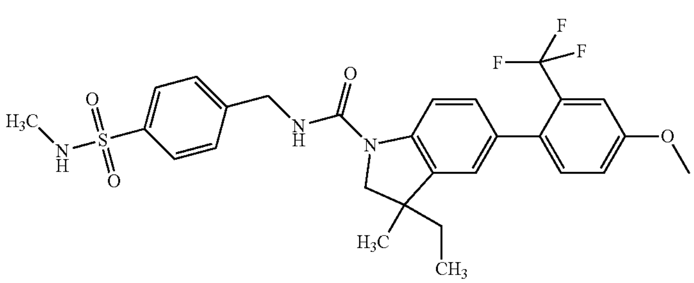 | 3.18 | 562.3 | C |

TABLE I-continued

| Example | Structure | RT (min) | m/z [M + H]+ | HPLC Method |
|---|---|---|---|---|
| 58 | 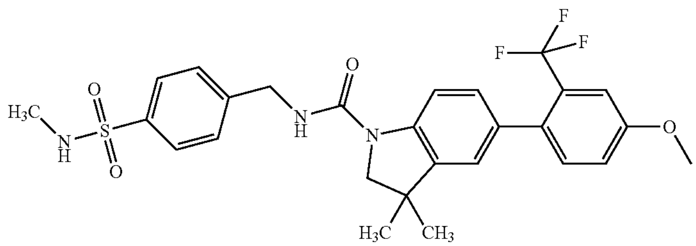 | 3.14 | 548.3 | C |
| 59 | 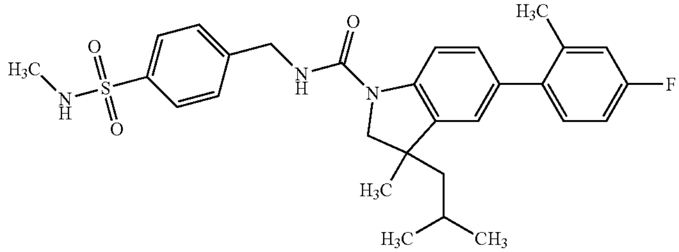 [SMILES: CNS(=O)(=O)c1ccc(CNC(=O)N2CC(C)(CC(C)C)c3cc(-c4ccc(F)cc4C)ccc32)cc1] | 3.27 | 524.3 | C |
| 60 | 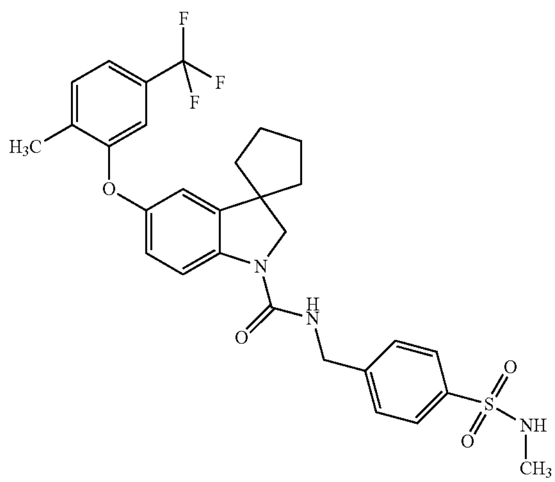 | 3.28 | 574.3 | C |
| 61 | 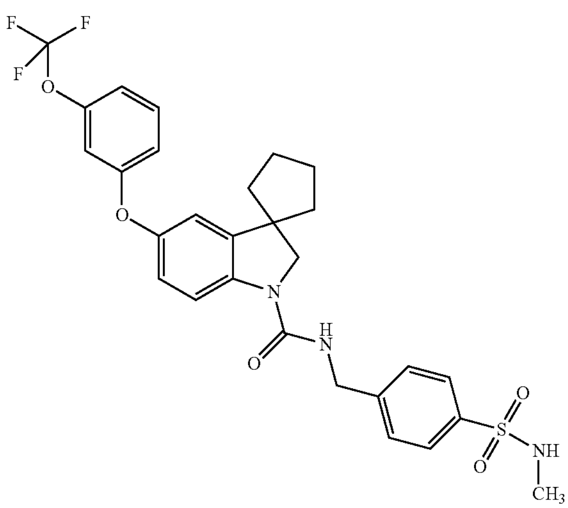 [SMILES: CNS(=O)(=O)c1ccc(CNC(=O)N2CC3(CCCC3)c3cc(Oc4cccc(OC(F)(F)F)c4)ccc32)cc1] | 1.18 | 576.5 | A |

TABLE I-continued

| Example | Structure | RT (min) | m/z [M + H]+ | HPLC Method |
|---|---|---|---|---|
| 62 | 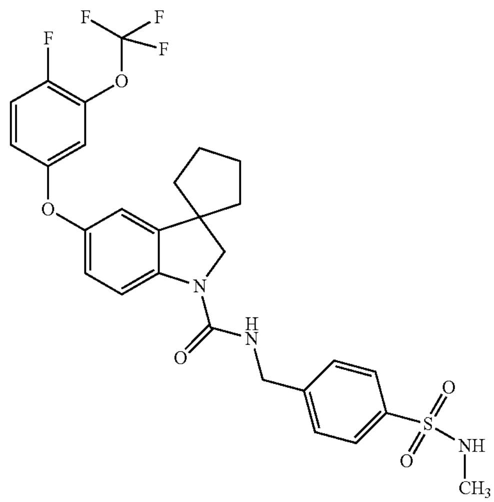 [SMILES: CNS(=O)(=O)c1ccc(CNC(=O)N2CC3(CCCC3)c3cc(Oc4ccc(F)c(OC(F)(F)F)c4)ccc32)cc1] | 3.25 | 594.2 | C |
| 63 | 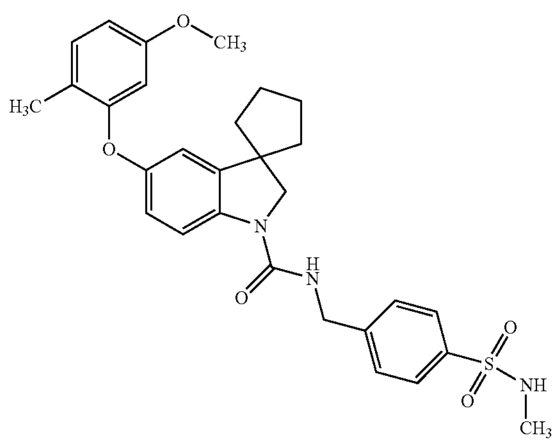 | 3.19 | 536.3 | C |
| 64 | 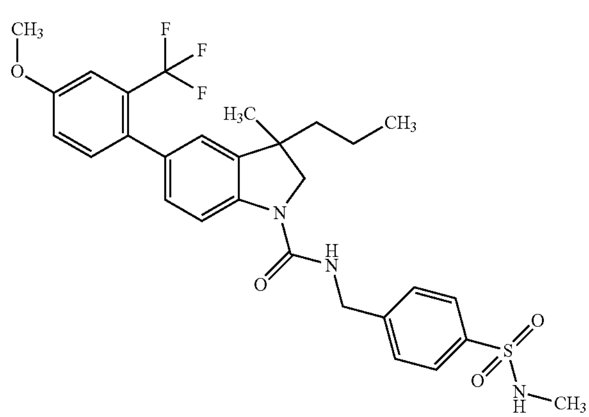 [SMILES: CCCC1(C)CN(C(=O)NCc2ccc(S(=O)(=O)NC)cc2)c2ccc(-c3ccc(OC)cc3C(F)(F)F)cc21] | 3.15 | 576.3 | C |

TABLE I-continued
| Example | Structure | RT (min) | m/z [M + H]+ | HPLC Method |
|---|---|---|---|---|
| 65 | 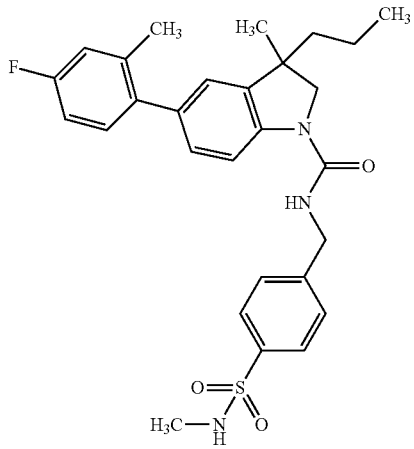 [SMILES: CCCC1(C)CN(C(=O)NCc2ccc(S(=O)(=O)NC)cc2)c2ccc(-c3ccc(F)cc3C)cc21] | 3.14 | 510.3 | C |
| 66 | 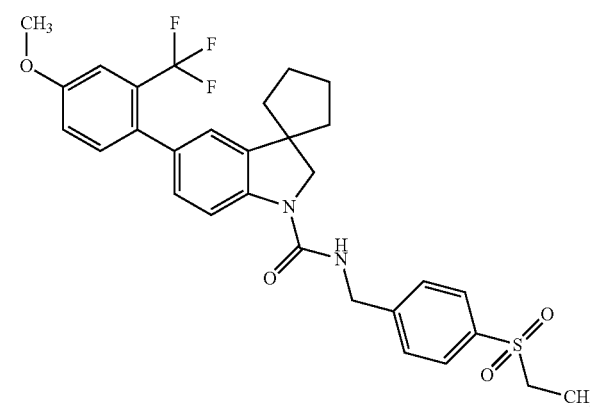 | 3.2 | 573.3 | C |
| 67 | 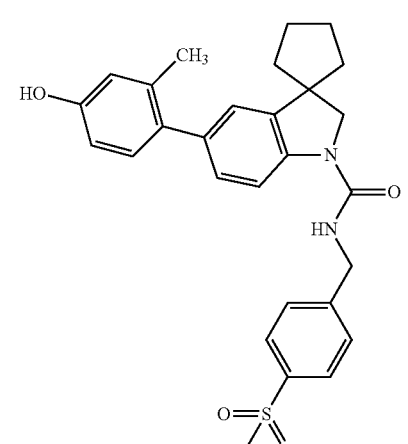 | 2.93 | 505.3 | C |

TABLE I-continued

| Example | Structure | RT (min) | m/z [M + H]+ | HPLC Method |
|---|---|---|---|---|
| 68 | 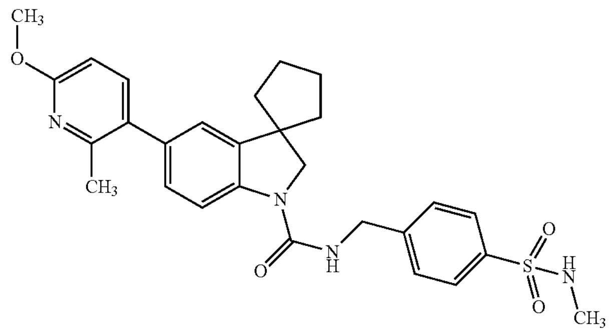 [SMILES: CNS(=O)(=O)c1ccc(CNC(=O)N2CC3(CCCC3)c3cc(-c4ccc(OC)nc4C)ccc32)cc1] | 3.1 | 521.2 | C |
| 69 | 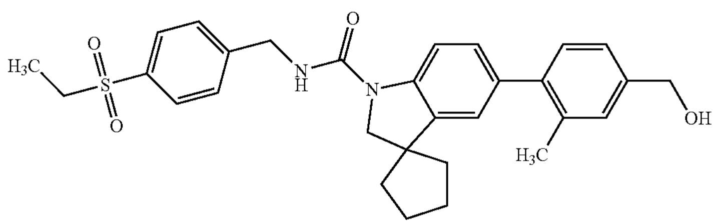 [SMILES: CCS(=O)(=O)c1ccc(CNC(=O)N2CC3(CCCC3)c3cc(-c4ccc(CO)cc4C)ccc32)cc1] | 2.92 | 519.2 | C |
| 70 | 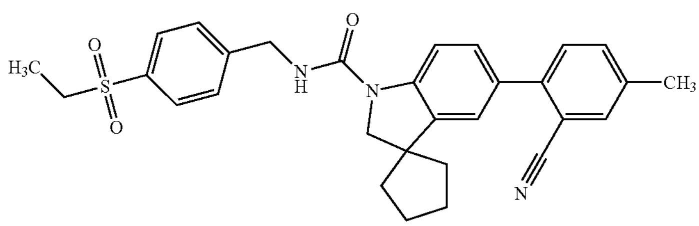 [SMILES: CCS(=O)(=O)c1ccc(CNC(=O)N2CC3(CCCC3)c3cc(-c4ccc(C)cc4C#N)ccc32)cc1] | 3.1 | 514.2 | C |
| 71 | 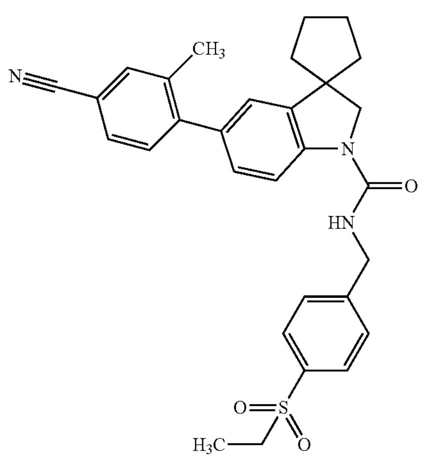 [SMILES: CCS(=O)(=O)c1ccc(CNC(=O)N2CC3(CCCC3)c3cc(-c4ccc(C#N)cc4C)ccc32)cc1] | 3.18 | 514.3 | C |
| 72 | 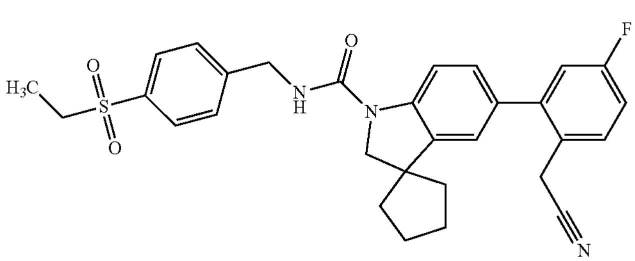 [SMILES: CCS(=O)(=O)c1ccc(CNC(=O)N2CC3(CCCC3)c3cc(-c4cc(F)ccc4CC#N)ccc32)cc1] | 3.11 | 532.3 | C |

TABLE I-continued

| Example | Structure | RT (min) | m/z [M + H]+ | HPLC Method |
|---|---|---|---|---|
| 73 | 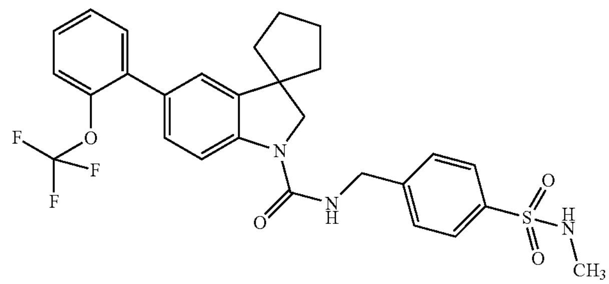 [SMILES: CNS(=O)(=O)c1ccc(CNC(=O)N2CC3(CCCC3)c3cc(-c4ccccc4OC(F)(F)F)ccc32)cc1] | 3.22 | 560.2 | C |
| 74 | 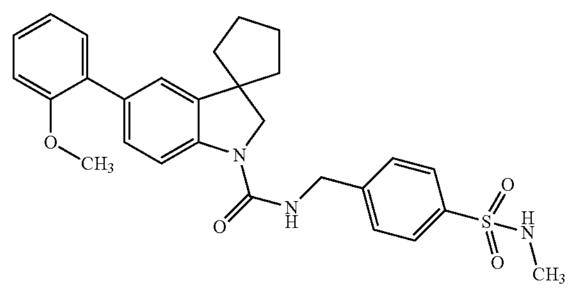 [SMILES: CNS(=O)(=O)c1ccc(CNC(=O)N2CC3(CCCC3)c3cc(-c4ccccc4OC)ccc32)cc1] | 3.13 | 506.3 | C |
| 75 | 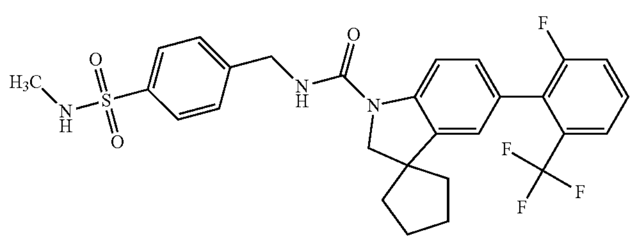 [SMILES: CNS(=O)(=O)c1ccc(CNC(=O)N2CC3(CCCC3)c3cc(-c4c(F)cccc4C(F)(F)F)ccc32)cc1] | 1.2 | 560.2* | A |
| 76 | 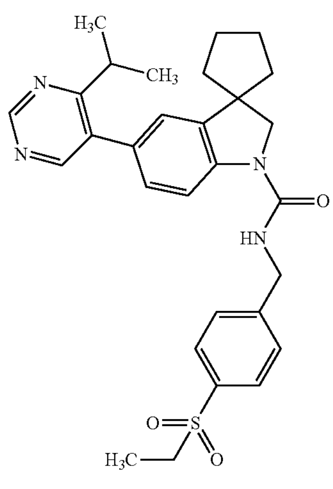 [SMILES: CCS(=O)(=O)c1ccc(CNC(=O)N2CC3(CCCC3)c3cc(-c4cncnc4C(C)C)ccc32)cc1] | 3.17 | 519.3 | C |
| 77 | 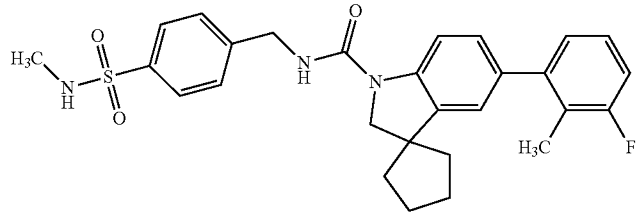 [SMILES: CNS(=O)(=O)c1ccc(CNC(=O)N2CC3(CCCC3)c3cc(-c4cccc(F)c4C)ccc32)cc1] | 3.24 | 508.1 | C |

TABLE I-continued

| Example | Structure | RT (min) | m/z [M + H]⁺ | HPLC Method |
|---------|-----------|----------|--------------|-------------|
| 78 | 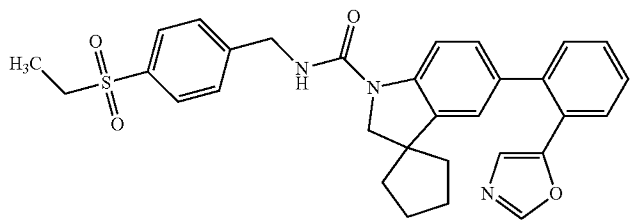 [SMILES: CCS(=O)(=O)c1ccc(CNC(=O)N2CC3(CCCC3)c3cc(-c4ccccc4-c4cnco4)ccc32)cc1] | 3.18 | 542.3 | C |
| 79 | 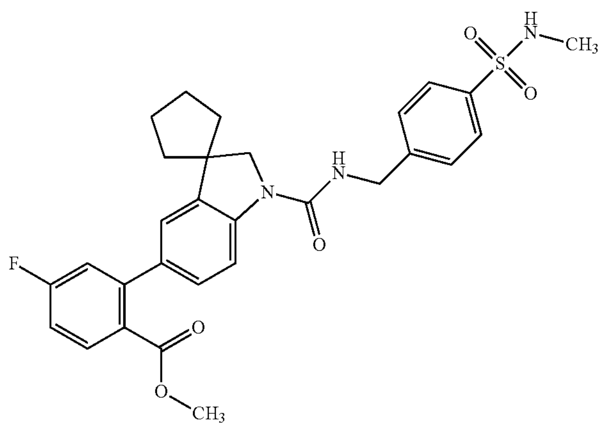 [SMILES: CNS(=O)(=O)c1ccc(CNC(=O)N2CC3(CCCC3)c3cc(-c4cc(F)ccc4C(=O)OC)ccc32)cc1] | 3.13 | 552.4 | C |
| 80 | 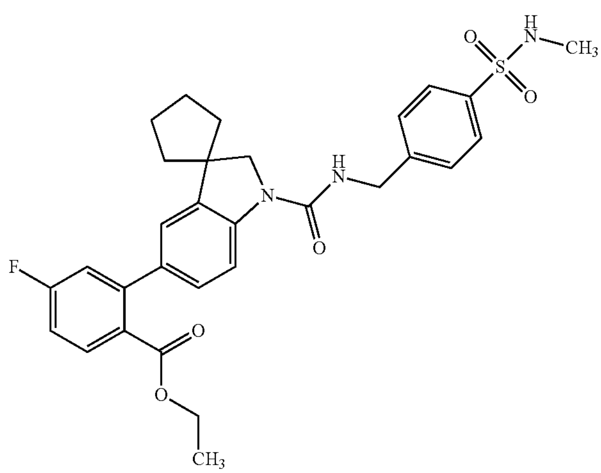 [SMILES: CCOC(=O)c1ccc(F)cc1-c1ccc2c(c1)C1(CCCC1)CN2C(=O)NCc1ccc(S(=O)(=O)NC)cc1] | 3.17 | 566.3 | C |
| 81 | 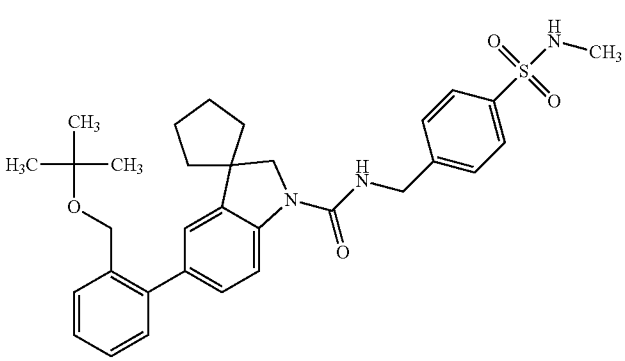 [SMILES: CNS(=O)(=O)c1ccc(CNC(=O)N2CC3(CCCC3)c3cc(-c4ccccc4COC(C)(C)C)ccc32)cc1] | 1.29 | 560.3* | A |

TABLE I-continued

| Example | Structure | RT (min) | m/z [M + H]+ | HPLC Method |
|---|---|---|---|---|
| 82 | 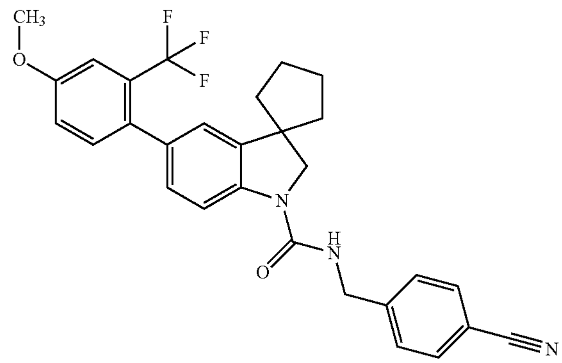 [SMILES: COc1ccc(-c2ccc3c(c2)C2(CCCC2)CN3C(=O)NCc2ccc(C#N)cc2)c(C(F)(F)F)c1] | 3.31 | 506.3 | C |
| 83 | 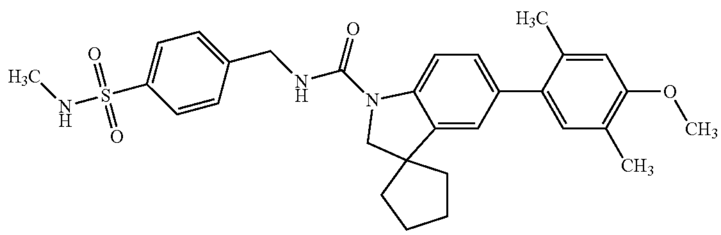 | 3.27 | 534.3 | C |
| 84 | 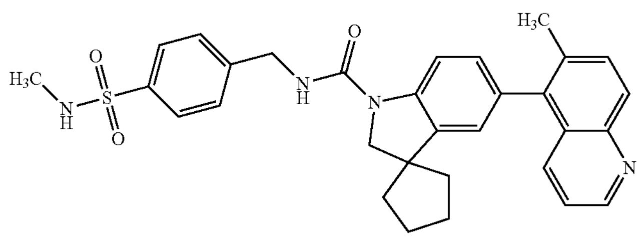 [SMILES: CNS(=O)(=O)c1ccc(CNC(=O)N2CC3(CCCC3)c3cc(-c4c(C)ccc5ncccc45)ccc32)cc1] | 3.09 | 541.3 | C |
| 85 | 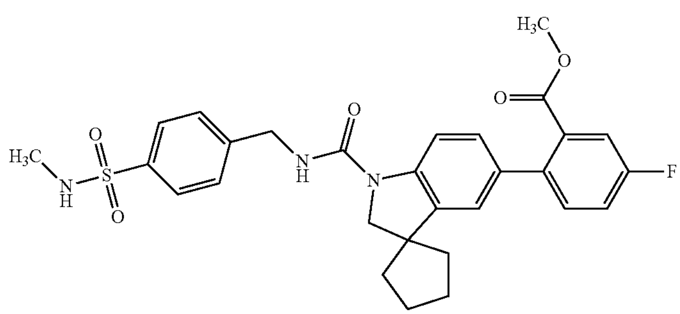 [SMILES: CNS(=O)(=O)c1ccc(CNC(=O)N2CC3(CCCC3)c3cc(-c4ccc(F)cc4C(=O)OC)ccc32)cc1] | 3.13 | 552.4 | C |
| 86 | 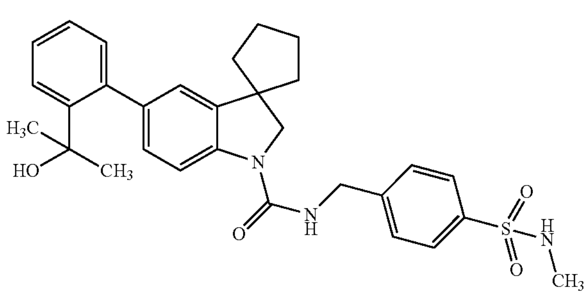 [SMILES: CNS(=O)(=O)c1ccc(CNC(=O)N2CC3(CCCC3)c3cc(-c4ccccc4C(C)(C)O)ccc32)cc1] | 1.07 | 532.3* | A |

TABLE I-continued

| Example | Structure | RT (min) | m/z [M + H]+ | HPLC Method |
|---|---|---|---|---|
| 87 | 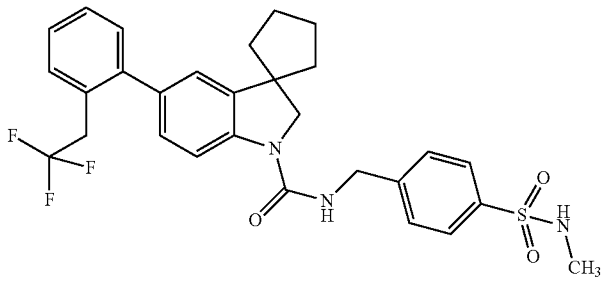 | 3.18 | 558.3 | C |
| 88 | 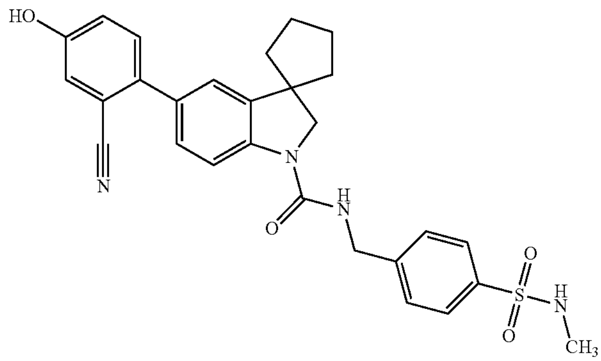 [SMILES: CNS(=O)(=O)c1ccc(CNC(=O)N2CC3(CCCC3)c3cc(-c4ccc(O)cc4C#N)ccc32)cc1] | 2.96 | 517.2 | C |
| 89 | 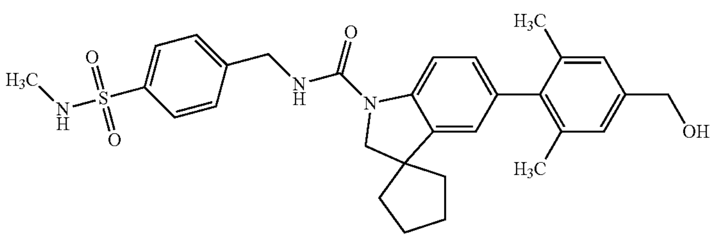 [SMILES: CNS(=O)(=O)c1ccc(CNC(=O)N2CC3(CCCC3)c3cc(-c4c(C)cc(CO)cc4C)ccc32)cc1] | 3.03 | 534.3 | C |
| 90 | 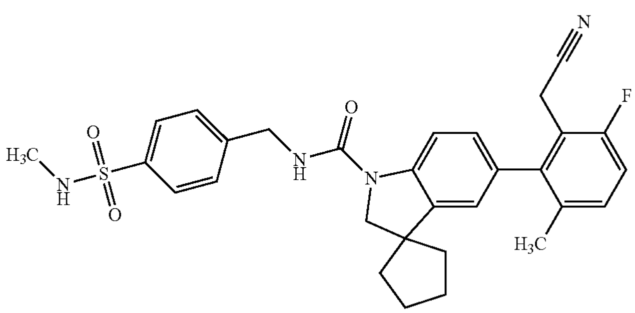 [SMILES: CNS(=O)(=O)c1ccc(CNC(=O)N2CC3(CCCC3)c3cc(-c4c(C)ccc(F)c4CC#N)ccc32)cc1] | 3.14 | 547.3 | C |
| 91 | 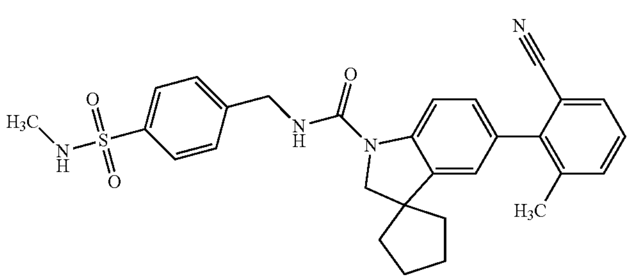 [SMILES: CNS(=O)(=O)c1ccc(CNC(=O)N2CC3(CCCC3)c3cc(-c4c(C)cccc4C#N)ccc32)cc1] | 3.14 | 515.2 | C |

TABLE I-continued

| Example | Structure | RT (min) | m/z [M + H]⁺ | HPLC Method |
|---|---|---|---|---|
| 92 | 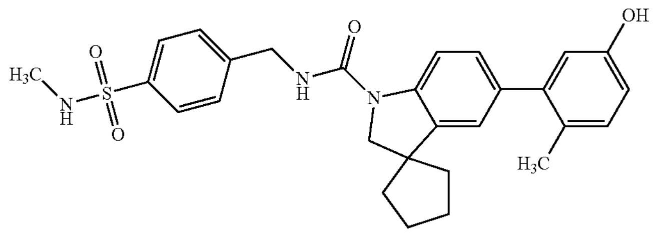 [SMILES: CNS(=O)(=O)c1ccc(CNC(=O)N2CC3(CCCC3)c3cc(-c4cc(O)ccc4C)ccc32)cc1] | 3.01 | 506.2 | C |
| 93 | 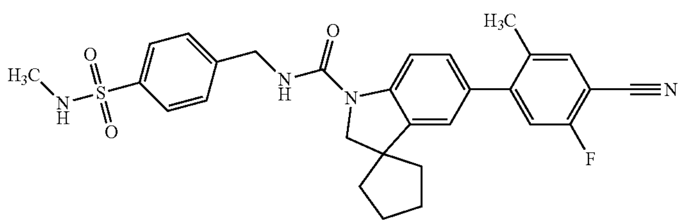 [SMILES: CNS(=O)(=O)c1ccc(CNC(=O)N2CC3(CCCC3)c3cc(-c4cc(F)c(C#N)cc4C)ccc32)cc1] | 3.18 | 533.3 | C |
| 94 | 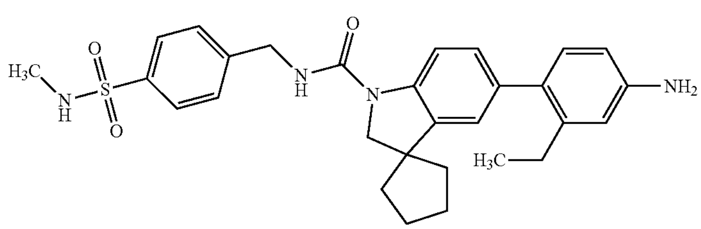 [SMILES: CCc1cc(N)ccc1-c1ccc2c(c1)C1(CCCC1)CN2C(=O)NCc1ccc(S(=O)(=O)NC)cc1] | 2.92 | 519.2 | C |
| 95 | 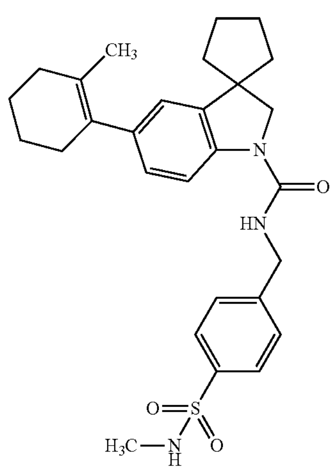 [SMILES: CNS(=O)(=O)c1ccc(CNC(=O)N2CC3(CCCC3)c3cc(C4=C(C)CCCC4)ccc32)cc1] | 3.34 | 494.4 | C |

TABLE I-continued

| Example | Structure | RT (min) | m/z [M + H]⁺ | HPLC Method |
|---|---|---|---|---|
| 96 | 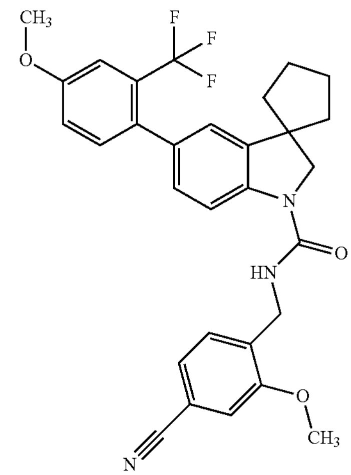 [SMILES: COc1ccc(-c2ccc3c(c2)C2(CCCC2)CN3C(=O)NCc2ccc(C#N)cc2OC)c(C(F)(F)F)c1] | 3.38 | 536.3 | C |
| 97 | 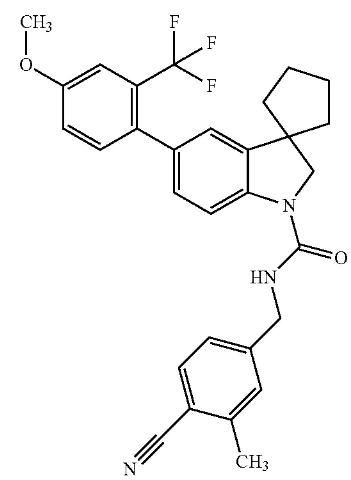 [SMILES: COc1ccc(-c2ccc3c(c2)C2(CCCC2)CN3C(=O)NCc2ccc(C#N)c(C)c2)c(C(F)(F)F)c1] | 3.38 | 520.2 | C |
| 98 | 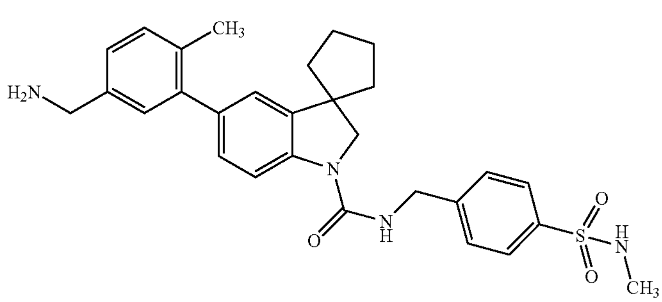 [SMILES: CNS(=O)(=O)c1ccc(CNC(=O)N2CC3(CCCC3)c3cc(-c4cc(CN)ccc4C)ccc32)cc1] | 2.84 | 519.2 | C |
| 99 | 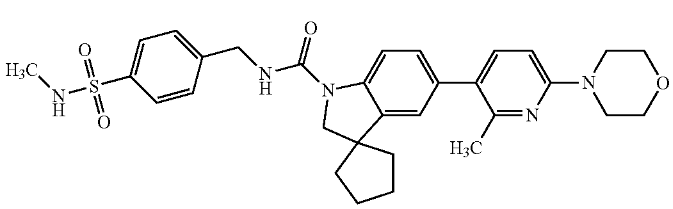 [SMILES: CNS(=O)(=O)c1ccc(CNC(=O)N2CC3(CCCC3)c3cc(-c4ccc(N5CCOCC5)nc4C)ccc32)cc1] | 2.68 | 576.5 | C |

TABLE I-continued
| Example | Structure | RT (min) | m/z [M + H]+ | HPLC Method |
|---|---|---|---|---|
| 100 | 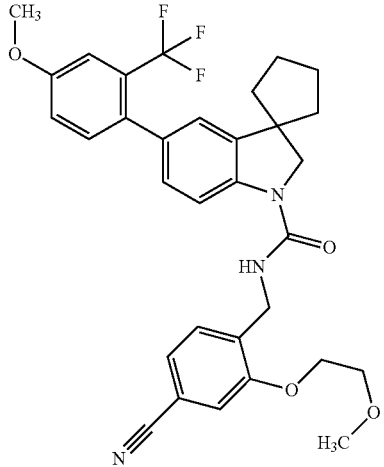 [SMILES: COCCOc1cc(C#N)ccc1CNC(=O)N1CC2(CCCC2)c2cc(-c3ccc(OC)cc3C(F)(F)F)ccc21] | 3.15 | 580.3 | C |
| 101 | 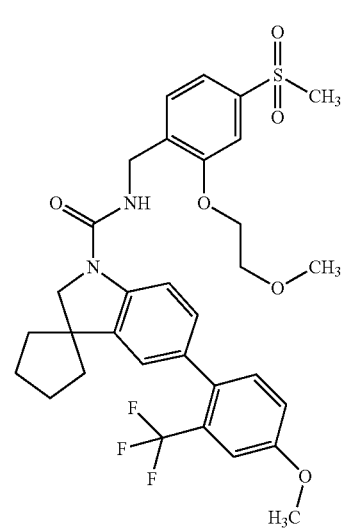 [SMILES: COCCOc1cc(S(C)(=O)=O)ccc1CNC(=O)N1CC2(CCCC2)c2cc(-c3ccc(OC)cc3C(F)(F)F)ccc21] | 3.07 | 633.3 | C |
| 102 | 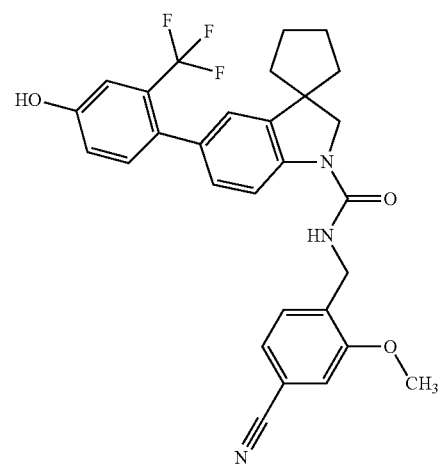 [SMILES: COc1cc(C#N)ccc1CNC(=O)N1CC2(CCCC2)c2cc(-c3ccc(O)cc3C(F)(F)F)ccc21] | 3.15 | 522.3 | C |

TABLE I-continued

| Example | Structure | RT (min) | m/z [M + H]+ | HPLC Method |
|---------|-----------|----------|--------------|-------------|
| 103 | 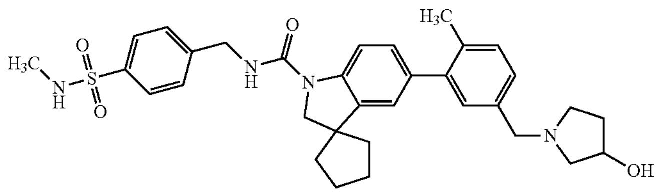 [SMILES: CNS(=O)(=O)c1ccc(CNC(=O)N2CC3(CCCC3)c3cc(-c4cc(CN5CCC(O)C5)ccc4C)ccc32)cc1] | 2.91 | 589.4 | C |
| 104 | 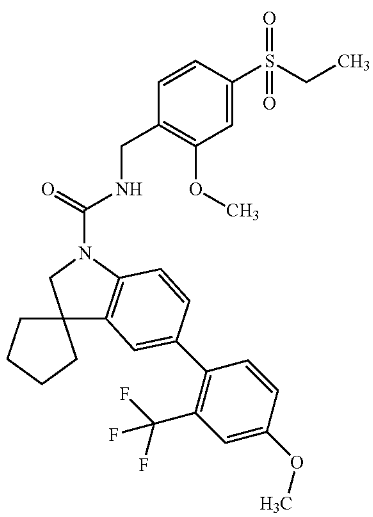 [SMILES: CCS(=O)(=O)c1ccc(CNC(=O)N2CC3(CCCC3)c3cc(-c4ccc(OC)cc4C(F)(F)F)ccc32)c(OC)c1] | 3.3 | 603.3 | C |
| 105 | 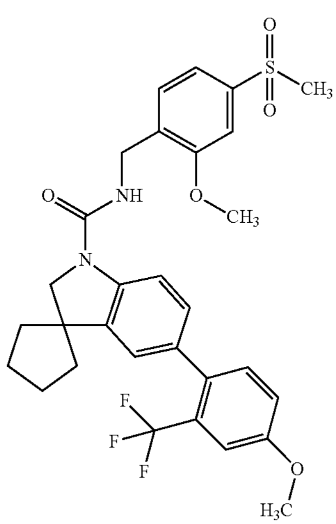 [SMILES: COc1ccc(-c2ccc3c(c2)C2(CCCC2)CN3C(=O)NCc2ccc(S(C)(=O)=O)cc2OC)c(C(F)(F)F)c1] | 3.27 | 589.4 | C |

TABLE I-continued
| Example | Structure | RT (min) | m/z [M + H]+ | HPLC Method |
|---|---|---|---|---|
| 106 | 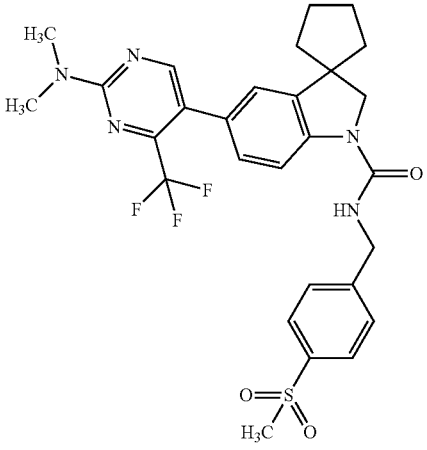 [SMILES: CN(C)c1ncc(-c2ccc3c(c2)C2(CCCC2)CN3C(=O)NCc2ccc(S(C)(=O)=O)cc2)c(C(F)(F)F)n1] | 3.18 | 574.3 | C |
| 107 | 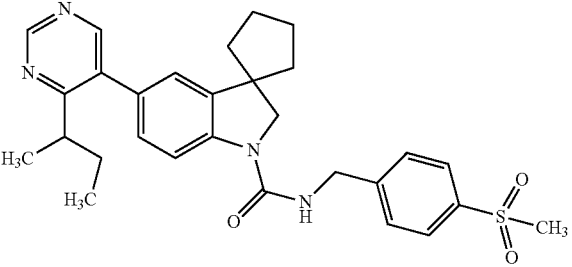 [SMILES: CCC(C)c1ncncc1-c1ccc2c(c1)C1(CCCC1)CN2C(=O)NCc1ccc(S(C)(=O)=O)cc1] | 1.08 | 519.3 | A |
| 108 | 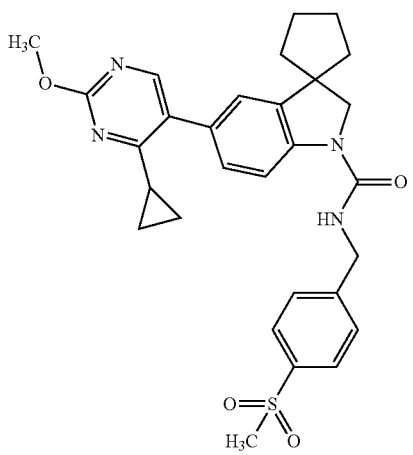 [SMILES: COc1ncc(-c2ccc3c(c2)C2(CCCC2)CN3C(=O)NCc2ccc(S(C)(=O)=O)cc2)c(C2CC2)n1] | 3.07 | 533.3 | C |

TABLE I-continued
| Example | Structure | RT (min) | m/z [M + H]+ | HPLC Method |
|---|---|---|---|---|
| 109 | 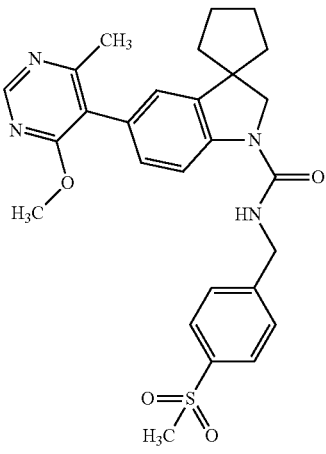 [SMILES: COc1ncnc(C)c1-c1ccc2c(c1)C1(CCCC1)CN2C(=O)NCc1ccc(S(C)(=O)=O)cc1] | 2.9 | 507.2 | C |
| 110 | 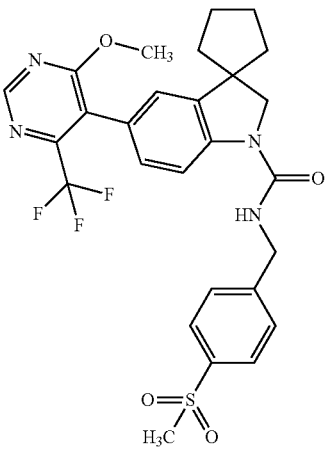 [SMILES: COc1ncnc(C(F)(F)F)c1-c1ccc2c(c1)C1(CCCC1)CN2C(=O)NCc1ccc(S(C)(=O)=O)cc1] | 2.96 | 561.3 | C |
| 111 | 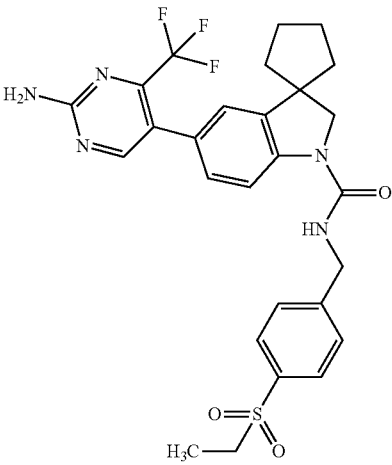 [SMILES: CCS(=O)(=O)c1ccc(CNC(=O)N2CC3(CCCC3)c3cc(-c4cnc(N)nc4C(F)(F)F)ccc32)cc1] | 2.89 | 560.3 | C |

TABLE I-continued
| Example | Structure | RT (min) | m/z [M + H]+ | HPLC Method |
|---|---|---|---|---|
| 112 | 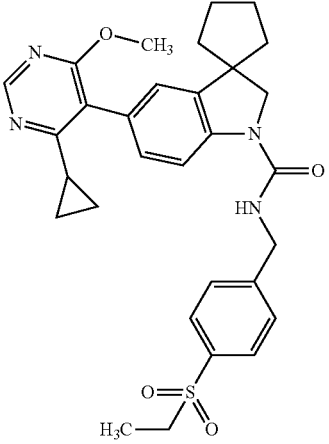 [SMILES: CCS(=O)(=O)c1ccc(CNC(=O)N2CC3(CCCC3)c3cc(-c4c(OC)ncnc4C4CC4)ccc32)cc1] | 3.1 | 547.3 | C |
| 113 | 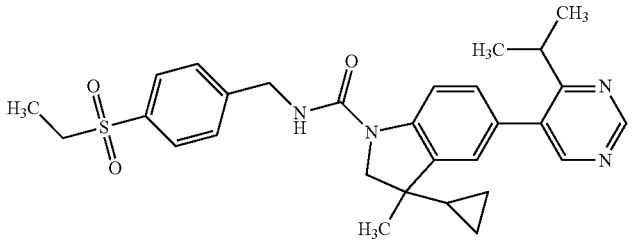 [SMILES: CCS(=O)(=O)c1ccc(CNC(=O)N2CC(C)(C3CC3)c3cc(-c4cncnc4C(C)C)ccc32)cc1] | 3.02 | 518.9 | C |
| 114 | 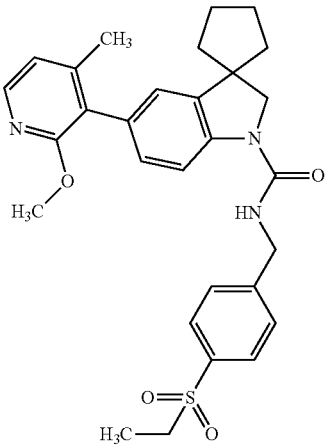 [SMILES: CCS(=O)(=O)c1ccc(CNC(=O)N2CC3(CCCC3)c3cc(-c4c(C)ccnc4OC)ccc32)cc1] | 3.08 | 520.3 | C |

TABLE I-continued
| Example | Structure | RT (min) | m/z [M + H]+ | HPLC Method |
|---|---|---|---|---|
| 115 | 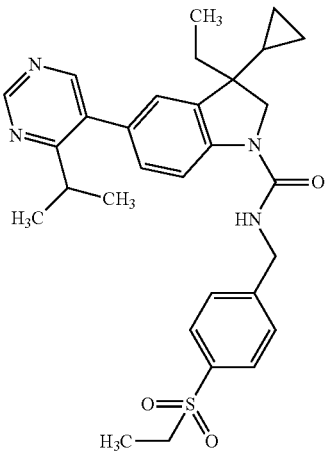 [SMILES: CCC1(C2CC2)CN(C(=O)NCc2ccc(S(=O)(=O)CC)cc2)c2ccc(-c3cncnc3C(C)C)cc21] | 3.08 | 533.3 | C |
| 116 | 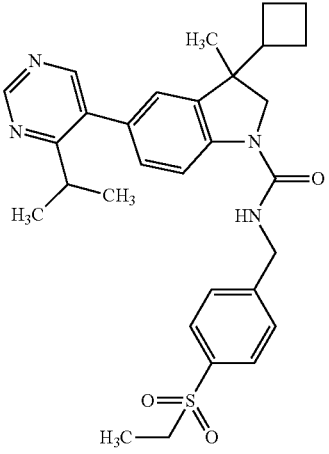 [SMILES: CCS(=O)(=O)c1ccc(CNC(=O)N2CC(C)(C3CCC3)c3cc(-c4cncnc4C(C)C)ccc32)cc1] | 3.13 | 533.3 | C |
| 117 | 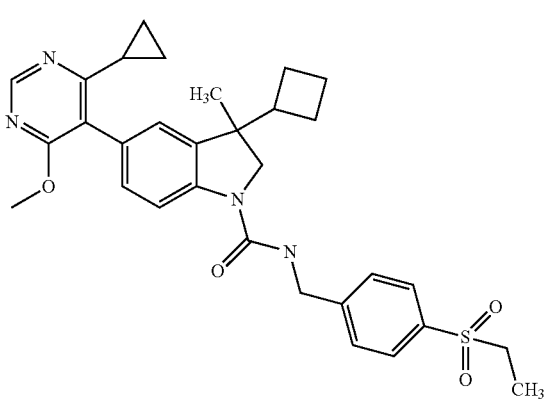 [SMILES: CCS(=O)(=O)c1ccc(CNC(=O)N2CC(C)(C3CCC3)c3cc(-c4c(OC)ncnc4C4CC4)ccc32)cc1] | 3.11 | 561.3 | C |

TABLE I-continued
| Example | Structure | RT (min) | m/z [M + H]+ | HPLC Method |
|---|---|---|---|---|
| 118 | 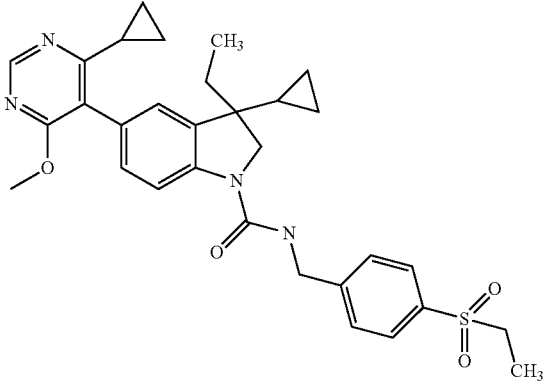 [SMILES: CCC1(C2CC2)CN(C(=O)NCc2ccc(S(=O)(=O)CC)cc2)c2ccc(-c3c(OC)ncnc3C3CC3)cc21] | 3.08 | 561.3 | C |
| 119 | 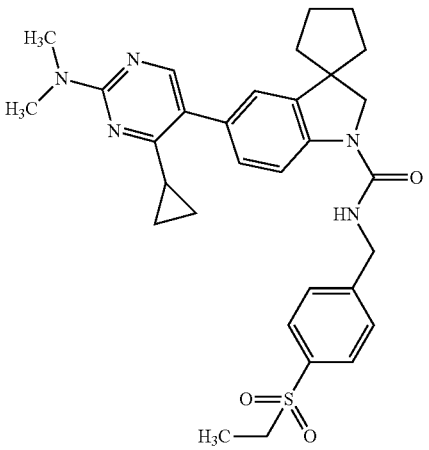 [SMILES: CCS(=O)(=O)c1ccc(CNC(=O)N2CC3(CCCC3)c3cc(-c4cnc(N(C)C)nc4C4CC4)ccc32)cc1] | 3.03 | 560.3 | C |
| 120 | 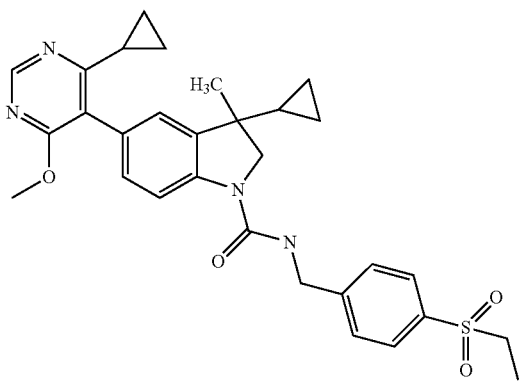 [SMILES: CCS(=O)(=O)c1ccc(CNC(=O)N2CC(C)(C3CC3)c3cc(-c4c(OC)ncnc4C4CC4)ccc32)cc1] | 3.07 | 547.1 | C |

TABLE I-continued

| Example | Structure | RT (min) | m/z [M + H]+ | HPLC Method |
|---------|-----------|----------|--------------|-------------|
| 121 | 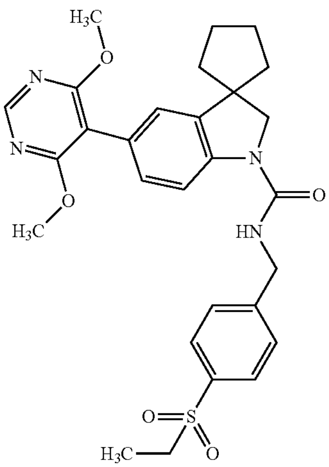 [SMILES: CCS(=O)(=O)c1ccc(CNC(=O)N2CC3(CCCC3)c3cc(-c4c(OC)ncnc4OC)ccc32)cc1] | 3.07 | 537.3 | C |
| 122 | 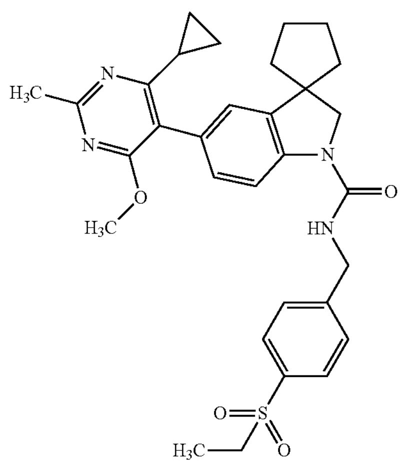 [SMILES: CCS(=O)(=O)c1ccc(CNC(=O)N2CC3(CCCC3)c3cc(-c4c(OC)nc(C)nc4C4CC4)ccc32)cc1] | 3.14 | 561.1 | C |
| 123 | 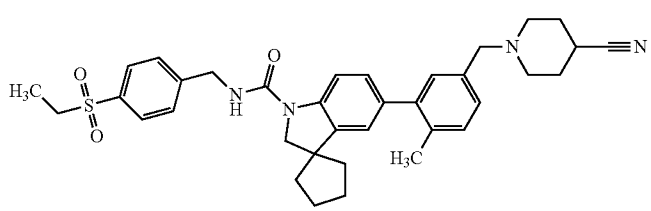 [SMILES: CCS(=O)(=O)c1ccc(CNC(=O)N2CC3(CCCC3)c3cc(-c4cc(CN5CCC(C#N)CC5)ccc4C)ccc32)cc1] | 2.76 | 611.5 | C |
| 124 | 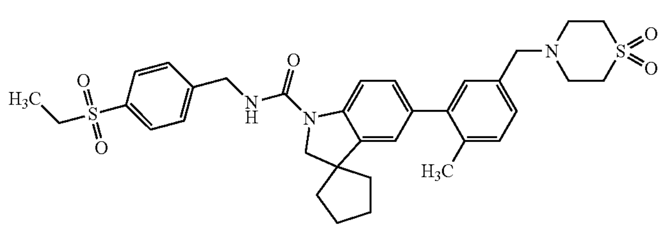 [SMILES: CCS(=O)(=O)c1ccc(CNC(=O)N2CC3(CCCC3)c3cc(-c4cc(CN5CCS(=O)(=O)CC5)ccc4C)ccc32)cc1] | 2.95 | 636.3 | C |

TABLE I-continued

| Example | Structure | RT (min) | m/z [M + H]+ | HPLC Method |
|---|---|---|---|---|
| 125 | 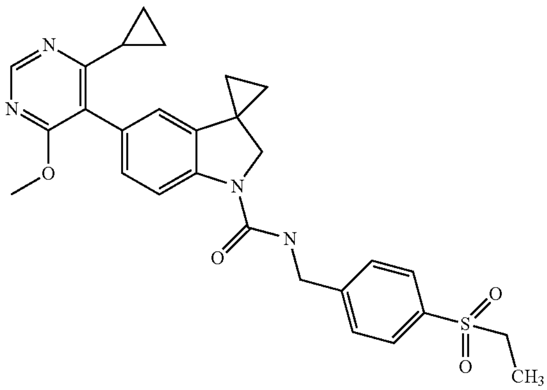 [SMILES: CCS(=O)(=O)c1ccc(CNC(=O)N2CC3(CC3)c3cc(-c4c(OC)ncnc4C4CC4)ccc32)cc1] | 2.98 | 518.9 | C |
| 126 | 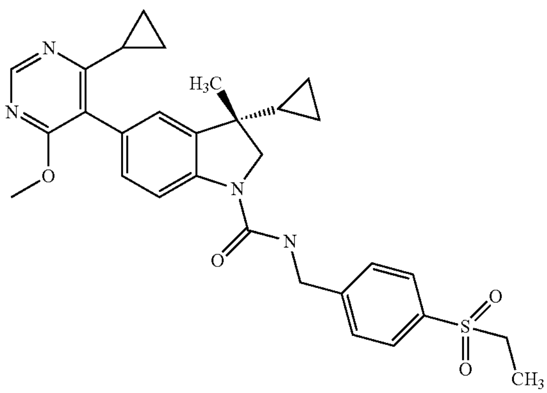 [SMILES: CCS(=O)(=O)c1ccc(CNC(=O)N2C[C@@](C)(C3CC3)c3cc(-c4c(OC)ncnc4C4CC4)ccc32)cc1] | 3.14 | 547.3 | C |
| 127 | 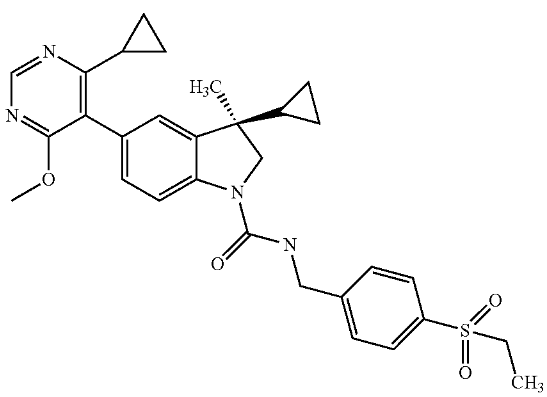 [SMILES: CCS(=O)(=O)c1ccc(CNC(=O)N2C[C@](C)(C3CC3)c3cc(-c4c(OC)ncnc4C4CC4)ccc32)cc1] | 3.13 | 547.3 | C |
| 128 | 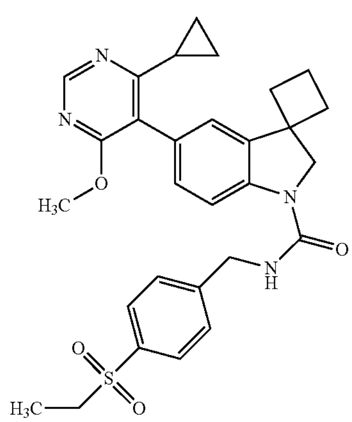 [SMILES: CCS(=O)(=O)c1ccc(CNC(=O)N2CC3(CCC3)c3cc(-c4c(OC)ncnc4C4CC4)ccc32)cc1] | 1.04 | 533.22 | A |

TABLE I-continued

| Example | Structure | RT (min) | m/z [M + H]+ | HPLC Method |
|---------|-----------|----------|--------------|-------------|
| 129 | 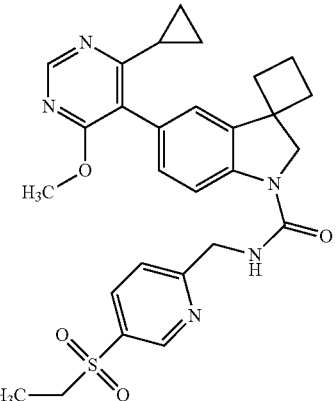 | 1.02 | 534.2 | A |
| 130 | 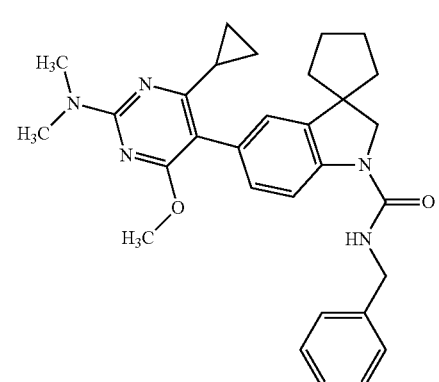 | 2.37 | 590.3 | C |

*m/z [M − H]− or the pharmaceutically acceptable salts thereof.

The present invention further relates to a pharmaceutically acceptable salt of a compound of the formula (I) with inorganic or organic acids or bases.

In another aspect, the invention relates to compounds of formula (I)—or the pharmaceutically acceptable salts thereof—as medicaments.

In another aspect, the invention relates to compounds of formula (I)—or the pharmaceutically acceptable salts thereof—for use in a method for treatment of a patent.

In another aspect, the invention relates to compounds of formula (I)—or the pharmaceutically acceptable salts thereof—for use in the treatment of autoimmune diseases and allergic disorders.

In another aspect, the invention relates to the use of compounds of formula (I)—or the pharmaceutically acceptable salts thereof—for preparing a pharmaceutical composition for the treatment of autoimmune diseases and allergic disorders.

In another aspect, the invention relates to a method for the treatment of autoimmune diseases and allergic disorders comprising administering a therapeutically effective amount of a compound of formula (I)—or one of the pharmaceutically acceptable salts thereof—to a patient.

In another aspect, the invention relates to a pharmaceutical preparation containing as active substance one or more compounds of formula (I)—or the pharmaceutically acceptable salts thereof—optionally in combination with conventional excipients and/or carriers.

Definitions and Conventions Used

Terms that are not specifically defined here have the meanings that are apparent to the skilled man in the light of the overall disclosure and the context as a whole.

As used herein, the following definitions apply, unless stated otherwise:

The use of the prefix $C_{x\text{-}y}$, wherein x and y each represent a natural number, indicates that the chain or ring structure or combination of chain and ring structure as a whole, specified and mentioned in direct association, may consist of a maximum of y and a minimum of x carbon atoms.

In general, for groups comprising two or more subgroups, unless otherwise indicated the last named subgroup is the radical attachment point, for example, the substituent "aryl-$C_{1\text{-}3}$-alkyl" means an aryl group which is bound to a $C_{1\text{-}3}$-alkyl-group, the latter of which is bound to the core or to the group to which the substituent is attached. However, if a bond is depicted just prior to the first named subgroup, then that first named subgroup is the radical attachment point, for example, the substituent "—$S(O)_m C_{1\text{-}6}$alkyl"

means a $C_{1-6}$-alkyl-group which is bound to an $S(O)_m$ group, the latter of which is bound to the core or to the group to which the substituent is attached.

Alkyl denotes monovalent, saturated hydrocarbon chains, which may be present in both straight-chain (unbranched) and branched form. If an alkyl is substituted, the substitution may take place independently of one another, by mono- or polysubstitution in each case, on all the hydrogen-carrying carbon atoms.

For example, the term "$C_{1-5}$alkyl" includes for example $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—, $H_3C$—$CH_2$—$CH_2$—$CH_2$—$CH_2$—, $H_3C$—$CH_2$—$CH_2$—$CH(CH_3)$—, $H_3C$—$CH_2$—$CH(CH_3)$—$CH_2$—, $H_3C$—$CH(CH_3)$—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$— and $H_3C$—$CH_2$—$CH(CH_2CH_3)$—.

Further examples of alkyl are methyl (Me; —$CH_3$), ethyl (Et; —$CH_2CH_3$), 1-propyl (n-propyl; n-Pr; —$CH_2CH_2CH_3$), 2-propyl (i-Pr; iso-propyl; —$CH(CH_3)_2$), 1-butyl (n-butyl; n-Bu; —$CH_2CH_2CH_2CH_3$), 2-methyl-1-propyl (iso-butyl; i-Bu; —$CH_2CH(CH_3)_2$), 2-butyl (sec-butyl; sec-Bu; —$CH(CH_3)CH_2CH_3$), 2-methyl-2-propyl (tert-butyl; t-Bu; —$C(CH_3)_3$), 1-pentyl n-pentyl; —$CH_2CH_2CH_2CH_2CH_3$), 2-pentyl (—$CH(CH_3)CH_2CH_2CH_3$), 3-pentyl (—$CH(CH_2CH_3)_2$), 3-methyl-1-butyl (iso-pentyl; —$CH_2CH_2CH(CH_3)_2$), 2-methyl-2-butyl (—$C(CH_3)_2CH_2CH_3$), 3-methyl-2-butyl (—$CH(CH_3)CH(CH_3)_2$), 2,2-dimethyl-1-propyl(neo-pentyl; —$CH_2C(CH_3)_3$), 2-methyl-1-butyl (—$CH_2CH(CH_3)CH_2CH_3$), 1-hexyl (n-hexyl; —$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), 2,3-dimethyl-1-butyl (—$CH_2CH(CH_3)CH(CH_3)CH_3$), 2,2-dimethyl-1-butyl (—$CH_2C(CH_3)_2CH_2CH_3$), 3,3-dimethyl-1-butyl (—$CH_2CH_2C(CH_3)_3$), 2-methyl-1-pentyl (—$CH_2CH(CH_3)CH_2CH_2CH_3$), 3-methyl-1-pentyl (—$CH_2CH_2CH(CH_3)CH_2CH_3$), 1-heptyl (n-heptyl), 2-methyl-1-hexyl, 3-methyl-1-hexyl, 2,2-dimethyl-1-pentyl, 2,3-dimethyl-1-pentyl, 2,4-dimethyl-1-pentyl, 3,3-dimethyl-1-pentyl, 2,2,3-trimethyl-1-butyl, 3-ethyl-1-pentyl, 1-octyl (n-octyl), 1-nonyl (n-nonyl); 1-decyl (n-decyl) etc.

By the terms propyl, butyl, pentyl, hexyl, heptyl, octyl, nonyl, decyl etc. without any further definition are meant saturated hydrocarbon groups with the corresponding number of carbon atoms, wherein all isomeric forms are included.

The above definition for alkyl also applies if alkyl is a part of another (combined) group such as for example $C_{x-y}$alkylamino or $C_{x-y}$alkoxy.

Unlike alkyl, alkenyl consists of at least two carbon atoms, wherein at least two adjacent carbon atoms are joined together by a C—C double bond and a carbon atom can only be part of one C—C double bond. If in an alkyl as hereinbefore defined having at least two carbon atoms, two hydrogen atoms on adjacent carbon atoms are formally removed and the free valencies are saturated to form a second bond, the corresponding alkenyl is formed.

Alkenyl may optionally be present in the cis or trans or E or Z orientation with regard to the double bond(s).

Unlike alkyl, alkynyl consists of at least two carbon atoms, wherein at least two adjacent carbon atoms are joined together by a C—C triple bond. If in an alkyl as hereinbefore defined having at least two carbon atoms, two hydrogen atoms in each case at adjacent carbon atoms are formally removed and the free valencies are saturated to form two further bonds, the corresponding alkynyl is formed.

Haloalkyl (haloalkenyl, haloalkynyl) is derived from the previously defined alkyl (alkenyl, alkynyl) by replacing one or more hydrogen atoms of the hydrocarbon chain independently of one another by halogen atoms, which may be identical or different. If a haloalkyl (haloalkenyl, haloalkynyl) is to be further substituted, the substitutions may take place independently of one another, in the form of mono- or polysubstitutions in each case, on all the hydrogen-carrying carbon atoms.

Examples of haloalkyl (haloalkenyl, haloalkynyl) are —$CF_3$, —$CHF_2$, —$CH_2F$, —$CF_2CF_3$, —$CHFCF_3$, —$CH_2CF_3$, —$CF_2CH_3$, —$CHFCH_3$, —$CF_2CF_2CF_3$, —$CF_2CH_2CH_3$, —CF=$CF_2$, —CCl=$CH_2$, —CBr=$CH_2$, —C≡C—$CF_3$, —$CHFCH_2CH_3$, —$CHFCH_2CF_3$ etc.

Halogen relates to fluorine, chlorine, bromine and/or iodine atoms.

The term "$C_{3-12}$ cycloalkyl" refers to a nonaromatic 3 to 12-membered (but preferably, 3 to 6-membered) monocyclic carbocyclic radical or a nonaromatic 6 to 10-membered fused bicyclic, bridged bicyclic, or spirocyclic carbocyclic radical. The $C_{3-12}$ cycloalkyl may be either saturated or partially unsaturated, and the carbocycle may be attached by any atom of the cycle which results in the creation of a stable structure. Non-limiting examples of 3 to 10-membered monocyclic carbocycles include cyclopropyl, cyclobutyl, cyclopentyl, cyclopentenyl, cyclohexyl, cyclohexenyl, cycloheptanyl, cycloheptenyl, and cyclohexanone. Non-limiting examples of 6 to 10-membered fused bicyclic carbocyclic radicals include bicyclo[1.1.1]pentane, bicyclo[3.3.0]octane, bicyclo[4.3.0]nonane, and bicyclo[4.4.0]decanyl (decahydronaphthalenyl). Non-limiting examples of 6 to 10-membered bridged bicyclic carbocyclic radicals include bicyclo[2.2.2]heptanyl, bicyclo[2.2.2]octanyl, and bicyclo[3.2.1]octanyl. Non-limiting examples of 6 to 10-membered spirocyclic carbocyclic radicals include but are not limited to spiro[3,3]heptanyl, spiro[3,4]octanyl and spiro[4,4]heptanyl.

The term "$C_{2-10}$ heterocyclyl" refers to a heterocyclic ring system that contains 2-10 carbon atoms and one to four heteroatom groups chosen from NH, NR', oxygen and sulfur wherein R' is $C_{1-6}$ alkyl and includes stable nonaromatic 4-8 membered monocyclic heterocyclic radical or a stable nonaromatic 6 to 11-membered fused bicyclic, bridged bicyclic or spirocyclic heterocyclic radical. The heterocycle may be either saturated or partially unsaturated. Non-limiting examples of nonaromatic 4-8 membered monocyclic heterocyclic radicals include tetrahydrofuranyl, azetidinyl, pyrrolidinyl, pyranyl, tetrahydropyranyl, dioxanyl, thiomorpholinyl, 1,1-dioxo-1.lamda$_6$-thiomorpholinyl, morpholinyl, piperidinyl, piperazinyl, and azepinyl. Non-limiting examples of nonaromatic 6 to 11-membered fused bicyclic radicals include octahydroindolyl, octahydrobenzofuranyl, and octahydrobenzothiophenyl. Non-limiting examples of nonaromatic 6 to 11-membered bridged bicyclic radicals include 2-azabicyclo[2.2.1]heptanyl, 3-azabicyclo[3.1.0]hexanyl, and 3-azabicyclo[3.2.1]octanyl. Non-limiting examples of nonaromatic 6 to 11-membered spirocyclic heterocyclic radicals include 7-aza-spiro[3,3]heptanyl, 7-spiro[3,4]octanyl, and 7-aza-spiro[3,4]octanyl. Sulfur and nitrogen may optionally be present in all the possible oxidation stages (sulphur→sulphoxide —SO—, sulphone —SO$_2$—; nitrogen→N-oxide).

The term "aryl" refers to an aromatic hydrocarbon rings containing from six to fourteen carbon ring atoms (e.g., a C$_{6-14}$ aryl, preferably C$_{6-10}$ aryl). The term C$_{6-14}$ aryl includes monocyclic rings, fused rings and bicyclic rings where at least one of the rings is aromatic. Non-limiting examples of C$_{6-14}$ aryls include phenyl, indanyl, indenyl, benzocyclobutanyl, dihydronaphthyl, tetrahydronaphthyl, naphthyl, benzocycloheptanyl and benzocycloheptenyl.

As used herein, the term "C$_{2-10}$ heteroaryl" refers to a heteroaromatic ring system that contains 2-10 carbon atoms and 1-4 heteroatom groups selected from N, NH, NR', O and S wherein R' is C$_{1-6}$ alkyl and includes aromatic 5 to 6-membered monocyclic heteroaryls and aromatic 7 to 11-membered heteroaryl bicyclic or fused rings where at least one of the rings is aromatic Non-limiting examples of 5 to 6-membered monocyclic heteroaryl rings include furanyl, oxazolyl, isoxazolyl, oxadiazolyl, pyranyl, thiazolyl, pyrazolyl, pyrrolyl, imidazolyl, tetrazolyl, triazolyl, thienyl, thiadiazolyl, pyridinyl, pyrimidinyl, pyridazinyl, pyrazinyl, triazinyl, and purinyl. Non-limiting examples of 7 to 11-membered heteroaryl bicyclic or fused rings include benzimidazolyl, 1,3-dihydrobenzoimidazol-2-one, quinolinyl, dihydro-2H-quinolinyl, isoquinolinyl, quinazolinyl, indazolyl, thieno[2,3-d]pyrimidinyl, indolyl, isoindolyl, indazolyl, benzotriazolyl, benzofuranyl, benzopyranyl, benzodioxolyl, benzoxazolyl, benzothiazolyl, pyrrolo[2,3-b]pyridinyl, and imidazo[4,5-b]pyridinyl. Sulfur and nitrogen may optionally be present in all the possible oxidation stages (sulphur→sulphoxide —SO—, sulphone —SO$_2$—; nitrogen→N-oxide).

The compounds of the invention are only those which are contemplated to be chemically stable as will be appreciated by those skilled in the art. For example, a compound which would have a "dangling valency", or a carbanion are not compounds contemplated by the inventive methods disclosed herein.

Unless specifically indicated, throughout the specification and appended claims, a given chemical formula or name shall encompass tautomers and all stereo, optical and geometrical isomers (e.g. enantiomers, diastereomers, E/Z isomers, etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof. The compounds and salts of the invention can exist in unsolvated as well as solvated forms with pharmaceutically acceptable solvents such as water, ethanol and the like. The phrase "pharmaceutically acceptable" is employed herein to refer to those compounds, materials, compositions, and/or dosage forms which are, within the scope of sound medical judgement, suitable for use in contact with the tissues of human beings and animals without excessive toxicity, irritation, allergic response, or other problem or complication, and commensurate with a reasonable benefit/risk ratio Pharmaceutically acceptable salts include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts.

Further pharmaceutically acceptable salts can be formed with cations from metals like aluminium, calcium, lithium, magnesium, potassium, sodium, zinc and the like (also see Pharmaceutical salts, Birge, S. M. et al., J. Pharm. Sci., (1977), 66, 1-19).

The pharmaceutically acceptable salts of the present invention can be synthesised from the parent compound which contains a basic or acidic moiety by conventional chemical methods. Generally, such salts can be prepared by reacting the free acid or base form of these compounds with a sufficient amount of the appropriate base or acid in water or in an organic diluent like ether, ethyl acetate, ethanol, isopropanol, or acetonitrile, or a mixture thereof.

By a therapeutically effective amount for the purposes of this invention is meant a quantity of substance that is capable of obviating symptoms of illness or alleviating these symptoms, or which prolong the survival of a treated patient.

Some abbreviated notations and their structure correspondences are listed below:

In a representation such as for example

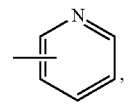

the solid line means that the ring system may be attached to the molecule via the carbon atom 1, 2 or 3, and is thus equivalent to the following representation

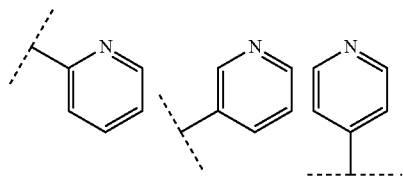

The compounds of formula (I) may be made using the general synthetic methods described below, which also constitute part of the invention.

General Synthetic Methods

The compounds according to the invention may be prepared by the methods of synthesis and synthetic examples described hereinafter in which the substituents of the general formulae have the meanings given hereinbefore. These methods are intended as an illustration of the invention without restricting its subject matter and the scope of the compounds claimed to these examples. Where the preparation of starting compounds is not described, they are commercially obtainable or may be prepared analogously to known compounds or methods described herein. Substances described in the literature are prepared according to the published methods of synthesis.

Compounds of formula I may be prepared from intermediate A' as illustrated in Scheme I.

Scheme I:

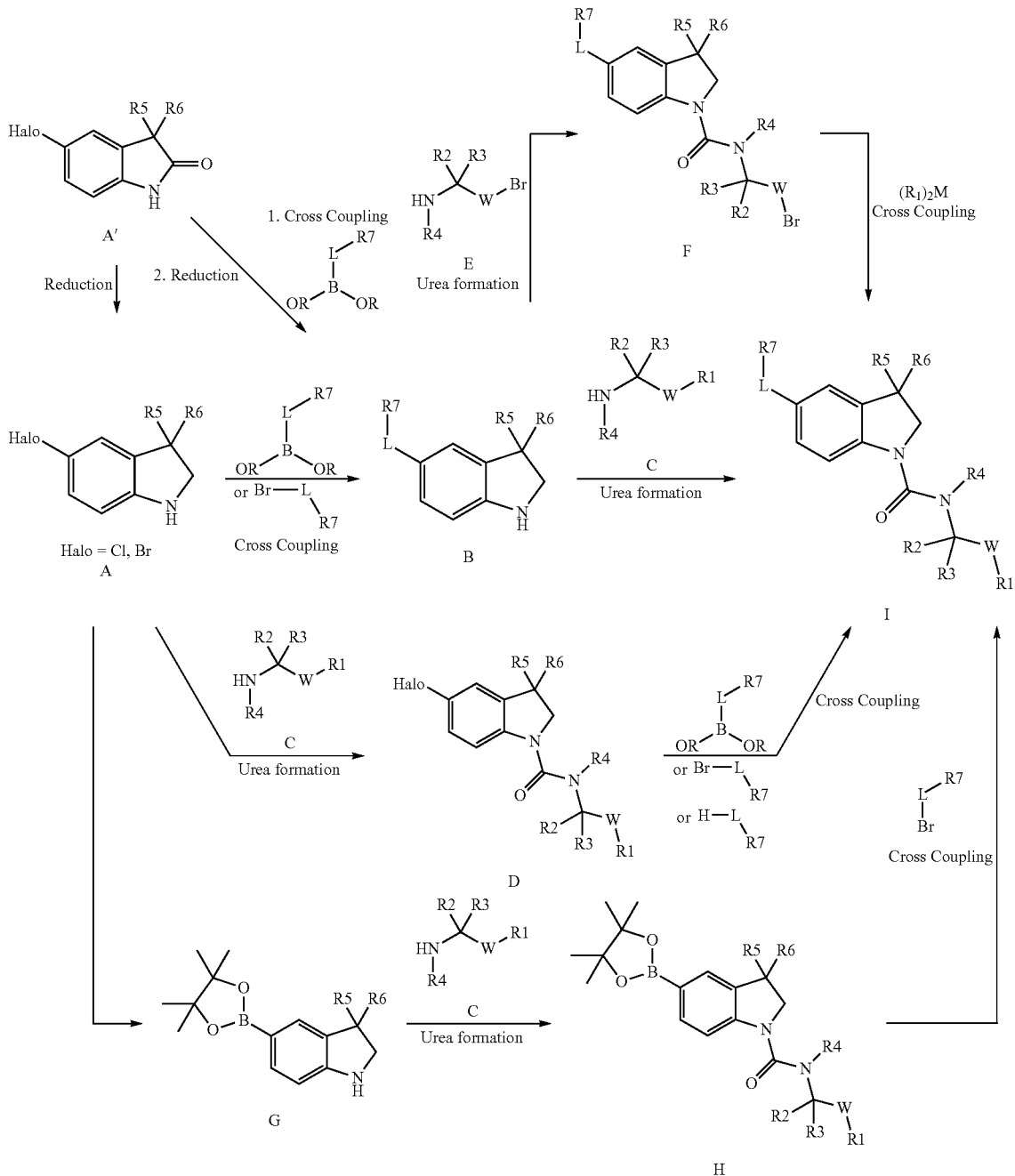

As illustrated above, A is transferred from A' by reduction, then converted into B under cross coupling condition. B could also be formed through cross coupling of A' followed by reduction. B provides I by either urea formation with a suitably functionalized amine C, or a two step procedure which forms intermediate F prior to final cross coupling to install $R_1$-group. A could also be first transformed to D by urea formation. Then D is further elaborated to I by cross coupling. A could also provide G by Miyaura borylation. G is transferred into I by urea formation, then further converted into I by cross coupling. Intermediates A', C, E are either commercially available, readily prepared from commercially available starting materials by methods known in the art or disclosed herein.

Synthetic Examples

Non-limiting examples demonstrating the preparation of the compounds of the invention are provided below. Optimum reaction conditions and reaction times may vary depending on the particular reactants used. Unless otherwise specified, solvents, temperatures, pressures and other reaction conditions may be readily selected by one of ordinary skill in the art. Specific procedures are provided in the Synthetic Examples section. Intermediates and products may be purified by chromatography on silica gel, recrystallization and/or reverse phase HPLC (RHPLC). Discrete enantiomers may be obtained by resolution of racemic products using chiral HPLC. RHPLC purification methods used anywhere from 0-100% acetonitrile in water containing 0.1% formic acid or 0.1% TFA and used one of the following columns:

a) Waters Sunfire OBD C18 5 μM 30×150 mm column
b) Waters XBridge OBD C18 5 μM 30×150 mm column
c) Waters ODB C8 5 μM 19×150 mm column.
d) Waters Atlantis ODB C18 5 μM 19×50 mm column.
e) Waters Atlantis T3 OBD 5 μM 30×100 mm column
f) Phenomenex Gemini Axia C18 5 μM 30×100 mm column HPLC Methods:
Analytical LC/MS Analysis Method A:
Column: Thermo Scientific, Aquasil C18, 50×2.1 mm, 5 μm column
Gradient:

| Time (min) | 0.1% Formic Acid in Water | 0.1% Formic Acid in ACN | Flow (ml/min) |
|---|---|---|---|
| 0 | 90 | 10 | 0.5 |
| 0.5 | 90 | 10 | 0.5 |
| 1.5 | 1 | 99 | 0.5 |
| 2.5 | 1 | 99 | 0.5 |
| 3.3 | 90 | 10 | 0.5 |
| 4.0 | 90 | 10 | 0.5 |

Analytical LC/MS Analysis Method B:
Column: Waters BEH 2.1×50 mm C18 1.7 um column
Gradient:

| Time (min) | 95% Water/5% ACN (0.05% TFA) | ACN (0.05% TFA) | Flow (ml/min) |
|---|---|---|---|
| 0 | 90 | 10 | 0.8 |
| 1.19 | 0 | 100 | 0.8 |
| 1.7 | 0 | 100 | 0.8 |

Analytical LC/MS Analysis Method C:
Column: Thermo Scientific, Aquasil C18, 50×2.1 mm, 5μ, part number 77505-052130, or equivalent
Left and Right Temperature: 35° C.
Run Time: 4.0 min
Gradient:

| Total Time (min) | Flow Rate (uL/min) | 0.1% Formic Acid in Water | 0.1% Formic Acid in Acetonitrile |
|---|---|---|---|
| 0 | 500 | 90.0 | 10.0 |
| 0.5 | 500 | 90.0 | 10.0 |
| 1.5 | 500 | 1.0 | 99.0 |
| 2.5 | 500 | 1.0 | 99.0 |
| 3.3 | 500 | 90.0 | 10.0 |
| 4.0 | 500 | 90.0 | 10.0 |

Analytical LC/MS Analysis Method D:
Column: Phenomex Luna 3u C18(2) 100 A, 50×2.00 mm
Left and Right Temperature: 35° C.
Run Time: 4.0 min
Gradient:

| Total Time (min) | Flow Rate (uL/min) | 0.1% Formic Acid in Water | 0.1% Formic Acid in Acetonitrile |
|---|---|---|---|
| 0 | 500 | 90.0 | 10.0 |
| 0.5 | 500 | 90.0 | 10.0 |
| 1.5 | 500 | 1.0 | 99.0 |
| 2.5 | 500 | 1.0 | 99.0 |
| 3.3 | 500 | 90.0 | 10.0 |
| 4.0 | 500 | 90.0 | 10.0 |

List of Abbreviations Used in Synthetic Examples

| | |
|---|---|
| Ac | Acetyl |
| ACN | Acetonitrile |
| AIBN | Azobisisobutyronitrile |
| aq | Aqueous |
| ATP | adenosine triphosphate |
| Bn | Benzyl |
| Bu | Butyl |
| Boc | tert-butyloxycarbonyl |
| cat | Catalyst |
| conc | concentrated |
| d | day(s) |
| TLC | thin layer chromatography |
| DIEA | N,N-diisopropylethylamine |
| DMAP | 4-N,N-dimethylaminopyridine |
| DME | 1,2-dimethoxyethane |
| DMF | N,N-dimethylformamide |
| DMSO | Dimethylsulphoxide |
| dppf | 1,1'-bis(diphenylphosphino)ferrocene |
| EDC | 1-Ethyl-3-(3-dimethylaminopropyl)carbodiimide |
| ESI | electron spray ionization |
| Et | Ethyl |
| Et$_2$O | diethyl ether |
| EtOAc | ethyl acetate |
| EtOH | Ethanol |
| h | hour(s) |
| HATU | O-(7-azabenzotriazol-1-yl)-N,N,N',N'-tetramethyl-uronium hexafluorophosphate |
| Hep | Heptane |
| HPLC | high performance liquid chromatography |
| i | Iso |
| LC | liquid chromatography |
| LiHMDS | lithium bis(trimethylsilyl)amide |
| sln. | Solution |
| mCPBA | 3-Chloroperoxbenzoic acid |
| Me | Methyl |
| MeOH | Methanol |
| min | Minutes |
| MPLC | medium pressure liquid chromatography |
| MS | mass spectrometry |
| NBS | N-bromo-succinimide |
| NIS | N-iodo-succinimide |
| NMM | N-methylmorpholine |
| NMP | N-methylpyrrolidone |
| NP | normal phase |
| n.a. | not available |
| PBS | phosphate-buffered saline |
| Ph | Phenyl |
| Pr | Propyl |
| Pyr | Pyridine |
| rac | Racemic |
| Rf (R$_f$) | retention factor |
| RP | reversed phase |
| RT | Retention time (HPLC) |
| rt | ambient temperature |
| TBAF | tetrabutylammonium fluoride |
| TBDMS | tert-butyldimethylsilyl |
| TBME | tert-butylmethylether |
| TBTU | O-(benzotriazol-1-yl)-N,N,N',N'-tetramethyl-uronium tetrafluoroborate |
| tBu | tent-butyl |
| TEA | Triethylamine |
| temp. | Temperature |
| tert | Tertiary |
| Tf | Triflate |

-continued

| | |
|---|---|
| TFA | trifluoroacetic acid |
| THF | Tetrahydrofuran |
| TMS | Trimethylsilyl |
| TRIS | tris(hydroxymethyl)-aminomethane |
| Ts | p-Tosyl |
| TsOH | p-toluenesulphonic acid |
| UV | Ultraviolet |
| Xphos | 2-Dicyclohexylphosphino-2',4',6'-triisopropylbiphenyl |

Method 1:
Synthesis of Intermediate A & B

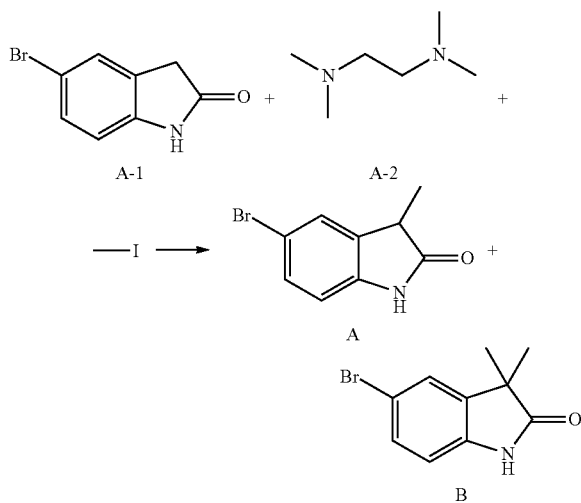

To a solution of A-1 (3.0 g, 14.1 mmol) in THF (90 mL) is added A-2 (4.93 g, 42.4 mmol), and the resulting solution is cooled to −78° C. nBuLi (2.5 M in hexane, 12.4 mL, 31.1 mmol) is added dropwisely and the resulting solution is stirred for 30 min at −78° C. A-3 (1.06 mL, 16.9 mmol) is added dropwisely and the solution is slowly warmed up to −20° C. and stirred for 1 h. The reaction is quenched with saturated aqueous NH$_4$Cl (20 mL) and extracted with EtOAc (50 mL). Phases are separated, and organic layer is washed with water (20 mL) and brine (20 mL). Organic layer is separated and dried over anhydrous Na$_2$SO$_4$, filtered and concentrated. The residue is purified by column chromatography on silica gel (3-40% EtOAc/Heptane) to yield A MS (ES+): m/z 227.4 [M+H]$^+$ and B MS (ES+): m/z 241.2 [M+H]$^+$.

Method 2:
Synthesis of Intermediate C

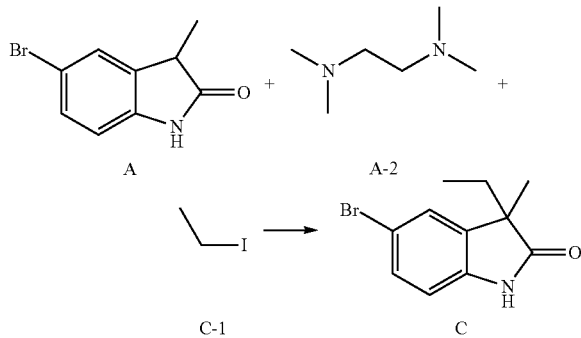

To a solution of A (0.5 g, 2.21 mmol) in THF (20 mL) is added A-2 (0.77 g, 6.63 mml), and the resulting solution is cooled to −78° C. nBuLi (2.5 M in hexane, 1.95 mL, 4.87 mmol)) is added dropwisely and the resulting solution is stirred for 30 min at −78° C. C-1 (0.52 g, 3.32 mmol) is added dropwisely and the solution is slowly warmed up to −20° C. and stirred for 1 h. Then the reaction is warmed up to room temperature for 1 h. The reaction is quenched with saturated aqueous NH$_4$Cl (10 mL) and extracted with EtOAc (20 mL). Phases are separated, and organic layer is washed with water (10 mL) and brine (10 mL). Organic layer is separated and dried over anhydrous Na$_2$SO$_4$, filtered and concentrated. The residue is purified by column chromatography on silica gel (3-40% EtOAc/Heptane) to yield Intermediate C. MS (ES+): m/z 255.2 [M+H]$^+$.

The following intermediate was prepared in similar fashion:

| Structure | Intermediate | HPLC Method | m/z [M + H]$^+$ |
|---|---|---|---|
| (structure) | D | A | 283.4 |
| (structure) | E | | N/A |

Method 3:
Synthesis of Intermediate F

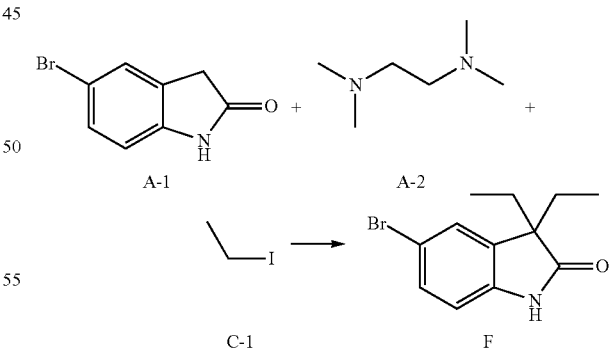

To a solution of A-1 (1.0 g, 5 mmol) in THF (30 mL) is added dropwisely nBuLi (2.5 M in hexane, 6 mL, 16 mmol) at −10° C. The resulting solution is stirred for 30 min at −10° C. A-2 (1.9 g, 16 mmol) and C-1 (2.5 g, 16 mmol) are added and the solution is slowly warmed up to room temperature overnight. The reaction is concentrated. The residue is purified by column chromatography on silica gel to yield F. MS (ES+): m/z 269.9 [M+H]$^+$.

Method 4:
Synthesis of Intermediate G

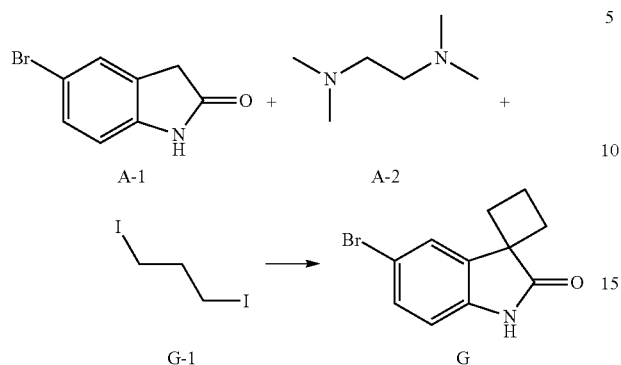

To a solution of A-1 (0.25 g, 1.18 mmol) in THF (25 mL) is added dropwisely nBuLi (2.5 M in hexane, 0.4 mL, 4.0 mmol) at −10° C. The resulting solution is stirred for 30 min at −10° C. A-2 (0.58 mL, 4 mmol) and G-1 (0.13 mL, 01.17 mmol) are added and the solution is slowly warmed up to room temperature overnight. The reaction is concentrated. The residue is purified by column chromatography on silica gel to yield G. MS (ES+): m/z 253.9 [M+H]$^+$.

Method 5:
Synthesis of Intermediate H

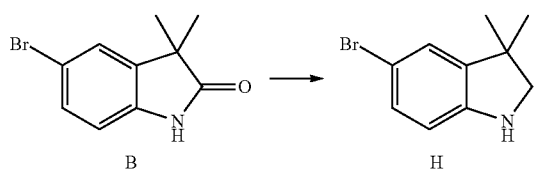

A mixture of B (344 mg, 1.43 mmol) and BH$_3$ (1M solution in THF, 28.6 mL, 28.6 mmol) is stirred at 50° C. for 2 h. The reaction is cooled to 0° C., and diluted with MeOH (3 mL) slowly, followed by addition of HCl (12N, 0.8 mL). The resulting mixture is stirred at room temperature for 1 h. Adjust pH to 8-9 with 10% aqueous NaOH. The resulting mixture is extracted with EtOAc (3×50 mL). Phases are separated, and organic layer is washed with water (20 mL) and brine (20 mL), Organic layer is separated and dried over anhydrous Na$_2$SO$_4$, filtered and concentrated. The residue is purified by column chromatography on silica gel (5-40% EtOAc/Heptane) to yield Intermediate H. MS (ES+): m/z 227.5 [M+H]$^+$.

The following intermediate was prepared in similar fashion:

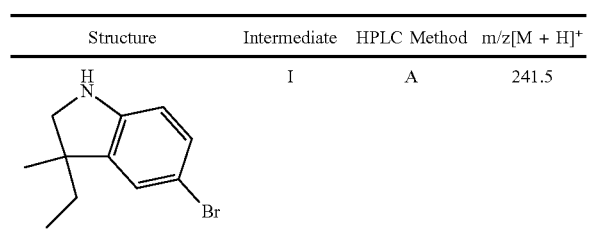

| Structure | Intermediate | HPLC Method | m/z[M + H]$^+$ |
|---|---|---|---|
| (see above) | I | A | 241.5 |
| (see below) | J | A | 255.1 |
| (see below) | K | A | 239.9 |

Method 6:
Synthesis of Intermediate L

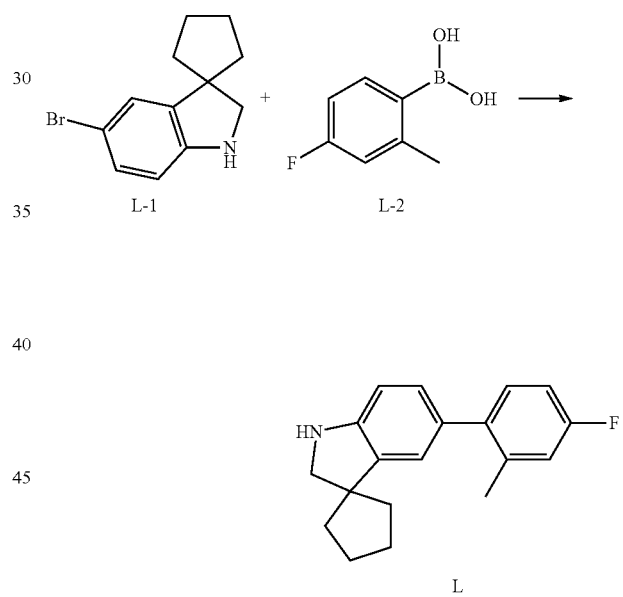

To a solution of L-1 (800 mg, 3.17 mmol), L-2 (732 mg, 4.76 mmol) and aqueous Na$_2$CO$_3$ (2M, 6.3 mL, 12.7 mmol) in DMF (24 mL) is added dichloropalladium 4-ditert-butyl-phosphanyl-N,N-dimethyl-aniline (224 mg, 0.32 mmol). The reaction vial is sealed and heated to 100° C. for 30 min at Biotage microwave reactor. The resulting mixture is diluted with water (10 mL) and ethyl acetate (30 mL). Phases are separated and organics is washed with brine (20 mL). Organic layer is separated and dried over anhydrous Na$_2$SO$_4$, filtered and concentrated. The residue is purified by column chromatography on silica gel (10-50% EtOAc/Heptane) to yield Intermediate L. MS (ES+): m/z 282.0 [M+H]$^+$.

The following intermediate was prepared in similar fashion:

| Structure | Intermediate | HPLC Method | m/z [M + H]+ |
|---|---|---|---|
| 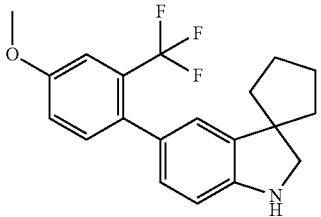 [SMILES: COc1ccc(-c2ccc3c(c2)C2(CCCC2)CN3)c(C(F)(F)F)c1] | M | A | 349.3 |

Method 7:
Synthesis of Intermediate N

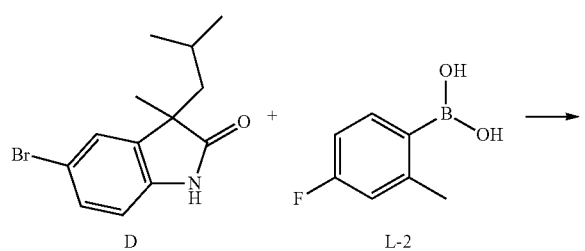

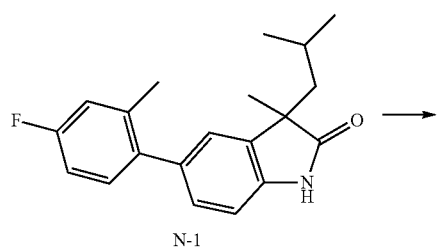

Intermediate N-1 is synthesized from intermediate D and L-2 according to Method 6 described for the synthesis of intermediate L from L-1 and L-2.

Intermediate N is synthesized from intermediate N-1 according to Method 5 described for the synthesis of intermediate H from intermediate B. MS (ES+): m/z 298.1 [M+H]+.

The following intermediate was prepared in similar fashion:

| Structure | Intermediate | HPLC Method | m/z [M + H]+ |
|---|---|---|---|
| (structure with ethyl-substituted indoline) | O | A | 283.8 |
| (spirocyclohexyl indoline structure) | P | A | 281.9 |

Method 8:
Synthesis of Intermediate Q

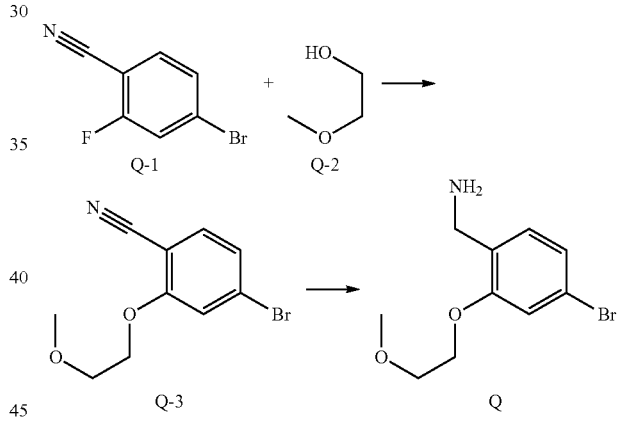

A mixture of Q-1 (1.5 g, 7.50 mmol), Q-2 (5.7 g, 74.9 mmol) and potassium carbonate (1.55 g, 11.3 mmol) in DMF (35 mL) is stirred at room temperature for 12. The reaction mixture is quenched with water (10 mL).). The resulting mixture is extracted with EtOAc (80 mL). Phases are separated, and organic layer is washed with water (20 mL) and brine (20 mL). Organic layer is separated and dried over anhydrous $Na_2SO_4$, filtered and concentrated to yield intermediate Q-3.

A mixture of intermediate Q-3 (0.5 g, 1.87 mmol) and $BH_3$ (1M solution in THF, 5.8 mL, 5.8 mmol) is stirred at 80° C. for 16 h. The reaction is carefully quenched with MeOH (5 mL), and concentrated. The crude product is purified by reverse phase HPLC (10-100% MeCN in water with 0.1% trifluoroacetic acid) and converted to free base form with PL-$HCO_3$ MP SPE to yield title intermediate Q. MS (ES+): m/z 260.9 [M+H]+.

The following intermediates were prepared in a similar manner

| Structure | Intermediate | HPLC Method | m/z[M + H]+ |
|---|---|---|---|
| 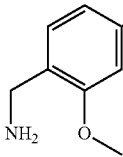 | R | A | 216.9 |

Method 9:
Synthesis of Intermediate S

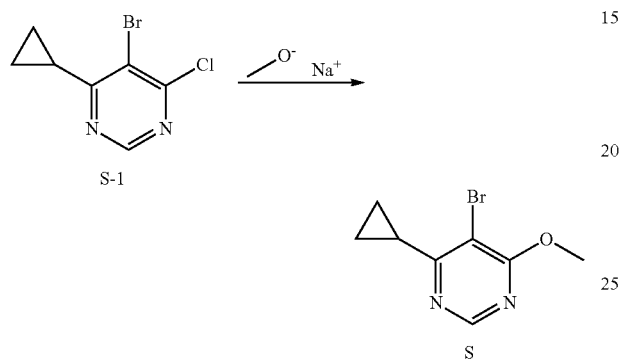

To a solution of S-1 (300 mg, 1.29 mmol) in anhydrous MeOH (15 mL) is added NaOMe (208 mg, 3.86 mmol). The mixture is stirred at room temperature for 1 h. The solution is filtered and concentrated. The residue is purified on SiO$_2$ (using a solvent gradient from 5% EtOAc in Heptane to 30% EtOAc in Heptane) to intermediate S. MS (ES+): m/z 230.8 [M+H]+.

The following intermediates were prepared in a similar manner

| Structure | Intermediate | HPLC Method | m/z [M + H]+ |
|---|---|---|---|
| 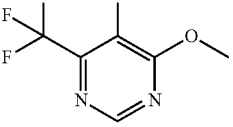 | T | A | 258.9 |

Method 10:
Synthesis of Intermediate U

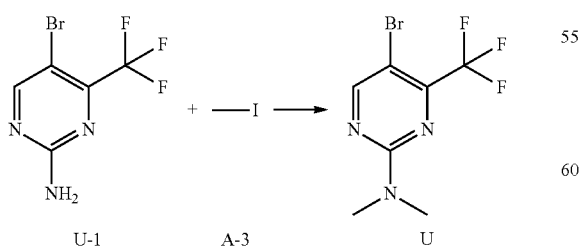

To a solution of U-1 (200 mg, 0.82 mmol) in DMF (4 mL) is added NaH (60 wt %, 99 mg, 2.47 mmol) at room temperature. The reaction is stirred for 15 min, A-3 (351 mg, 2.47 mmol) is added and stirred at room temperature overnight. The reaction is quenched with water (1 mL), and extracted with EtOAc (2×10 mL). Phases are separated, and organic layer is separated and dried over anhydrous Na$_2$SO$_4$, filtered and concentrated. The residue is purified by column chromatography on silica gel (5-20% EtOAc/Heptane) to yield Intermediate U. MS (ES+): m/z 270.9 [M+H]+.

Method 11:
Synthesis of Intermediate V

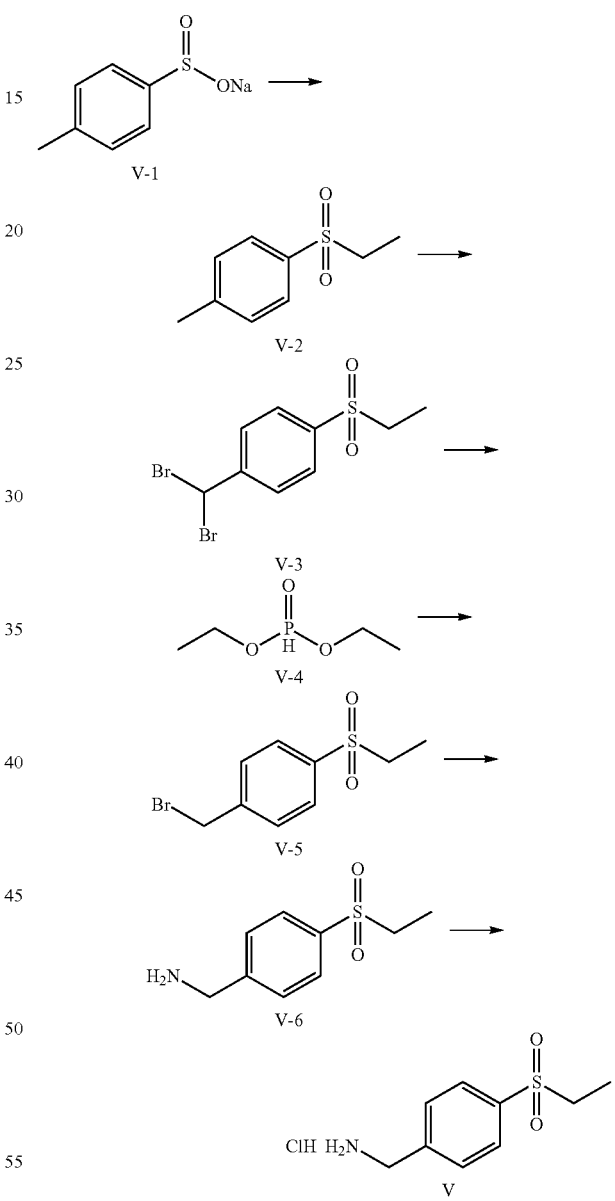

A mixture of intermediate V-1 (100 g, 561 mmol), EtI (131 g, 842 mmol) and TBAB (18 g, 56 mmol) in H$_2$O (200 mL), acetone (150 mL) and of toluene (150 mL) is stirred in sealed vessel at 80° C. overnight. The mixture is partitioned between H$_2$O and EtOAc. The organic layer is dried and concentrated. The residue is purified by silica gel column (PE: EA=20:1) to afford intermediate V-2.

A mixture of compound V-2 (200 g, 1.09 mol), NBS (425.02 g, 2.39 mol) and AIBN (17.82 g, 108.54 mmol) in CCl$_4$ (1400 mL) is stirred at reflux overnight. The mixture is partitioned between H$_2$O and DCM. The organic layer is dried over Na$_2$SO$_4$ and evaporated to afford intermediate V-3.

To a solution of intermediate V-3 (333 g, 974 mmol) and DIPEA (129 g, 1 mol) in ACN (500 mL) is added V-4 (138 g, 1 mol) in ACN (150 mL) dropwise at 0° C., then the mixture is stirred for 5 h. The reaction mixture is concentrated. The residue is recrystallized from MeOH to afford intermediate V-5.

A solution of intermediate V-5 (50 g, 190 mmol) in MeOH (200 mL) is added into a solution of NH$_3$/MeOH (800 mL) at −78° C. The reaction mixture is stirred at r.t overnight. The reaction mixture is concentrated. The residue is re-crystallized from EA to afford intermediate V-6.

A solution of intermediate V-6 (50 g, 250.9 mmol) in HCl/MeOH (250 mL) is stirred at rt overnight. The reaction mixture is concentrated to afford V as a HCl salt.

Method 12:
Synthesis of Intermediate W

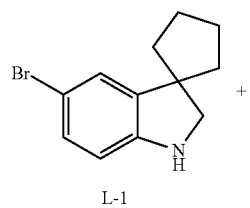
L-1

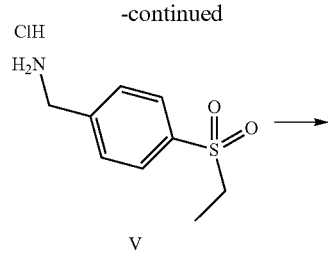
V

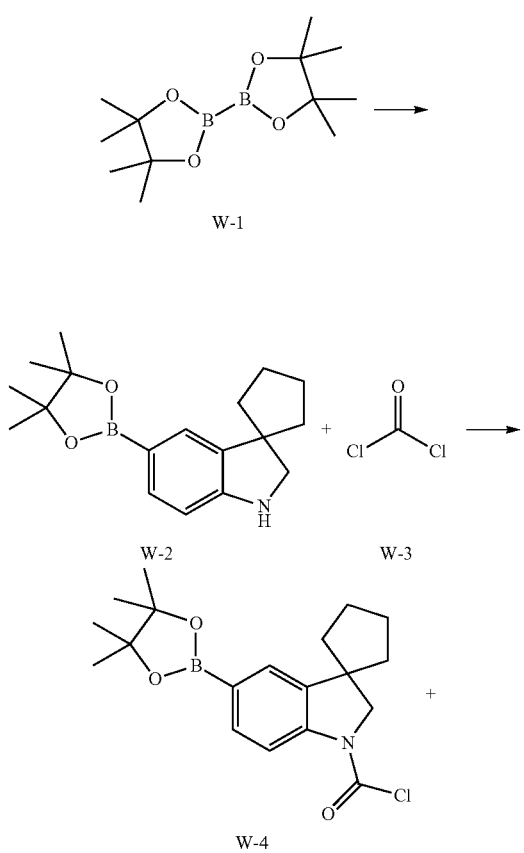

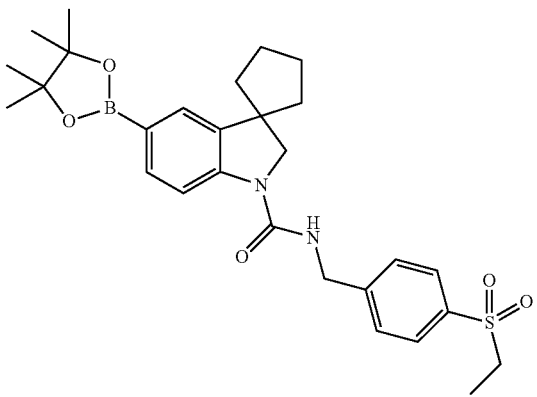
W

A solution of L-1 (4.0 g, 15.8 mmol), W-1 (8.0 g, 31.7 mmol), KOAc (4.6 g, 47.5 mmol) and PdCl$_2$(dppf)DCM (647 mg, 0.79 mmol) in DMF (100 mL) is heated at 80° C. overnight. The resulting mixture is diluted with water (100 mL) and EtOAc (400 mL). Phases are separated, and organic layer is washed with water (100 mL) and brine (100 mL). Organic layer is separated and dried over anhydrous Na$_2$SO$_4$, filtered and concentrated. The residue is purified by column chromatography on silica gel (1-4% MeOH/DCM) to yield Intermediate W-2.

To a solution of intermediate W-2 (1.56 g; 5.21 mmol) in DCM (50 mL) is added saturated aqueous NaHCO$_3$ (50 mL) solution followed by W-3 (15% in toluene) (11.6 mL; 16.4 mmol). The reaction mixture is stir at room temperature for 40 min. The reaction is quenched with water (20 mL). Phases are separated, and organic layer dried over anhydrous Na$_2$SO$_4$, filtered and concentrated to yield W-4.

To the W-4 (850 mg; 2.35 mmol) is added a solution of V (680 mg; 3.41 mmol) in acetonitrile (25 ml) followed by Diisopropylethylamine (1.26 ml; 7.05 mmol). The reaction is stirred at room temperature for 2 h. The reaction is concentrated and purified on SiO$_2$ (using a solvent gradient from 1% MeOH in DCM to 10% MeOH in DCM) to yield Intermediate W. MS (ES+): m/z 525.05 [M+H]$^+$.

The following intermediates were prepared in a similar manner

| Structure | Intermediate | HPLC Method | m/z[M + H]+ |
|---|---|---|---|
| 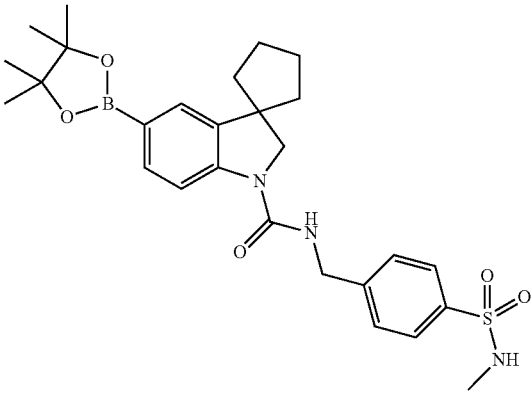 [SMILES: CNS(=O)(=O)c1ccc(CNC(=O)N2CC3(CCCC3)c3cc(B4OC(C)(C)C(C)(C)O4)ccc32)cc1] | X | A | 526.5 |
| 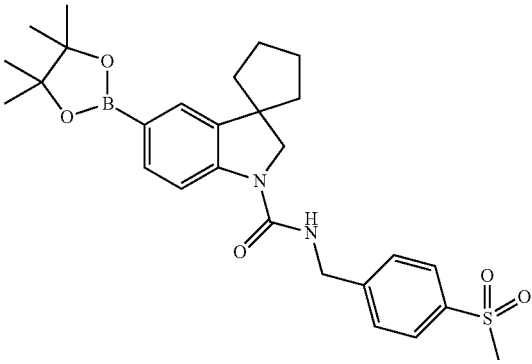 [SMILES: CC1(C)OB(c2ccc3c(c2)C2(CCCC2)CN3C(=O)NCc2ccc(S(C)(=O)=O)cc2)OC1(C)C] | Y | A | 511.2 |

Method 13:

Synthesis of Intermediate Z

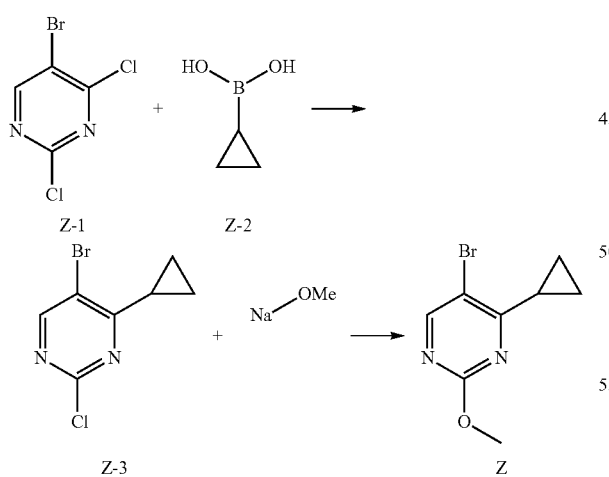

A solution of Z-1 (30 g, 131.6 mmol), Z-2 (11.3 g, 131.6 mmol), K₂CO₃ (54.5 g, 294.8 mmol) and Pd(PPh₃)₄ (5 g) in DMF (60 mL) and Toluene (300 mL) is stirred at 120° C. overnight. The mixture is filtered and the filtrate was evaporated under reduced pressure. The crude product is purified first by silica gel column chromatography and then by p-HPLC to give Intermediate Z-3.

A mixture of Z-3 (3.8 g, 16.3 mmol) and NaOMe (4.4 g, 81.5 mmol) in MeOH (40 mL) is stirred at reflux for 1 h. The mixture is quenched by water and extracted with EtOAc. The organic layer is evaporated under reduced pressure, dried over anhydrous Na₂SO₄ and purified by silica gel column chromatography to give Intermediate Z.

Method 14:

Synthesis of Intermediate AA

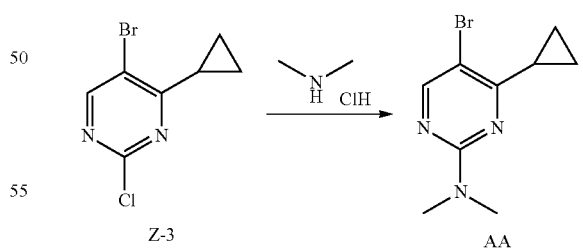

To a solution of dimethylamine hydrochloride (139 mg, 1.71 mmol) in EtOH (4 mL) is added Z-3 (200 mg, 0.85 mmol) followed by diisopropylethylamine (0.54 mL, 3.03 mmol). The vial is sealed with a cap mat and heated to 110° C. for 30 min on Biotage microwave reactor. The resulting mixture is concentrated and purified by column chromatography on silica gel (5-40% EtOAc/Heptane) to yield Intermediate AA. MS (ES+): m/z 242.9 [M+H]+.

Method 15:
Synthesis of Intermediate AB

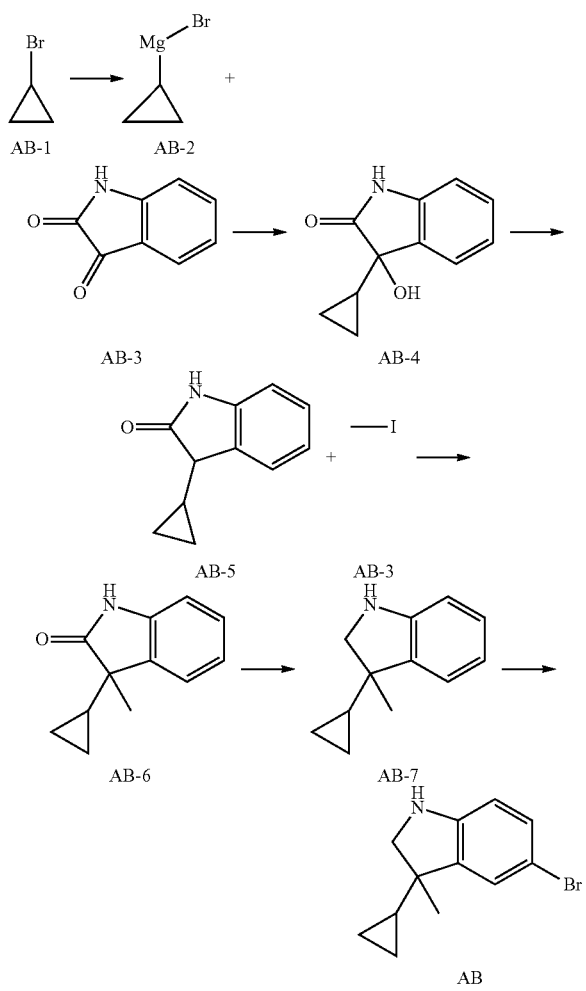

To a mixture of Mg (30.35 g, 1.26 mol) in THF (650 ml) is added AB-1 (170 g, 1.41 mol) slowly at 60° C. over 5 h and stirred until Mg disappeared. The mixture is cooled to room temperature and used directly in the next step as AB-2.

To a mixture of AB-3 (30 g, 0.20 mol) in THF (300 ml) is added AB-2 (800 ml, ~1.60 mol/L) slowly at −78° C. over 1 h and warmed to room temperature. The reaction mixture is stirred at room temperature for 40 h. The mixture is quenched by saturated NH$_4$Cl solution and extracted with EtOAc. The organic layers are dried over anhydrous Na$_2$SO$_4$, evaporated under reduced pressure and purified by silica gel column chromatography to give AB-4.

To a mixture of AB-4 (20 g, 89.85 mmol, 85% purity) is added Et$_3$SiH (31.34 g, 0.27 mol) slowly at −5° C. and TFA (30.73 g, 0.27 mol) at 0° C.~−5° C. slowly. The mixture is stirred at 10° C. for 2 h and then at room temperature for 2 d. The mixture is quenched by NH$_3$.H$_2$O and extracted with EtOAc. The organic layers are dried over anhydrous Na$_2$SO$_4$, evaporated under reduced pressure and purified by silica gel column chromatography to give AB-5.

To a solution of AB-5 (5 g, 25 mmol, 85% purity) in DMF (50 ml) is added NaH (0.98 g, 24.54 mmol) at 0° C. and stirred for at 0° C. 1 h. Then A-3 (3.48 g, 24.54 mmol) is added to the mixture at 0° C. and the reaction mixture was stirred at room temperature for 2 h. The mixture is quenched by saturated NH$_4$Cl solution and extracted with EtOAc. The organic layers are dried over anhydrous Na$_2$SO$_4$, evaporated under reduced pressure and purified by silica gel column chromatography and MPLC to give AB-6.

To a solution of AB-6 (1 g, 5.34 mmol) in THF (10 ml) is added BH$_3$.SMe$_2$ (5.34 ml, 53.4 mmol) at 0° C. and the reaction mixture is stirred at room temperature for 15 h and heated to reflux for 5 h. The mixture is quenched by MeOH and evaporated under reduced pressure. The crude product is purified by silica gel column chromatography to give AB-7.

To a solution of AB-7 (0.48 g, 2.77 mmol) in ACN (6 ml) is added NBS (0.42 g, 2.77 mmol) at 0° C. slowly. Then the reaction mixture is stirred at room temperature for 4 h. The mixture is evaporated under reduced pressure and purified by silica gel column chromatography and p-HPLC to give Intermediate AB.

The following intermediates were prepared in a similar manner

| Structure | Intermediate | HPLC Method | m/z [M + H]$^+$ |
|---|---|---|---|
| 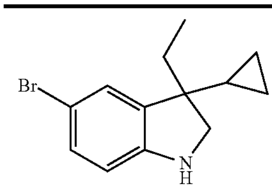 | AC |  | N/A |

Method 16:
Synthesis of Intermediate AD

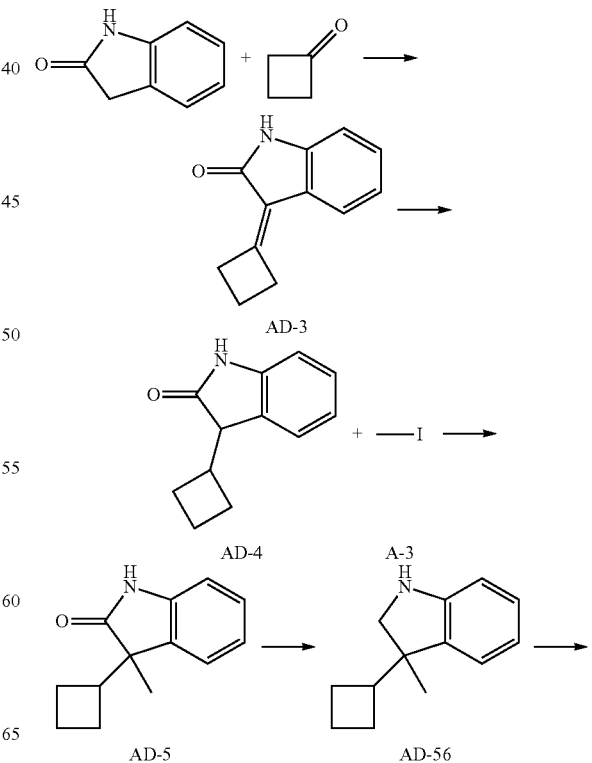

91

-continued

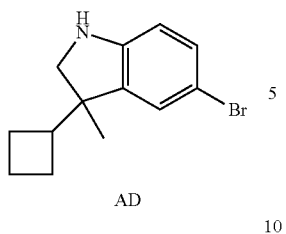

AD

To a solution of AD-1 (20 g, 150.2 mmol) and AD-2 (15.8 g, 225.3 mmol) in EtOH (200 mL) is added Piperidine (6.4 g, 75.1 mmol) under nitrogen at room temperature. The reaction mixture is stirred at room temperature for 4 h. The reaction mixture is quenched by water and extracted with EtOAc. The organic layers are dried over anhydrous Na$_2$SO$_4$, evaporated under reduced pressure and purified by silica gel column chromatography to give AD-3.

A mixture of AD-3 (6.6 g, 35.6 mmol) and Pd—C(2 g) in MeOH (66 mL) is stirred under hydrogen with pressure of 50 psi at room temperature overnight. The reaction mixture was filtered and the filtrate is evaporated under reduced pressure and purified by silica gel column chromatography to give AD-4 (4.2 g, 63% yield).

To a solution of AD-4 (3.7 g, 18.4 mmol) in DMF (37 mL) is added NaH (0.73 g, 18.4 mmol) under nitrogen at 0° C. The mixture was stirred at 0° C. for 0.5 h. Then A-3 (2.34 g, 16.54 mmol) is added to the reaction mixture at 0° C. Then the mixture is stirred at room temperature for 3 h. TLC showed the reaction was completed. The mixture is quenched by NH$_4$Cl solution and extracted with EtOAc. The organic layers are dried over anhydrous Na$_2$SO$_4$, evaporated under reduced pressure give AD-5 which is used in next step.

To a mixture of AD-5 (5.0 g, 24.8 mmol) in THF (50 mL) is added LiAlH$_4$ (1.0 g, 27.3 mmol) under nitrogen at 0° C. The mixture was stirred at room temperature overnight. The mixture is quenched by NH$_4$Cl solution and filtered. The filtrate is extracted with EtOAc. The organic layer is dried over anhydrous Na$_2$SO$_4$, evaporated under reduced pressure and purified by silica gel column chromatography to give AD-6.

To a solution of AD-6 (2.5 g, 13.3 mmol) in CHCl$_3$ (25 mL) is added NBS (2.6 g, 12.7 mmol) under nitrogen at 0° C. The mixture is warmed to room temperature and stirred for 3 h. The mixture is quenched by water and extracted with EtOAc. The organic layer is dried over anhydrous Na$_2$SO$_4$, evaporated under reduced pressure and purified by silica gel column chromatography to give Intermediate AD.

Method 17:

Synthesis of Intermediate AE

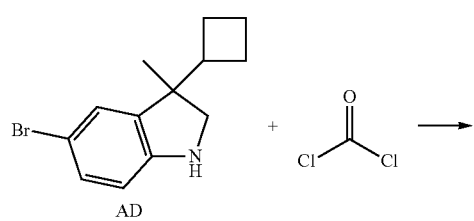

92

-continued

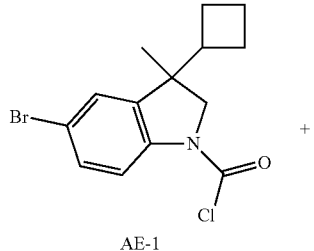

AE-1

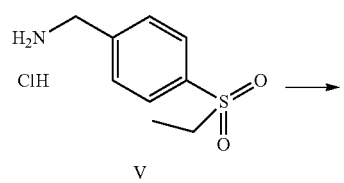

V

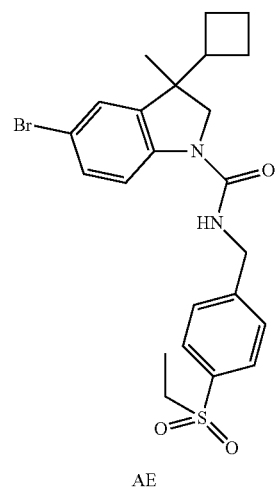

AE

To a solution of intermediate AD (0.30 g; 1.13 mmol) in DCM (10 mL) is added saturated aqueous NaHCO$_3$ (10 mL) solution followed by phosgene (15% in toluene) (2.5 mL; 3.56 mmol). The reaction mixture is stir at room temperature for 40 min. The reaction is quenched with water (20 mL). Phases are separated, and organic layer dried over anhydrous Na$_2$SO$_4$, filtered and concentrated to yield AE-1.

To the AE-1 (0.37 g; 1.13 mmol) is added a solution of V (0.29 g; 1.24 mmol) in acetonitrile (10 ml) followed by Diisopropylethylamine (0.81 ml; 4.51 mmol). The reaction was stirred at room temperature for 30 min. The reaction is concentrated and purified on SiO$_2$ (using a solvent gradient from 0% MeOH in DCM to 4% MeOH in DCM) to yield Intermediate AE. MS (ES+): m/z 492 [M+H]$^+$.

The following compounds were prepared in a similar manner:

Example 52, 54, 55, 59

The following intermediates were prepared in a similar manner

| Structure | Intermediate | HPLC Method | m/z[M + H]+ |
|---|---|---|---|
| 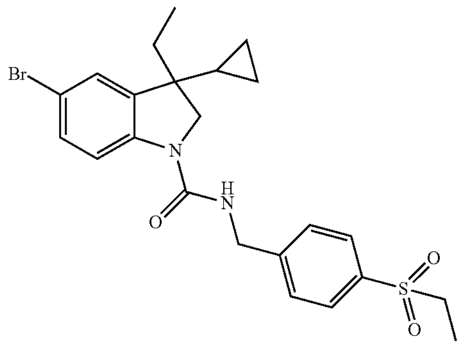 [SMILES: CCC1(C2CC2)CN(C(=O)NCc2ccc(S(=O)(=O)CC)cc2)c2ccc(Br)cc21] | AF | A | 492.0 |
| 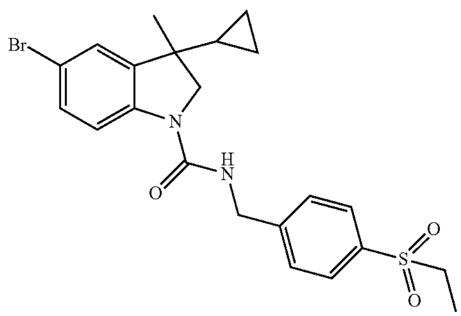 [SMILES: CCS(=O)(=O)c1ccc(CNC(=O)N2CC(C)(C3CC3)c3cc(Br)ccc32)cc1] | AG | | N/A |
| 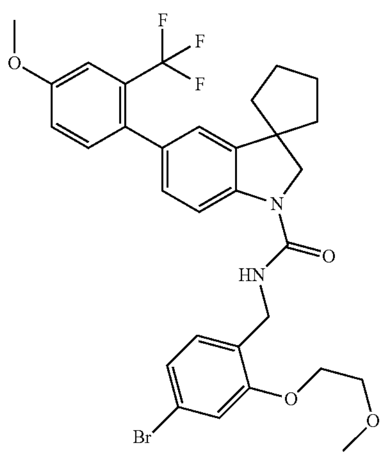 [SMILES: COCCOc1cc(Br)ccc1CNC(=O)N1CC2(CCCC2)c2cc(-c3ccc(OC)cc3C(F)(F)F)ccc21] | AH | A | 534.1 |
| 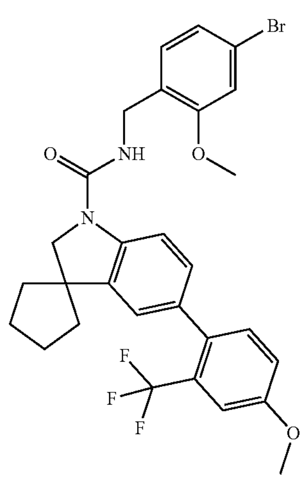 [SMILES: COc1ccc(-c2ccc3c(c2)C2(CCCC2)CN3C(=O)NCc2ccc(Br)cc2OC)c(C(F)(F)F)c1] | AI | A | 590.0 |

-continued
| Structure | Intermediate | HPLC Method | m/z[M + H]⁺ |
|---|---|---|---|
| 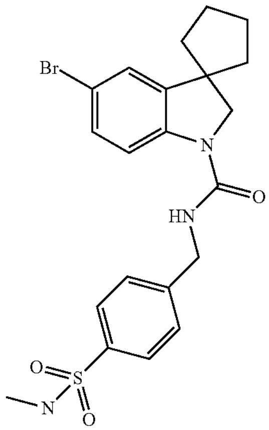 [SMILES: CNS(=O)(=O)c1ccc(CNC(=O)N2CC3(CCCC3)c3cc(Br)ccc32)cc1] | AL | A | 478.1, 480.0 |
| 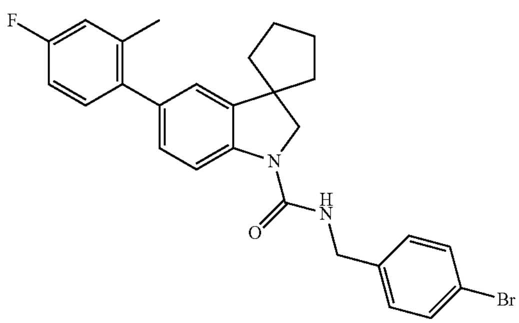 [SMILES: Cc1cc(F)ccc1-c1ccc2c(c1)C1(CCCC1)CN2C(=O)NCc1ccc(Br)cc1] | AM | C | 493.2 |
| 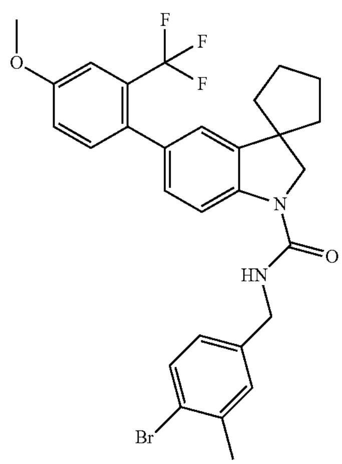 [SMILES: COc1ccc(-c2ccc3c(c2)C2(CCCC2)CN3C(=O)NCc2ccc(Br)c(C)c2)c(C(F)(F)F)c1] | AN | A | 574.0 |
Method 18:
Synthesis of Intermediate AJ
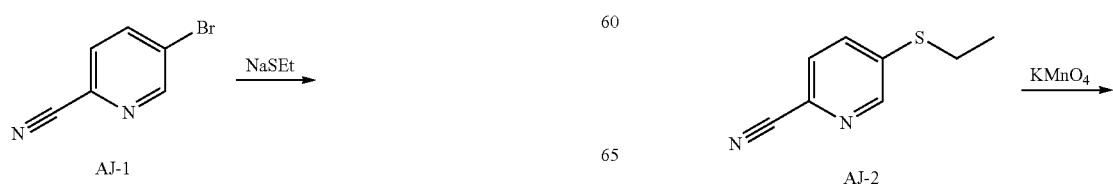
-continued

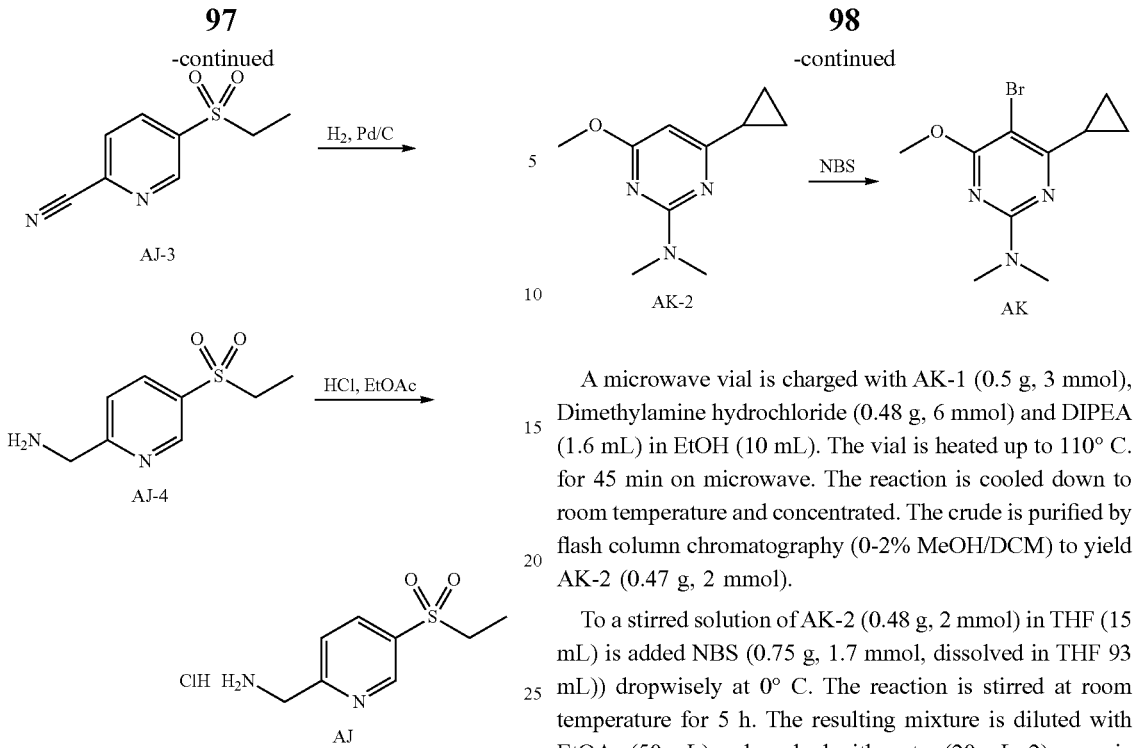

A mixture of AJ-1 (8 g, 43.96 mmol), K₂CO₃ (7.88 g, 57.1 mmol) and sodium ethanethiolate (4.06 g, 48.3 mmol) in NMP (60.0 mL) under nitrogen was stirred at room temperature overnight. The reaction mixture was poured into water and filtered. The precipitate was washed with water and dried under vacuum to yield intermediate AJ-2.

To a suspension of AJ-2 (6 g, 36.6 mmol) in AcOH (2.63 g, 43.8 mmol) was added a solution of KMnO₄ (5.78 g, 36.6 mmol) in H₂O (20.0 ml) dropwise. The reaction mixture was stirred at room temperature for 15 h. The mixture was diluted with water and extracted with EtOAc. The organic layers were dried with anhydrous Na₂SO₄, evaporated under reduced pressure and purified by silica gel column chromatography to yield intermediate AJ-3.

A solution of AJ-3 (3.3 g, 16.8 mmol) and Pd/C (500 mg, 10% on carbon catalyst) in MeOH (30 ml) was stirred at room temperature under H₂ (50 psi) for 8 h. The mixture was filtered and the filtrate was concentrated under reduced pressure to afford intermediate AJ-4.

To a stirred solution of AJ-4 (2.5 g, 12.5 mmol) in EtOAc (30 mL) was added HCl-EtOAc (20.0 ml, 2 M). The solution was stirred at room temperature for 5 h then filtered to yield intermediate AJ. MS (ES+): m/z 201.2 [M+H]⁺.

Method 19:
Synthesis of Intermediate AK

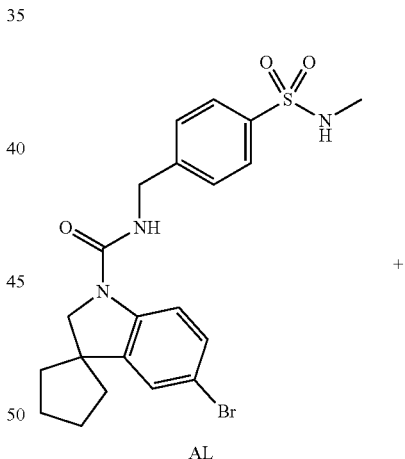

A microwave vial is charged with AK-1 (0.5 g, 3 mmol), Dimethylamine hydrochloride (0.48 g, 6 mmol) and DIPEA (1.6 mL) in EtOH (10 mL). The vial is heated up to 110° C. for 45 min on microwave. The reaction is cooled down to room temperature and concentrated. The crude is purified by flash column chromatography (0-2% MeOH/DCM) to yield AK-2 (0.47 g, 2 mmol).

To a stirred solution of AK-2 (0.48 g, 2 mmol) in THF (15 mL) is added NBS (0.75 g, 1.7 mmol, dissolved in THF 93 mL)) dropwisely at 0° C. The reaction is stirred at room temperature for 5 h. The resulting mixture is diluted with EtOAc (50 mL) and washed with water (20 mL×2), organic layers are dried over anhydrous Na₂SO₄, filtered and concentrated. The crude is purified by flash column chromatography (5% EtOAc/Heptane) to yield AK (0.3 g, 1 mmol).

Method 20:
Synthesis of Example 1

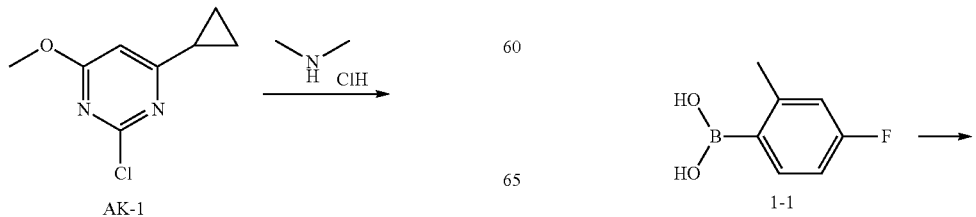

+

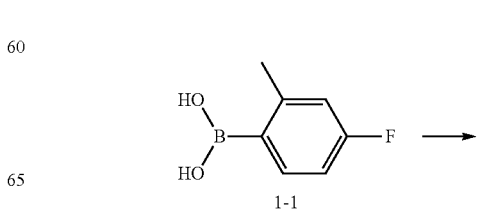

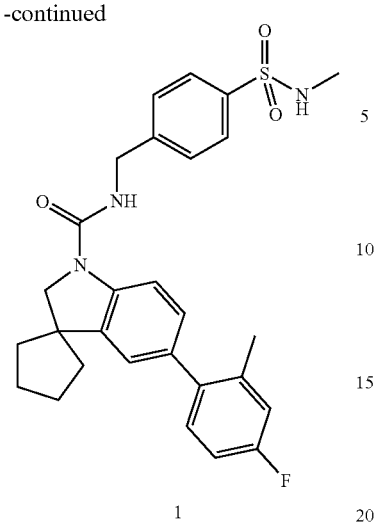

1

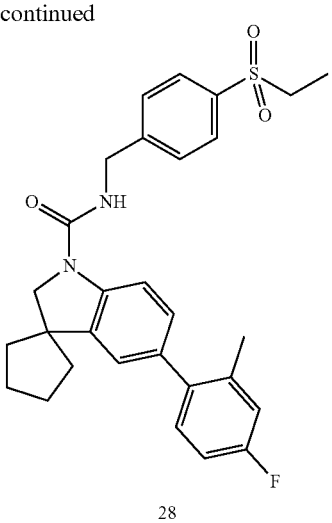

28

To a solution of AL (50 mg, 0.105 mmol) and 1-1 (24 mg, 0.157 mmol) in 1,4-dioxane (2 mL) is added aqueous sodium carbonate (2 M; 0.31 mL, 0.63 mmol) and dichloropalladium 4-ditert-butylphosphanyl-N,N-dimethyl-aniline (29 mg, 0.042 mmol). The resulting mixture is heated to 140° C. for 30 minutes in a Biotage microwave reactor. The mixture is filtered through a Si-thiol palladium-scavenging cartridge, which is rinsed with EtOAc (3 mL). The combined filtrates are concentrated, and the crude product is purified by reverse phase HPLC eluting with 10-100% MeCN in water (+0.1% ammonium bicarbonate) to yield title compound 1. MS (ES+): m/z 508.1 [M+H]$^+$.

**catalyst amount can range from 10-40 mol %; DMF can be used in place of 1,4-dioxane The following compounds were prepared in a similar manner:

Example 2-27, 51, 53, 56-58, 64-67, 71, 75-77, 79-85, 95, 102, 115, -116

Method 21:
Synthesis of Example 28

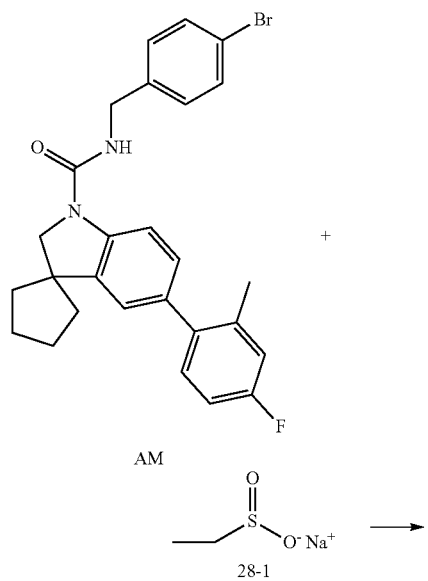

AM

AM (68.0 mg, 0.14 mmol), copper (I) iodide (78.6 mg, 0.41 mmol), and 28-1 (48.0 mg, 0.41 mmol) are dissolved in DMSO (2 mL). The resulting solution is purged with argon and heated at 130° C. for 30 minutes in a Biotage microwave reactor. The mixture is diluted with water (0.5 mL) and filtered through a syringe filter, then concentrated under reduced pressure. The crude product is purified by reverse phase HPLC (25-100% MeCN in water with 0.1% trifluoroacetic acid) and converted to free base form with PL-HCO$_3$ MP SPE to yield title compound 28. MS (ES+): m/z 507.3 [M+H]$^+$.

The following compounds were prepared in a similar manner:

Example 101, 104-105

Method 22:
Synthesis of Example 29

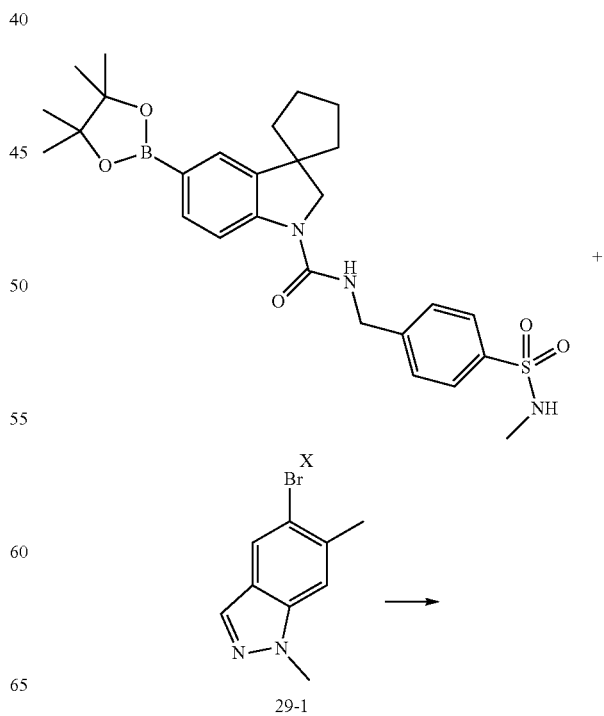

29-1

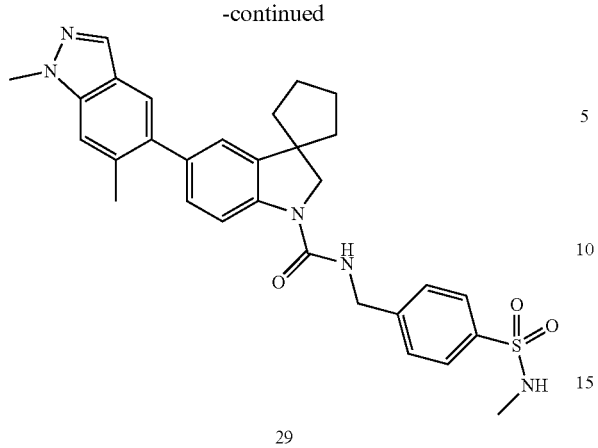

29

To a solution of X (50 mg, 0.095 mmol) and 29-1 (32 mg, 0.14 mmol) in argon-degassed DMF (2 mL) is added aqueous sodium carbonate (2 M; 0.31 mL, 0.63 mmol) and dichloropalladium 4-ditert-butylphosphanyl-N,N-dimethylaniline (15 mg, 0.021 mmol). The resulting mixture is heated to 120° C. for 30 minutes in a Biotage microwave reactor. The mixture is diluted with EtOAc, washed with brine, dried over MgSO4, filtered, and concentrated. The crude product is purified by reverse phase HPLC eluting with 10-100% MeCN in water (+0.1% ammonium bicarbonate) to yield title compound 29. MS (ES+): m/z 544.3 [M+H]$^+$.

**catalyst amount can range from 10-40 mol %

The following compounds were prepared in a similar manner:

Example 30-50, 69-70, 72, 78, 99, 106, 108-110, 112, 114, 119, 121, 122, 130

Method 23:
Synthesis of Example 60

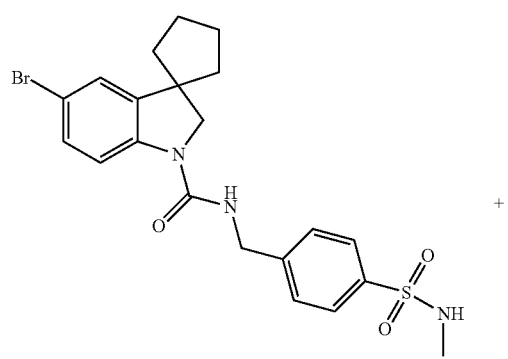

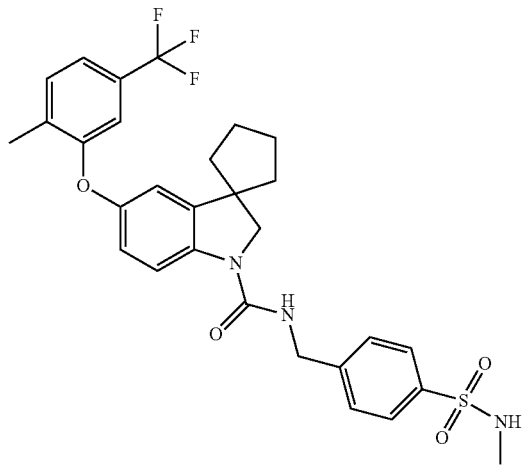

60

AL (80 mg, 0.16 mmol), 60-1 (59 mg, 0.33 mmol), and dimethylglycine (5.2 mg, 0.050 mmol) are dissolved in DMSO (1 mL). The resulting mixture is degassed with argon, and cesium carbonate (54 mg, 0.16 mmol) and copper (I) iodide (3.2 mg, 0.017 mmol) are added. The mixture is heated to 150° C. for 15 h. The mixture is filtered, then a drop of water is added. The mixture is filtered a second time and purified by reverse phase HPLC (5-75% MeCN/water) and converted to free base form with PL-HCO$_3$ MP SPE to yield title compound 60. MS (ES+): m/z 574.3 [M+H]$^+$.

The following compounds were prepared in a similar manner:

Example 61-63

Method 24:
Synthesis of Example 68

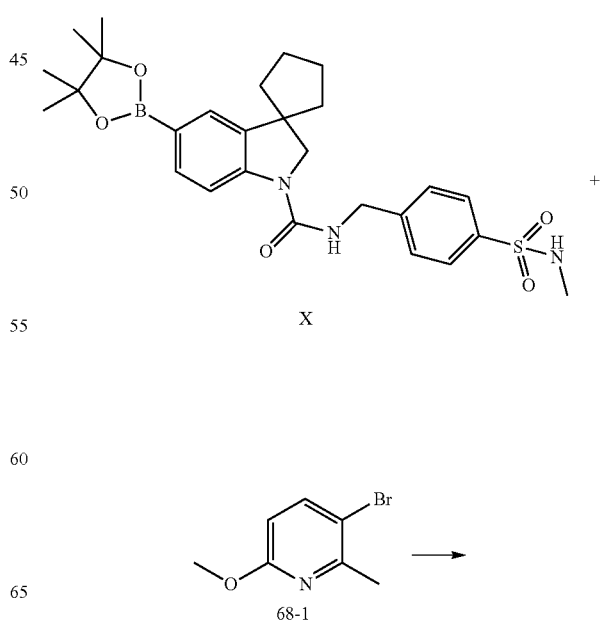

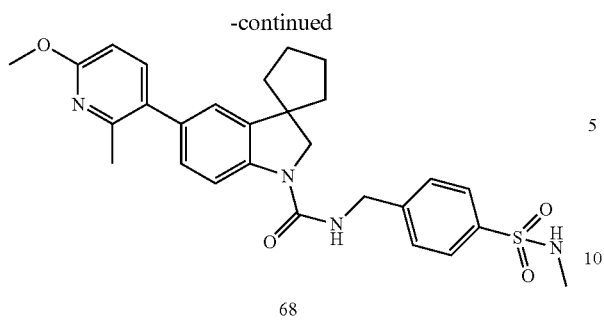

68

To a solution of X (50 mg, 0.095 mmol) and 68-1 (19 mg, 0.095 mmol) in argon-degassed 2-propanol (5 mL) is added aqueous sodium carbonate (2 M; 0.5 mL, 0.95 mmol), dicyclohexyl-(2',4',6'-triisopropyl-biphenyl-2-yl)phosphane (XPhos; 5 mg, 0.010 mmol), and palladium (II) acetate (2.0 mg, 0.010 mmol). The resulting mixture is heated to 100° C. for 2 h in a Biotage microwave reactor. The mixture is filtered through Celite and concentrated. The crude product is purified by reverse phase HPLC (10-100% MeCN/water with 0.1% ammonium bicarbonate) to yield title compound 68. MS (ES+): m/z 521.2 [M+H]$^+$.

The following compounds were prepared in a similar manner:

Example 73-74, 86-94, 98, 107, 111

Method 25:
Synthesis of Example 96

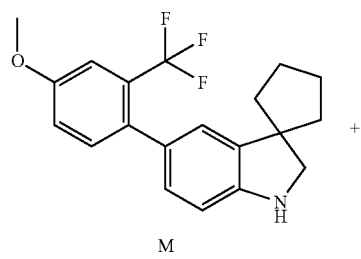

M

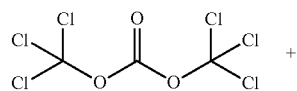

+

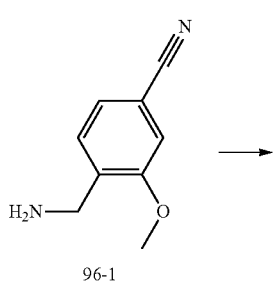

96-1

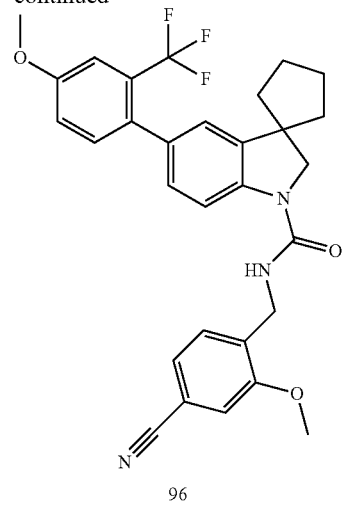

96

To an ice-cold solution of triphosgene (17 mg, 0.058 mmol) in DCM (1 mL) is slowly added a solution of M (50 mg, 0.14 mmol) and diisopropylethylamine (0.06 mL, 0.36 mmol) in DCM (2 mL). The resulting mixture is stirred for 15 min, then a solution of 96-1 (46 mg, 0.28 mmol) and diisopropylethylamine (0.06 mL, 0.36 mmol) in DMF (1 mL) is added dropwise. The mixture is stirred for 5 min and then stirred an additional hour at room temperature. The reaction is quenched with water (1 mL) and concentrated under reduced pressure. The crude product is purified by reverse phase HPLC and converted to free base form with PL-HCO$_3$ MP SPE to yield title to yield title compound 321. MS (ES+): m/z 536.3 [M+H]$^+$.

The following compounds were prepared in a similar manner:

Example 128-129

Method 26:
Synthesis of Example 97

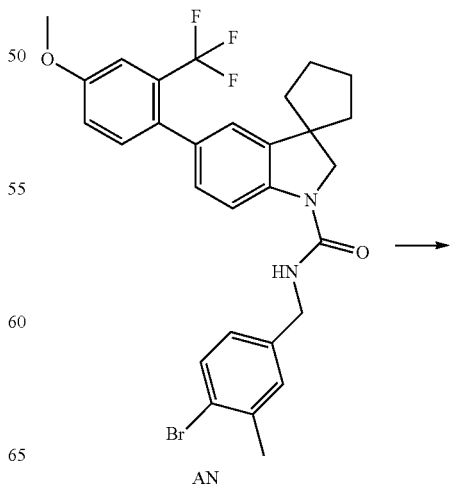

AN

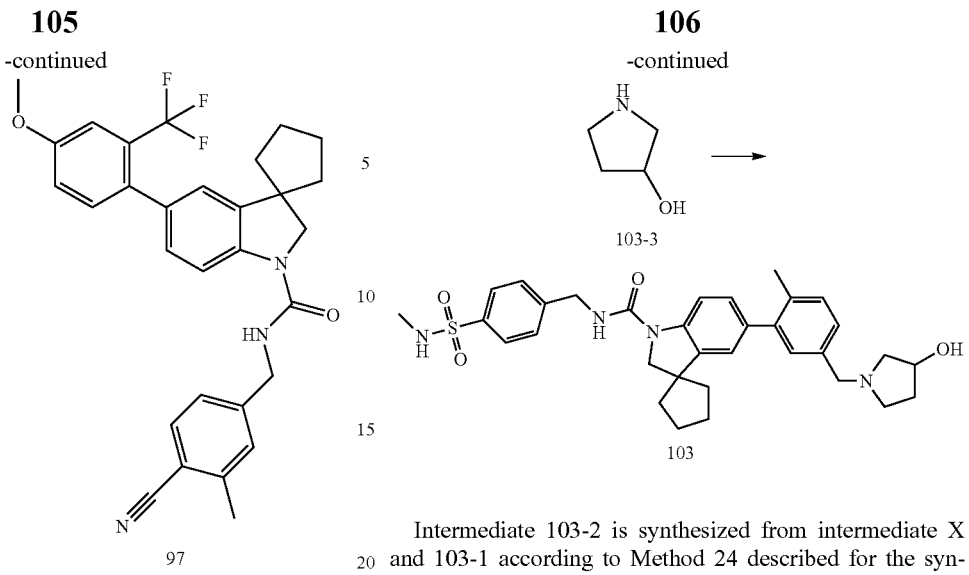

97

To a solution of intermediate AN (50.0 mg, 0.087 mmol) in DMSO (1 mL) is added zinc cyanide (41.0 mg, 0.35 mmol) and tetrakis(triphenylphosphine)palladium (20.2 mg, 0.017 mmol). The resulting mixture is degassed with argon and heated to 120° C. for 40 min in a Biotage microwave reactor. The reaction mixture is filtered and concentrated under reduced pressure. The crude product is purified by reverse phase HPLC and then converted to free base form with PL-HCO₃ MP SPE to yield title compound 97. MS (ES+): m/z 520.2 [M+H]⁺.

The following compounds were prepared in a similar manner:

Example 100

Method 27:
Synthesis of Example 103

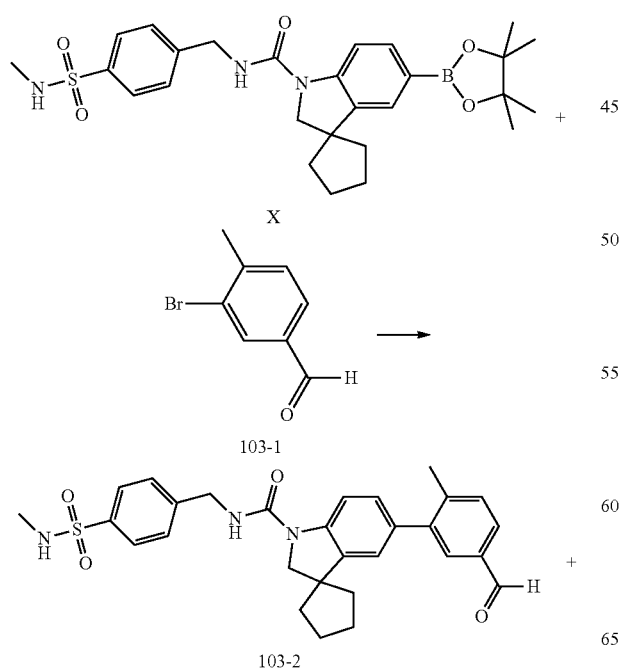

Intermediate 103-2 is synthesized from intermediate X and 103-1 according to Method 24 described for the synthesis of Example 68 from X and 68-1.

To a solution of intermediate 103-2 (50.0 mg, 0.097 mg) in DCM (3 mL) is added 103-3 (8.0 mg, 0.097 mmol), followed by AcOH (0.5 mL). The mixture is stirred for 1 h, then sodium triacetoxyborohydride (20.0 mg, 0.097 mmol) is added. The resulting mixture is stirred overnight. The mixture is filtered and concentrated under reduced pressure. The crude product is purified by reverse phase HPLC and converted to free base form with MP-HCO3 resin to yield title compound 103. MS (ES+): m/z 589.4 [M+H]⁺.

**can be conducted without AcOH

The following compounds were prepared in a similar manner:

Example 123-124

Method 28:
Synthesis of Example 113

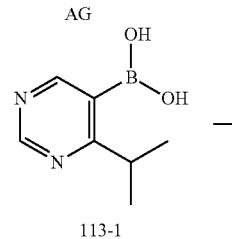

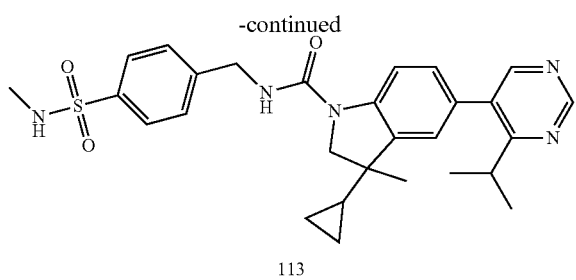

113

To a solution of AG (20 mg, 0.042 mmol) and 113-1 (7 mg, 0.042 mmol) in argon-degassed 2-propanol (2 mL) is added aqueous Sodium carbonate (2 M; 0.5 mL, 1.0 mmol), dicyclohexyl-(2',4',6'-triisopropyl-biphenyl-2-yl)phosphane (XPhos; 10 mg, 0.021 mmol), and catalyst palladium (II) acetate (5 mg, 0.021 mmol). The resulting mixture is heated to 100° C. for 2 h in a Biotage microwave reactor. The mixture is filtered through a Si-thiol palladium scavenging cartridge, which is rinsed with 2 mL EtOAc. The combined filtrates are concentrated, and the crude product is purified by reverse phase HPLC (10-100% MeCN/water with 0.1% ammonium bicarbonate) to yield title compound 256. MS (ES+): m/z 518.9 [M+H]$^+$.

Method 29:
Synthesis of Example 117

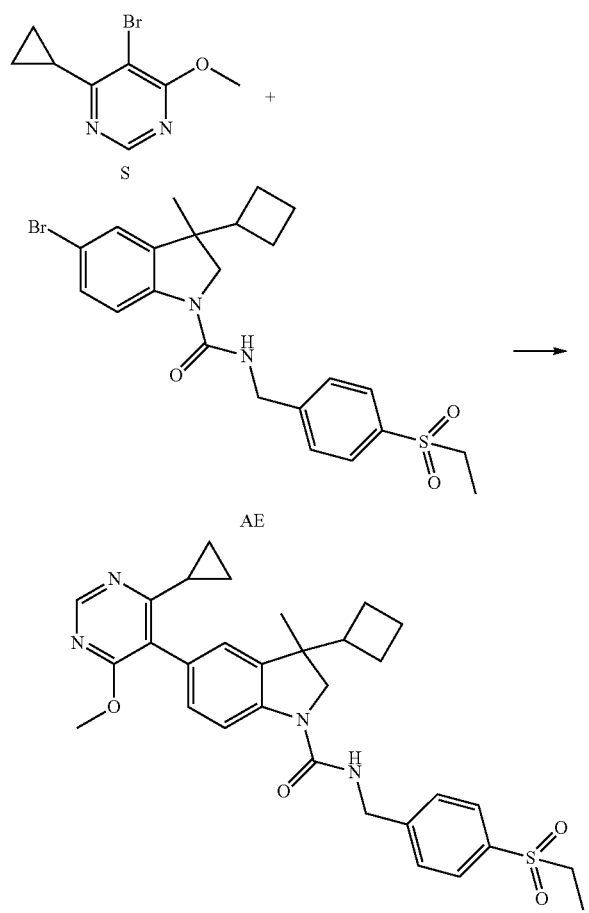

To a solution of intermediate S (78.0 mg, 0.34 mmol) and potassium acetate (100.3 mg, 1.02 mmol) in DME/water/ toluene/EtOH (2 mL; 10:1:6:3 ratio) is added [1,1'-Bis (diphenylphosphino)ferrocene]dichloropalladium(II) (complex with dichloromethane; 56.0 mg, 0.068 mmol) and bis(pinacolato)diboron (190.2 mg, 0.75 mmol). The resulting mixture is degassed with argon and then heated to 90° C. for 30 min in a Biotage microwave reactor. Compound AE (167.3 mg, 0.34 mmol) and dichloropalladium 4-ditert-butylphosphanyl-N,N-dimethyl-aniline (20.0 mg, 0.028 mmol) are added, followed by DMF (1 mL) and aqueous sodium carbonate (2 M; 0.3 mL). The mixture is heated to 120° C. for 20 min in the microwave. The mixture is diluted with MeOH and filtered, then concentrated under reduced pressure. The crude product is purified by reverse phase HPLC twice and converted to free base form with PL-HCO$_3$ MP SPE to yield title compound 117. MS (ES+): m/z 561.3 [M+H]$^+$.

The following compounds were prepared in a similar manner:

Example 118, 120, 125-127

Biological Activity

The compounds of the present invention have activity as modulators of RORγt (retinoid-related orphan receptor γt).

RGA Assay

A nuclear receptor transactivation assay was performed to quantitate the ability of test compounds to inhibit RORγt transactivation of a luciferase reporter. A similar assay is described in: Khan et al., Bioorganic & Medicinal Chemistry Letters 23 (2013), 532-536. The system uses transiently transfected HEK 293 cells cotransfected with two plasmids (pGL4.3, luc2P/GAL4UAS/Hygro, and pBIND, Gal4DBD hRORC LBD1-3). The positive control is co-transiently transfected with both plasmids, and the negative control contains the pGL4.3 promoter sequence. Assays were assembled in 384 well plates where transiently transfected cells and test compound at varying concentrations were incubated for 20-24 hours. The next day, assays plates are taken out and equilibrated at RT for 20-30 minutes. Bright-Glo™ Luciferase Assay System is used to detect Luciferase production. After addition of Bright GLO detection reagent, the plates were incubated at RT for 20 minutes. The plates were read on an Envision plate reader to measure luminescence signal. The RLU signal is converted to POC relative to control and blank wells.

Cell Seeding Media:
RPMI 1640-Invitrogen #11875135), 2.5% FBS-Invitrogen #26140, 1× Penicillin-Streptomycin-Gibco #15140

Compound Dilution Buffer:
1×HBSS-Invitrogen #14025126

Assay Plates: Greiner #781080-020
Bright Glo Luciferase Assay System: Promega #E2620
Thaw lysis buffer provided in kit, add 100 mL lysis buffer to substrate powder.

The below table presents the results obtained when the compounds of the present invention were tested in the above assay, demonstrating their activity as modulators of RORγt:

TABLE II

Table of Biological Activity in RGA Assay

| Example | RGA IC50 (nM) |
| --- | --- |
| 1 | 840 |
| 2 | 920 |

TABLE II-continued

Table of Biological Activity in RGA Assay

| Example | RGA IC50 (nM) |
|---|---|
| 3 | 1000 |
| 4 | 1500 |
| 5 | 1600 |
| 6 | 310 |
| 7 | 340 |
| 8 | 420 |
| 9 | 610 |
| 10 | 640 |
| 11 | 690 |
| 12 | 780 |
| 13 | 840 |
| 14 | 870 |
| 15 | 940 |
| 16 | 960 |
| 17 | 1000 |
| 18 | 1000 |
| 19 | 1100 |
| 20 | 1100 |
| 21 | 1100 |
| 22 | 1200 |
| 23 | 1200 |
| 24 | 1300 |
| 25 | 1300 |
| 26 | 1400 |
| 27 | 1700 |
| 28 | 1200 |
| 29 | 720 |
| 30 | 740 |
| 31 | 740 |
| 32 | 750 |
| 33 | 750 |
| 34 | 790 |
| 35 | 890 |
| 36 | 890 |
| 37 | 920 |
| 38 | 970 |
| 39 | 1000 |
| 40 | 1100 |
| 41 | 1100 |
| 42 | 1100 |
| 43 | 1100 |
| 44 | 1100 |
| 45 | 1200 |
| 46 | 1300 |
| 47 | 1500 |
| 48 | 1600 |
| 49 | 1900 |
| 50 | 1900 |
| 51 | 2000 |
| 52 | 1100 |
| 53 | 1200 |
| 54 | 1300 |
| 55 | 1500 |
| 56 | 400 |
| 57 | 780 |
| 58 | 880 |
| 59 | 1500 |
| 60 | 250 |
| 61 | 730 |
| 62 | 970 |
| 63 | 1400 |
| 64 | 470 |
| 65 | 1500 |
| 66 | 410 |
| 67 | 410 |
| 68 | 1900 |
| 69 | 1100 |
| 70 | 1300 |
| 71 | 740 |
| 72 | 1200 |
| 73 | 460 |
| 74 | 2000 |
| 75 | 140 |
| 76 | 610 |
| 77 | 760 |
| 78 | 790 |
| 79 | 940 |
| 80 | 970 |
| 81 | 980 |
| 82 | 1100 |
| 83 | 370 |
| 84 | 540 |
| 85 | 1300 |
| 86 | 1000 |
| 87 | 680 |
| 88 | 910 |
| 89 | 990 |
| 90 | 580 |
| 91 | 870 |
| 92 | 1100 |
| 93 | 1200 |
| 94 | 2000 |
| 95 | 340 |
| 96 | 450 |
| 97 | 770 |
| 98 | 1200 |
| 99 | 2000 |
| 100 | 1200 |
| 101 | 1100 |
| 102 | 180 |
| 103 | 1800 |
| 104 | 350 |
| 105 | 430 |
| 106 | 650 |
| 107 | 1500 |
| 108 | 1600 |
| 109 | 1700 |
| 110 | 600 |
| 111 | 1700 |
| 112 | 520 |
| 113 | 530 |
| 114 | 500 |
| 115 | 560 |
| 116 | 1000 |
| 117 | 480 |
| 118 | 470 |
| 119 | 320 |
| 120 | 280 |
| 121 | 600 |
| 122 | 1100 |
| 123 | 600 |
| 124 | 1400 |
| 125 | 1100 |
| 126 | 400 |
| 127 | 500 |
| 128 | 210 |
| 129 | 370 |
| 130 | 310 |

Methods of Therapeutic Use

On the basis of their biological properties the compounds of formula (I) according to the invention, or their tautomers, racemates, enantiomers, diastereomers, mixtures thereof and the salts of all the above-mentioned forms are suitable for treating autoimmune and allergic disorders in that they exhibit good modulatory effect upon RORC.

The present invention is therefore directed to compounds of general formula (I), and the pharmaceutically acceptable salts thereof, and all tautomers, racemates, enantiomers, diastereomers, mixtures thereof, which are useful in the treatment of a disease and/or condition wherein the activity of ROR modulators is of therapeutic benefit, including but not limited to the treatment of autoimmune or allergic disorders.

Such disorders that may be treated by the compounds of the invention include for example: psoriasis, rheumatoid arthritis, systemic lupus erythromatosis, scleroderma, Type II diabetes, asthma, allergic rhinitis, allergic eczema, multiple sclerosis, juvenile rheumatoid arthritis, juvenile idiopathic arthritis, inflammatory bowel diseases (including, e.g., Crohn's disease and ulcerative colitis), graft versus host disease, spondyloarthropathies (including, e.g., psoriatic arthritis and ankylosing spondylitis), and uveitis.

For treatment of the above-described diseases and conditions, a therapeutically effective dose will generally be in the range of approximately 0.01 mg to about 10 mg/kg of body weight per dosage of a compound of the invention; preferably, from about 0.1 mg to about 5 mg/kg of body weight per dosage. For example, for administration to a 70 kg person, the dosage range would be approximately 0.7 mg to about 750 mg per dosage of a compound of the invention, preferably from about 7.0 mg to about 350 mg per dosage. Some degree of routine dose optimization may be required to determine an optimal dosing level and pattern. The active ingredient may be administered from 1 to 6 times a day.

General Administration and Pharmaceutical Compositions

When used as pharmaceuticals, the compounds of the invention are typically administered in the form of a pharmaceutical composition. Such compositions can be prepared using procedures well known in the pharmaceutical art and comprise at least one compound of the invention. The compounds of the invention may also be administered alone or in combination with adjuvants that enhance stability of the compounds of the invention, facilitate administration of pharmaceutical compositions containing them in certain embodiments, provide increased dissolution or dispersion, increased antagonist activity, provide adjunct therapy, and the like. The compounds according to the invention may be used on their own or in conjunction with other active substances according to the invention, optionally also in conjunction with other pharmacologically active substances. In general, the compounds of this invention are administered in a therapeutically or pharmaceutically effective amount, but may be administered in lower amounts for diagnostic or other purposes.

Administration of the compounds of the invention, in pure form or in an appropriate pharmaceutical composition, can be carried out using any of the accepted modes of administration of pharmaceutical compositions. Thus, administration can be, for example, orally, buccally (e.g., sublingually), nasally, parenterally, topically, transdermally, vaginally, or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, preferably in unit dosage forms suitable for simple administration of precise dosages. The pharmaceutical compositions will generally include a conventional pharmaceutical carrier or excipient and a compound of the invention as the/an active agent, and, in addition, may include other medicinal agents, pharmaceutical agents, carriers, adjuvants, diluents, vehicles, or combinations thereof. Such pharmaceutically acceptable excipients, carriers, or additives as well as methods of making pharmaceutical compositions for various modes or administration are well-known to those of skill in the art. The state of the art is evidenced, e.g., by Remington: The Science and Practice of Pharmacy, 20th Edition, A. Gennaro (ed.), Lippincott Williams & Wilkins, 2000; Handbook of Pharmaceutical Additives, Michael & Irene Ash (eds.), Gower, 1995; Handbook of Pharmaceutical Excipients, A. H. Kibbe (ed.), American Pharmaceutical Ass'n, 2000; H. C. Ansel and N. G. Popovish, Pharmaceutical Dosage Forms and Drug Delivery Systems, 5th ed., Lea and Febiger, 1990; each of which is incorporated herein by reference in their entireties to better describe the state of the art. As one of skill in the art would expect, the forms of the compounds of the invention utilized in a particular pharmaceutical formulation will be selected (e.g., salts) that possess suitable physical characteristics (e.g., water solubility) that are required for the formulation to be efficacious.

All patent and non-patent documents or literature cited in this application are herein incorporated by reference in their entirety.

The invention claimed is:
1. A compound of formula (I)

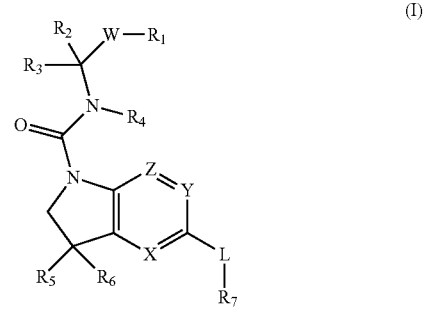

$R_1$ is:
—CN,
—S(O)$_m$C$_{1-6}$alkyl,
—S(O)$_m$C$_{1-6}$cyanoalkyl,
—S(O)$_m$C$_{1-6}$haloalkyl,
—S(O)$_m$C$_{3-6}$cycloalkyl,
—S(O)$_m$C$_{1-6}$ hydroxyalkyl,
—S(O)$_m$C$_{1-6}$alkyloxy,
—SO$_2$NR$_a$R$_b$,
—NR$_a$S(O)$_m$C$_{1-6}$alkyl,
—NR$_a$S(O)$_m$C$_{3-6}$cycloalkyl,
—S(O)(NRc)C$_{1-6}$alkyl,
—S(O)(NRc)C$_{3-6}$cycloalkyl or
—S(O)(NRc)NR$_a$R$_b$
wherein R$_a$ and R$_b$ are each independently H, C$_{1-6}$alkyl, C$_{3-6}$cycloalkyl, C$_{1-6}$haloalkyl, C$_{1-6}$cyanoalkyl, or C$_{1-6}$alkyloxy or;
R$_a$ and R$_b$ taken together with the nitrogen to which they are attached form a C$_{2-6}$ heterocyclic ring optionally containing 1-4 additional groups selected from NH, O and S;
and m is 0, 1 or 2; and
R$_c$ is each independently H, C$_{1-6}$alkyl, C$_{3-6}$cycloalkyl, or C$_{1-6}$alkyloxy;
W is:
C$_{6-14}$ aryl,
a C$_{2-10}$ heteroaryl containing 1-4 groups selected from N, NH, O and S,
saturated and partially saturated C$_{2-10}$ heterocyclyl containing 1-4 groups selected from N, NH, O and S, or
saturated and partially saturated C$_{3-12}$ cycloalkyl ring,
wherein each W is optionally substituted with 0-4 substituents selected from the group consisting of cyano, halo, hydroxy, C$_{1-6}$alkyl, C$_{1-6}$ haloalkyl, C$_{1-6}$ hydroxyalkyl, C$_{1-6}$ alkenyl, C$_{1-6}$ haloalkenyl, C$_{1-6}$ alkynyl, C$_{1-6}$ haloalkynyl, C$_{3-6}$ cycloalkyl, C$_{3-6}$ heterocycle containing 1-4 groups selected from NH, O and S, C$_{1-6}$ alkoxy, C$_{3-6}$ cycloalkyl-oxy, —S(O)$_m$C$_{1-6}$ alkyl, —S(O)$_m$C$_{3-6}$ cycloalkyl, CN, —C(O)—NR$_c$R$_d$—C(O)—OR$_e$, —NR$_c$R$_d$, NR$_c$R$_d$—C$_{1-6}$alkyl-, and R$_c$O—C$_{1-6}$alkoxy NR$_c$R$_d$—C$_{1-6}$alkoxy-, wherein R$_c$ and R$_d$ is each independently H, C$_{1-6}$ alkyl, C$_{1-6}$ alkenyl, C$_{1-6}$ alkynyl, C$_{3-12}$ cycloalkyl, C$_{6-14}$ aryl, C$_{2-6}$ heterocycle containing 1-4 groups selected from NH, O and S, or a C$_{2-10}$heteroaryl containing 1-4 groups selected from N, NH, O and S, or Rc and R$_d$ taken together with the nitrogen to which they are attached form a C$_{2-6}$ heterocyclic ring optionally containing 1-4 additional groups selected from NH, O and S;

R$_2$ is:
—C$_{1-6}$alkyl,
—C$_{3-6}$cycloalkyl,
—C$_{1-6}$alkyloxy,
—C$_{1-6}$ hydroxyalkyl,
—C$_{1-6}$haloalkyl,
—H,
—C(O)OR$_e$, or —C(O)NR$_e$R$_f$, wherein R$_e$ and R$_f$ is each independently H or C$_{1-6}$ alkyl;

R$_3$ is:
—C$_{1-6}$alkyl,
—C$_{3-6}$cycloalkyl,
—C$_{1-6}$alkyloxy;
—H,
—C(O)OR$_e$, or C(O)NR$_e$R$_f$, wherein R$_e$ and R$_f$ is each independently H or C$_{1-6}$ alkyl;

or R$_2$ and R$_3$ taken together with the carbon to which they are attached form a C$_{3-12}$ carbocyclic ring or a C$_{2-10}$ heterocyclic containing 1-4 groups selected from NH, O and S;

R$_4$ is:
—H,
—C$_{1-6}$alkyl,
—C$_{1-6}$alkyloxy, or
—C$_{3-6}$cycloalkyl;

X, Y and Z are chosen independently from CR$_e$ wherein R$_e$ is:
—H,
-halo,
—C$_{1-6}$alkyl,
—C$_{1-6}$ haloalkyl,
—C$_{1-6}$ haloalkenyl,
—C$_{1-6}$ haloalkynyl,
—C$_{3-6}$ cycloalkyl,
—C$_{1-6}$ alkoxy,
—C$_{3-6}$ cycloalkyloxy,
—OC$_{1-6}$alkyl,
—OC$_{3-6}$ cycloalkyl,
—S(O)$_m$C$_{1-6}$ alkyl,
—S(O)$_m$C$_{3-6}$ cycloalkyl,
CN,
—C(O)—NR$_f$R$_g$, —C(O)—OR$_f$, or —NR$_f$R$_g$, wherein R$_f$ and R$_g$ is each independently H or —C$_{1-6}$ alkyl;
C$_{1-6}$ alkenyl,
C$_{1-6}$ alkynyl,
C$_{3-12}$ cycloalkyl, C$_{6-14}$ aryl, C$_{3-6}$ heterocycle containing 1-4 groups selected from N, NH, O and S, or a C$_{2-10}$ heteroaryl containing 1-4 groups selected from N, NH, O and S;

R$_5$ is:
—H
-halo,
—C$_{1-6}$ alkyl, C$_{1-6}$ alkenyl,
—C$_{1-6}$ alkoxy,
—S(O)$_m$C$_{1-6}$alkyl,
—C$_{6-14}$ aryl,
—C$_{2-10}$ heterocyclyl containing 1-4 groups selected from N, NH, O and S,
—C$_{2-10}$ heteroaryl containing 1-4 groups selected from N, NH, O and S,
—CN,
—C$_3$-C$_6$cycloalkyl, or-
—C$_{1-6}$haloalkyl,
wherein R$_5$ may be optionally substituted with 0-5 halo, C$_{1-6}$ alkyl, C$_{1-6}$ alkoxy, —S(O)$_m$C$_{1-6}$alkyl, C$_{6-14}$ aryl, C$_{2-10}$ heterocyclyl containing 1-4 groups selected from N, NH, O and S, or a C$_{2-10}$ heteroaryl containing 1-4 groups selected from N, NH, O and S, CN, C$_3$-C$_6$cycloalkyl, OH or —C(O)—NR$_a$R$_b$, R$_6$ is:
-halo,
—C$_{1-6}$ alkyl
—C$_{1-6}$ alkenyl,
—C$_{1-6}$ alkoxy,
—S(O)$_m$C$_{1-6}$alkyl,
—C$_{6-14}$ aryl,
—C$_{2-10}$ heterocyclyl containing 1-4 groups selected from N, NH, O and S,
—C$_{2-10}$ heteroaryl containing 1-4 groups selected from N, NH, O and S,
—H,
—CN,
—C$_3$-C$_6$cycloalkyl, or-
—C$_{1-6}$haloalkyl,
wherein R$_6$ may be optionally substituted with 0-5 halo, C$_{1-6}$ alkyl, C$_{1-6}$ alkoxy, —S(O)$_m$C$_{1-6}$alkyl, C$_{6-14}$ aryl, C$_{2-10}$ heterocyclyl containing 1-4 groups selected from N, NH, O and S, or a C$_{2-10}$ heteroaryl containing 1-4 groups selected from N, NH, O and S, CN, C$_3$-C$_6$cycloalkyl, OH or —C(O)—NR$_a$R$_b$, or R$_5$ and R$_6$ taken together with the carbon to which they attached form a C$_{3-12}$ carbocyclic ring or a C$_{2-10}$ heterocyclic containing 1-4 groups selected from N, NH, O and S;

L is:
a direct bond,
—C=C—

—C≡C—,

—S(O)$_m$—,
—NR$_a$S(O)$_m$,
—S(O)$_m$NR$_a$—
—O—,
—C(O)—,
—(CH$_2$)$_n$—,
—O—(CH$_2$)$_n$—,
—N(R$_a$)—,
—N(R$_a$)—(CH$_2$)$_n$—,
—(CH$_2$)$_n$—N(R$_a$)—,
—C(O)—N(Ra)—,
—C(O)—N(R$_a$)—(CH$_2$)$_n$— or
—N(R$_a$)—C(O)—N(R$_b$)—;
wherein R$_a$ and R$_b$ is each independently H or C$_{1-3}$ alkyl;

R$_7$ is:
halo,
cycloalkyl, cycloalkenyl,

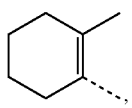

—C$_{6-14}$ aryl,
—C$_{2-10}$ heterocyclyl containing 1-4 groups selected from N, NH, O and S,
C$_{2-10}$ heteroaryl containing 1-4 groups selected from N, NH, O and S,
wherein R$_7$ may be optionally substituted with 0-5 substituents selected from the group consisting of halogen, hydroxy, C$_{1-6}$alkyl, C$_{1-6}$ haloalkyl, C$_{1-6}$ hydroxyalkyl, C$_{1-6}$ haloalkenyl, C$_{1-6}$ haloalkynyl, C$_{3-6}$ cycloalkyl, C$_{3-7}$ heterocycle containing 1-4 groups selected from N, NH, O and S, C$_{6-14}$ aryl, C$_{2-10}$ heteroaryl containing 1-4 groups selected from N, NH, O and S, C$_{1-6}$ alkoxy, C$_{1-6}$ haloalkoxy, C$_{3-6}$ cycloalkyloxy, —S(O)$_m$C$_{1-6}$ alkyl, —S(O)$_m$C$_{3-6}$ cycloalkyl, CN, —C(O)—NR$_c$R$_d$, —C(O)—OR$_c$, NR$_c$R$_d$ and NR$_c$R$_d$C$_{1-6}$alkyl-, wherein R$_c$ and R$_d$ is each independently H, C$_{1-6}$ alkyl, C$_{1-6}$ alkenyl, C$_{1-6}$ alkynyl, cycloalkyl, —C$_{6-14}$ aryl, C$_{2-10}$ heterocyclyl containing 1-4 groups selected from N, NH, O and S, or a C$_{2-10}$ heteroaryl containing 1-4 groups selected from N, NH, O and S, wherein each heterocyclyl, aryl or heteroaryl is optionally substituted by C$_{1-6}$ alkyl, C$_{1-6}$ alkoxy; or Rc and Rd—together with the nitrogen to which they are attached form a C$_{2-6}$ heterocyclic ring optionally containing 1-4 additional groups selected from N, NH, O and S;
each n is independently 1-4; each m is independently 0-2;
or a pharmaceutically acceptable salt thereof.

2. A compound of formula (I) according to claim 1, wherein:
R$_1$ is:
—S(O)$_m$C$_{1-6}$alkyl,
—S(O)$_m$C$_{1-6}$haloalkyl,
—S(O)—C$_{3-6}$cycloalkyl,
—SO$_2$NR$_a$R$_b$,
wherein R$_a$ and R$_b$ are each independently H, C$_{1-6}$alkyl, C$_{3-6}$cycloalkyl, or C$_{1-6}$alkyloxy, or
R$_a$ and R$_b$ taken together with the nitrogen to which they are attached form a C$_{2-6}$ heterocyclic ring optionally containing 1-4 additional groups selected from NH, O and S; —S(O)(NRc)C$_{1-6}$alkyl,
—S(O)(NRc)C$_{3-6}$cycloalkyl,
wherein R$_c$ is each independently H, C$_{1-6}$alkyl, C$_{3-6}$cycloalkyl, or C$_{1-6}$alkyloxy,
or
—CN;
and each m is independently 0-2;
or a pharmaceutically acceptable salt thereof.

3. A compound of formula (I) according to claim 1, wherein:
W is:
C$_{6-14}$ aryl, C$_{2-10}$ heteroaryl containing 1-4 groups selected from N, NH, O and S, or bicyclo [1.1.1] pentane,
wherein each W is optionally substituted with 0-4 substituents selected from the group consisting of halo, hydroxy, C$_{1-6}$alkyl, C$_{1-6}$ haloalkyl, C$_{1-6}$ haloalkenyl, C$_{1-6}$ haloalkynyl, C$_{3-6}$ cycloalkyl, C$_{1-6}$ alkoxy, C$_{3-6}$ cycloalkyloxy, —S(O)$_m$C$_{1-6}$ alkyl, —S(O)$_m$C$_{3-6}$ cycloalkyl, CN, —C(O)—NR$_c$R$_d$, —C(O)—OR$_c$, and NR$_c$R$_d$ wherein R$_c$ and R$_d$ is each independently H, C$_{1-6}$ alkyl, C$_{1-6}$ alkenyl, C$_{1-6}$ alkynyl, cycloalkyl, —C$_{6-14}$ aryl, C$_{2-10}$ heterocyclyl containing 1-4 groups selected from NH, O and S, or a C$_{2-10}$ heteroaryl containing 1-4 groups selected from N, NH, O and S;
or a pharmaceutically acceptable salt thereof.

4. A compound of formula (I) according to claim 1, wherein:
R$_2$ is:
H, or
C$_{1-6}$alkyl; and
R$_3$ is:
H, or
C$_{1-6}$alkyl;
or R$_2$ and R$_3$ taken together form a cyclopropane ring
or a pharmaceutically acceptable salt thereof.

5. A compound of formula (I) according to claim 1, wherein:
R$_4$ is:
H, or
C$_{1-6}$alkyl;
or a pharmaceutically acceptable salt thereof.

6. A compound of formula (I) according to claim 1, wherein:
X, Y and Z are chosen independently from CR$_e$;
and R$_e$ is:
H,
halo,
C$_{1-6}$alkyl,
OC$_{1-6}$alkyl,
or
cycloalkyl;
or a pharmaceutically acceptable salt thereof.

7. A compound of formula (I) according to claim 1, wherein:
R$_5$ is:
H;
C$_{1-6}$ alkyl, or
C$_3$-C$_6$cycloalkyl;
wherein R$_5$ may be optionally substituted with 0-5 halo, C$_{1-6}$ alkyl, C$_{1-6}$ alkoxy, —S(O)$_m$C$_{1-6}$alkyl, —S(O)$_m$C$_{1-6}$alkyl, C$_{6-14}$ aryl, C$_{2-10}$ heterocyclyl containing 1-4 groups selected from NH, O and S, C$_{2-10}$ heteroaryl containing 1-4 groups selected from N, NH, O and S, CN, or C$_3$-C$_6$cycloalkyl;
R$_6$ is:
H;
C$_{1-6}$ alkyl, or
C$_3$-C$_6$cycloalkyl;
wherein R$_6$ may be optionally substituted optionally substituted with 0-5 substituents selected from the group consisting of halogen, C$_{1-6}$ haloalkyl, C$_{1-6}$ haloalkenyl, C$_{1-6}$ haloalkynyl, C$_{3-6}$ cycloalkyl, C$_{1-6}$ alkoxy, C$_{3-6}$ cycloalkyloxy, —S(O)$_m$C$_{1-6}$ alkyl, —S(O)$_m$C$_{3-6}$ cycloalkyl, —CN, —C(O)—NR$_c$R$_d$, —C(O)—OR$_c$, and NR$_c$R$_d$ wherein R$_c$ and R$_d$ is H, C$_{1-6}$ alkyl, C$_{1-6}$ alkenyl, C$_{1-6}$ alkynyl, cycloalkyl, —C$_{6-14}$ aryl, C$_{2-10}$ heterocyclyl containing 1-4 groups selected from NH, O and S, C$_{2-10}$ heteroaryl containing 1-4 groups selected from N, NH, O and S;
or R$_5$ and R$_6$ taken together with the carbon to which they attached form a C$_{3-12}$ carbocyclic ring or a C$_{2-10}$ heterocyclic ring containing 1-4 groups selected from NH, O and S;
or a pharmaceutically acceptable salt thereof.

8. A compound of formula (I) according to claim 1, wherein:

L is:
a bond,
—O— or
—O—CH$_2$—;
or a pharmaceutically acceptable salt thereof.

9. A compound of formula (I) according to claim 1, wherein:

R$_7$ is:
halo, or
C$_{6-14}$ aryl or C$_{2-10}$ heteroaryl containing 1-4 groups selected from N, NH, O and S;
wherein R$_7$ may be optionally substituted with 0-5 substituents selected from the group consisting of halogen, hydroxy, C$_{1-6}$ alkyl, C$_{1-6}$ haloalkyl, C$_{1-6}$ hydroxyalkyl, C$_{1-6}$ haloalkenyl, C$_{1-6}$ haloalkynyl, C$_{3-6}$ cycloalkyl, C$_{1-6}$ alkoxy, C$_{1-6}$ haloalkoxy, C$_{3-6}$ cycloalkyloxy, —S(O)$_m$C$_{1-6}$ alkyl, —S(O)$_m$C$_{3-6}$ cycloalkyl, —CN, —C(O)—NR$_c$R$_d$, —C(O)—OR$_c$, NR$_c$R$_d$C$_{1-6}$alkyl- and NR$_c$R$_d$, wherein R$_c$ and R$_d$ is H, C$_{1-6}$ alkyl, C$_{1-6}$ alkenyl, C$_{1-6}$ alkynyl, C$_{3-12}$ cycloalkyl, C$_{6-14}$ aryl, C$_{2-6}$ heterocycle containing 1-4 groups selected from NH, O and S, or a C$_{2-10}$ heteroaryl containing 1-4 groups selected from N, NH, O and S;
each m is independently 0-2;
or a pharmaceutically acceptable salt thereof.

10. A compound of formula (I) according to claim 1, wherein:

R$_1$ is:
—S(O)$_m$C$_{1-6}$alkyl,
—S(O)$_m$C$_{3-6}$cycloalkyl, or
—SO$_2$NR$_a$R$_b$
wherein R$_a$ and R$_b$ are each independently H, C$_{1-6}$alkyl, C$_{3-6}$cycloalkyl, or C$_{1-6}$alkyloxy, or
R$_a$ and R$_b$ taken together with the nitrogen to which they are attached form a C$_{2-6}$ heterocyclic ring optionally containing 1-4 additional groups selected from NH, O and S;
or
—CN;

W is:
C$_{6-14}$ aryl or a C$_{2-10}$ heteroaryl containing 1-4 groups selected from N, NH, O and S,
wherein each W is optionally substituted with 0-4 substituents selected from the group consisting of halo, hydroxy, C$_{1-6}$alkyl, C$_{1-6}$ haloalkyl, C$_{1-6}$ haloalkenyl, C$_{1-6}$ haloalkynyl, C$_{3-6}$ cycloalkyl, C$_{1-6}$ alkoxy, C$_{3-6}$ cycloalkyloxy, —S(O)$_m$C$_{1-6}$ alkyl, —S(O)$_m$C$_{3-6}$ cycloalkyl, CN, —C(O)—NR$_c$R$_d$, —C(O)—OR$_c$, and NR$_c$R$_d$ wherein R$_c$ and R$_d$ is each independently H, C$_{1-6}$ alkyl, C$_{1-6}$ alkenyl, C$_{1-6}$ alkynyl, C$_{3-12}$ cycloalkyl, C$_{6-14}$ aryl, C$_{2-6}$ heterocycle containing 1-4 groups selected from NH, O and S, or a C$_{2-10}$ heteroaryl containing 1-4 groups selected from N, NH, O and S;

R$_2$ is:
H, or
C$_{1-6}$alkyl;
R$_3$ is:
H, or
C$_{1-6}$alkyl;
R$_4$ is:
H, or
C$_{1-6}$alkyl;
X, Y and Z are chosen independently from CR$_e$;
and R$_e$ is:
H,
halo,
C$_{1-6}$alkyl,
C$_{1-6}$ haloalkyl,
C$_{1-6}$ haloalkenyl,
C$_{1-6}$ haloalkynyl,
C$_{3-6}$ cycloalkyl,
C$_{1-6}$ alkoxy,
C$_{3-6}$ cycloalkyloxy,
—S(O)$_m$C$_{1-6}$ alkyl,
—S(O)—C$_{3-6}$ cycloalkyl,
—CN,
—C(O)—NR$_f$R$_g$, —C(O)—OR$_f$, or —NR$_f$R$_g$, wherein R$_f$ and R$_g$ is H or C$_{1-6}$ alkyl,
—C$_{1-6}$ alkenyl,
—C$_{1-6}$ alkynyl, or
—C$_{3-12}$ cycloalkyl;

R$_5$ is:
H;
C$_{1-6}$ alkyl, or
C$_3$-C$_6$cycloalkyl;
wherein R$_5$ may be optionally substituted with 0-5 halo, C$_{1-6}$ alkyl, C$_{1-6}$ alkoxy, —S(O)$_m$C$_{1-6}$alkyl, —S(O)$_m$C$_{1-6}$alkyl, —C$_{6-14}$ aryl,
C$_{2-10}$ heterocyclyl containing 1-4 groups selected from NH, O and S, C$_{2-10}$ heteroaryl containing 1-4 groups selected from N, NH, O and S, CN, or C$_3$-C$_6$cycloalkyl;

R$_6$ is:
H;
C$_{1-6}$ alkyl, or
C$_3$-C$_6$cycloalkyl;
wherein R$_6$ may be optionally substituted optionally substituted with 0-5 substituents selected from the group consisting of halogen, C$_{1-6}$ haloalkyl, C$_{1-6}$ haloalkenyl, C$_{1-6}$ haloalkynyl, C$_{3-6}$ cycloalkyl, C$_{1-6}$ alkoxy, C$_{3-6}$ cycloalkyloxy, —S(O)$_m$C$_{1-6}$ alkyl, —S(O)$_m$C$_{3-6}$ cycloalkyl, —CN, —C(O)—NR$_c$R$_d$, —C(O)—OR$_c$, and NR$_c$R$_d$ wherein R$_c$ and R$_d$ is H, C$_{1-6}$ alkyl, C$_{1-6}$ alkenyl, C$_{1-6}$ alkynyl, C$_{3-12}$ cycloalkyl, C$_{6-14}$ aryl, C$_{2-6}$ heterocycle containing 1-4 groups selected from NH, O and S, or a C$_{2-10}$ heteroaryl containing 1-4 groups selected from N, NH, O and S;

or R$_5$ and R$_6$ taken together with the carbon to which they attached form a C$_{3-12}$ carbocyclic ring;

L is:
a bond,
—O— or
—O—(CH$_2$)$_n$—;
R$_7$ is:
halo, C$_{6-14}$ aryl or C$_{2-10}$ heteroaryl containing 1-4 groups selected from N, NH, O and S;
wherein R$_7$ may be optionally substituted with 0-5 substituents selected from the group consisting of halogen, hydroxy, C$_{1-6}$ alkyl, C$_{1-6}$ haloalkyl, C$_{1-6}$ hydroxyalkyl, C$_{1-6}$ haloalkenyl, C$_{1-6}$ haloalkynyl, C$_{3-6}$ cycloalkyl, C$_{1-6}$ alkoxy, C$_{1-6}$haloalkoxy, C$_{3-6}$ cycloalkyloxy, —S(O)$_m$C$_{1-6}$ alkyl, —S(O)$_m$C$_{3-6}$ cycloalkyl, —CN, —C(O)—NR$_c$R$_d$, —C(O)—OR$_c$, and NR$_c$R$_d$, wherein R$_c$ and R$_d$ is H, C$_{1-6}$ alkyl, C$_{1-6}$ alkenyl, C$_{1-6}$ alkynyl, C$_{3-12}$ cycloalkyl, C$_{6-14}$ aryl, C$_{2-6}$ heterocycle containing 1-4 groups selected from NH, O and S, or a C$_{2-10}$ heteroaryl containing 1-4 groups selected from N, NH, O and S;
each m is independently 0-2;
or a pharmaceutically acceptable salt thereof.

11. A compound selected from the compounds in the following table:

| Example | Structure |
|---|---|
| 1 | 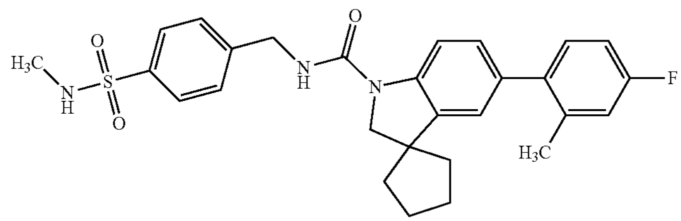 [SMILES: CNS(=O)(=O)c1ccc(CNC(=O)N2CC3(CCCC3)c3cc(-c4ccc(F)cc4C)ccc32)cc1] |
| 2 | 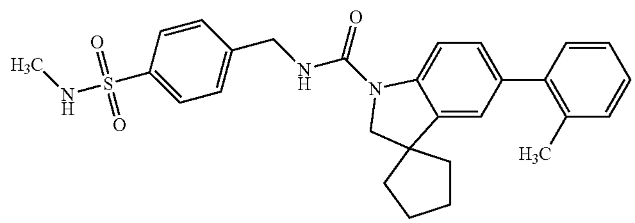 [SMILES: CNS(=O)(=O)c1ccc(CNC(=O)N2CC3(CCCC3)c3cc(-c4ccccc4C)ccc32)cc1] |
| 3 | 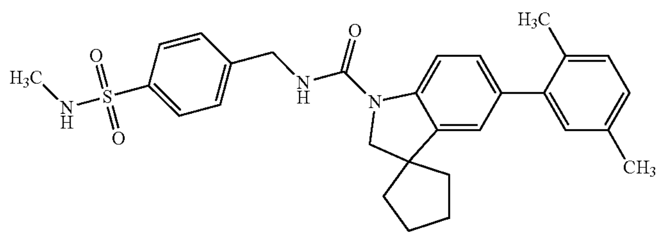 |
| 4 | 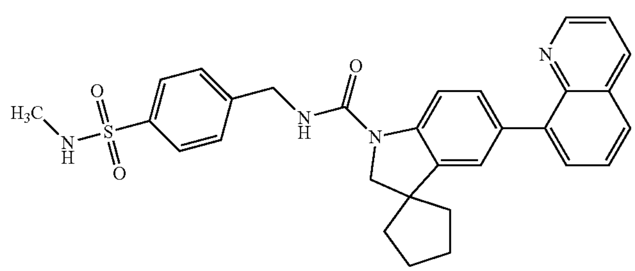 [SMILES: CNS(=O)(=O)c1ccc(CNC(=O)N2CC3(CCCC3)c3cc(-c4cccc5cccnc45)ccc32)cc1] |
| 5 | 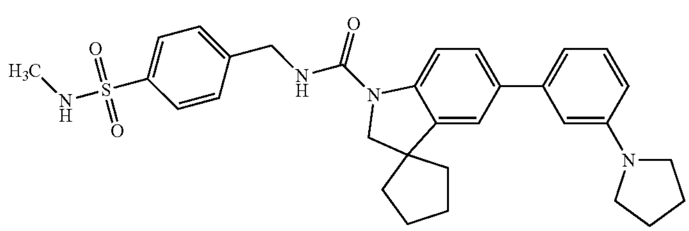 [SMILES: CNS(=O)(=O)c1ccc(CNC(=O)N2CC3(CCCC3)c3cc(-c4cccc(N5CCCC5)c4)ccc32)cc1] |
| 6 | 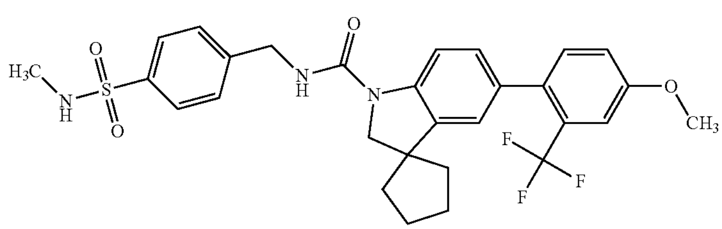 |

-continued

| Example | Structure |
|---|---|
| 7 | 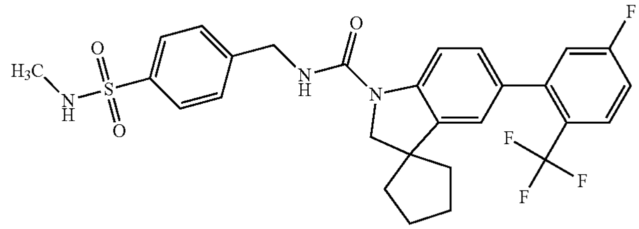 [SMILES: CNS(=O)(=O)c1ccc(CNC(=O)N2CC3(CCCC3)c3cc(-c4cc(F)ccc4C(F)(F)F)ccc32)cc1] |
| 8 | 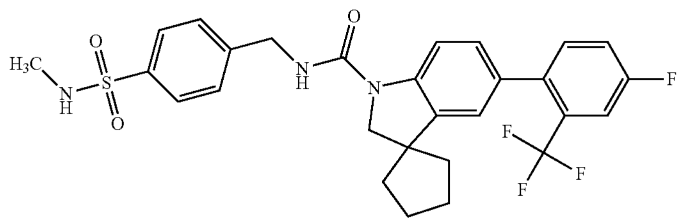 [SMILES: CNS(=O)(=O)c1ccc(CNC(=O)N2CC3(CCCC3)c3cc(-c4ccc(F)cc4C(F)(F)F)ccc32)cc1] |
| 9 | 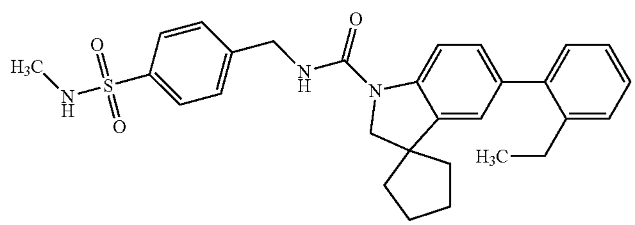 [SMILES: CCc1ccccc1-c1ccc2c(c1)C1(CCCC1)CN2C(=O)NCc1ccc(S(=O)(=O)NC)cc1] |
| 10 | 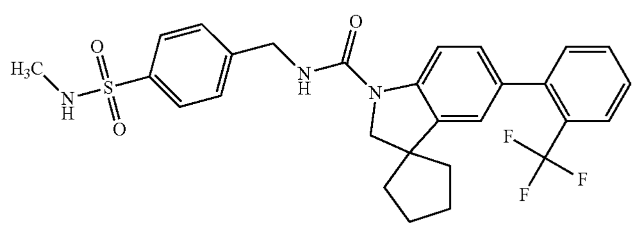 [SMILES: CNS(=O)(=O)c1ccc(CNC(=O)N2CC3(CCCC3)c3cc(-c4ccccc4C(F)(F)F)ccc32)cc1] |
| 11 | 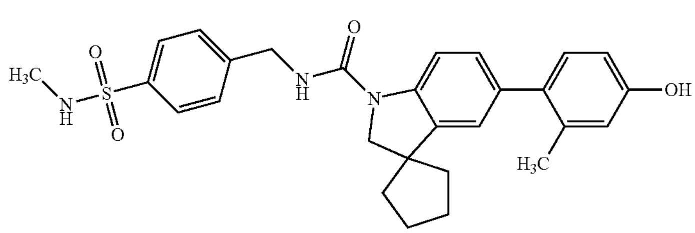 [SMILES: CNS(=O)(=O)c1ccc(CNC(=O)N2CC3(CCCC3)c3cc(-c4ccc(O)cc4C)ccc32)cc1] |
| 12 | 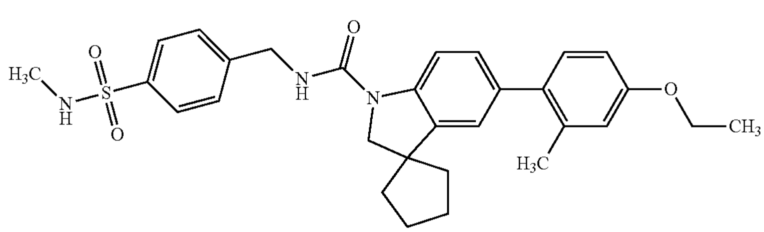 [SMILES: CCOc1ccc(-c2ccc3c(c2)C2(CCCC2)CN3C(=O)NCc2ccc(S(=O)(=O)NC)cc2)c(C)c1] |

-continued
| Example | Structure |
|---|---|
| 13 | 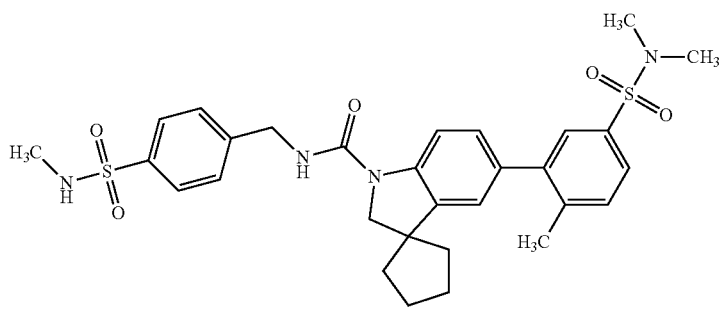 |
| 14 | 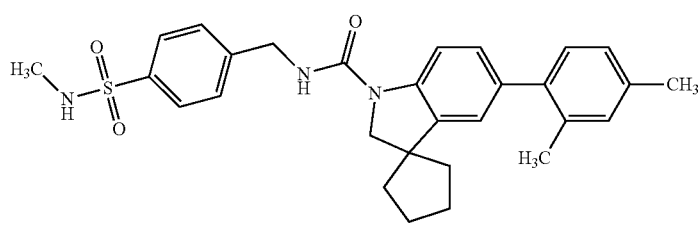 |
| 15 | 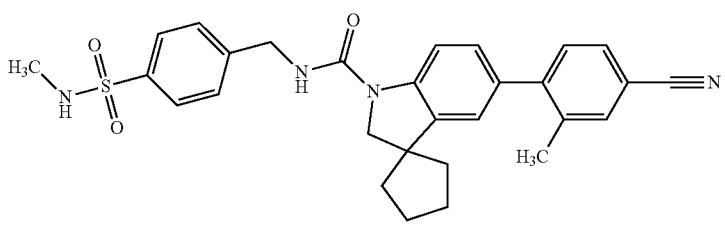 [SMILES: CNS(=O)(=O)c1ccc(CNC(=O)N2CC3(CCCC3)c3cc(-c4ccc(C#N)cc4C)ccc32)cc1] |
| 16 | 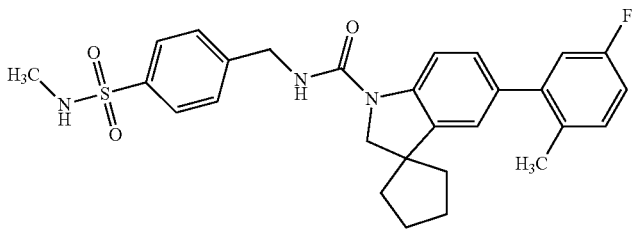 [SMILES: CNS(=O)(=O)c1ccc(CNC(=O)N2CC3(CCCC3)c3cc(-c4cc(F)ccc4C)ccc32)cc1] |
| 17 | 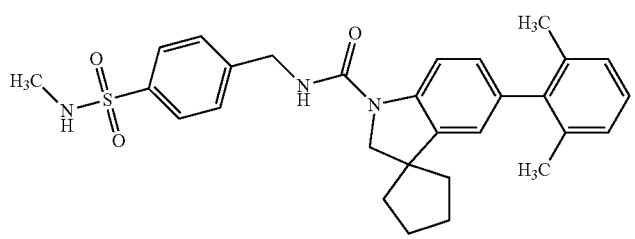 [SMILES: CNS(=O)(=O)c1ccc(CNC(=O)N2CC3(CCCC3)c3cc(-c4c(C)cccc4C)ccc32)cc1] |
| 18 | 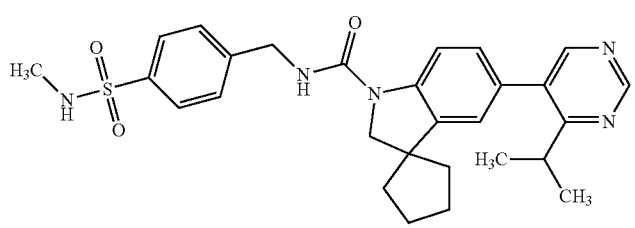 [SMILES: CNS(=O)(=O)c1ccc(CNC(=O)N2CC3(CCCC3)c3cc(-c4cncnc4C(C)C)ccc32)cc1] |

| Example | Structure |
|---|---|
| 19 | 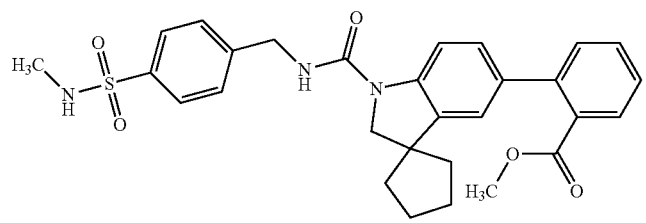 [SMILES: CNS(=O)(=O)c1ccc(CNC(=O)N2CC3(CCCC3)c3cc(-c4ccccc4C(=O)OC)ccc32)cc1] |
| 20 | 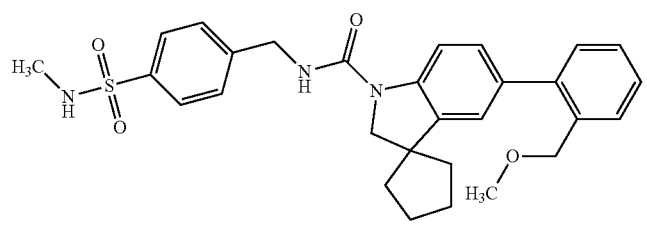 [SMILES: CNS(=O)(=O)c1ccc(CNC(=O)N2CC3(CCCC3)c3cc(-c4ccccc4COC)ccc32)cc1] |
| 21 | 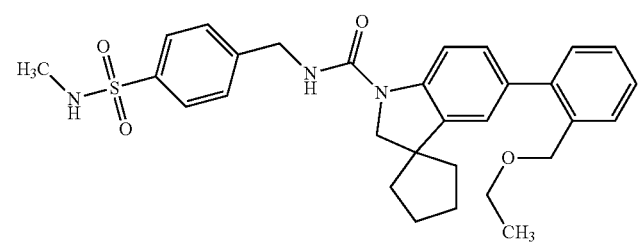 [SMILES: CCOCc1ccccc1-c1ccc2c(c1)C1(CCCC1)CN2C(=O)NCc1ccc(S(=O)(=O)NC)cc1] |
| 22 | 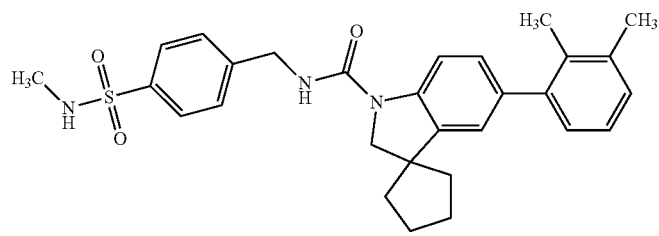 |
| 23 | 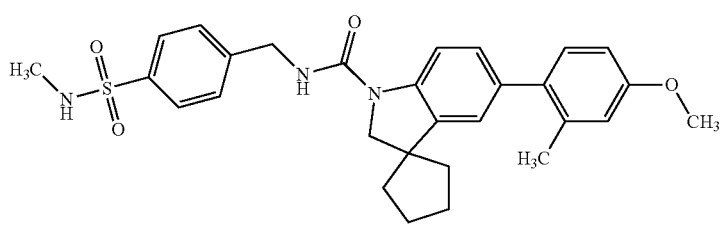 |
| 24 | 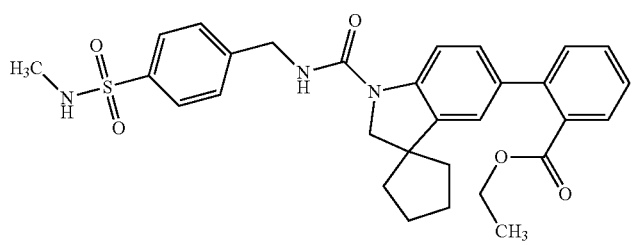 [SMILES: CCOC(=O)c1ccccc1-c1ccc2c(c1)C1(CCCC1)CN2C(=O)NCc1ccc(S(=O)(=O)NC)cc1] |

| Example | Structure |
|---|---|
| 25 | 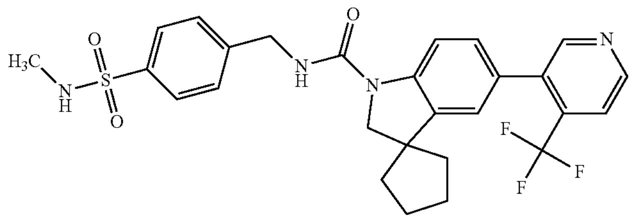 [SMILES: CNS(=O)(=O)c1ccc(CNC(=O)N2CC3(CCCC3)c3cc(-c4cnccc4C(F)(F)F)ccc32)cc1] |
| 26 | 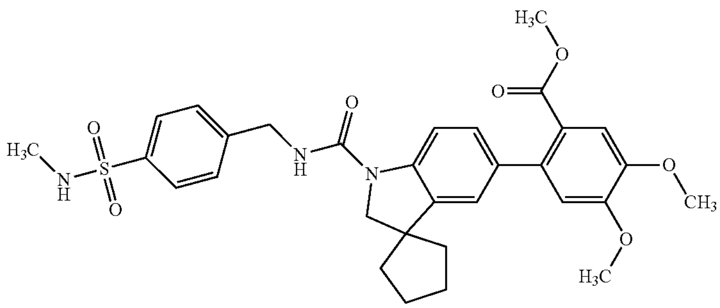 |
| 27 | 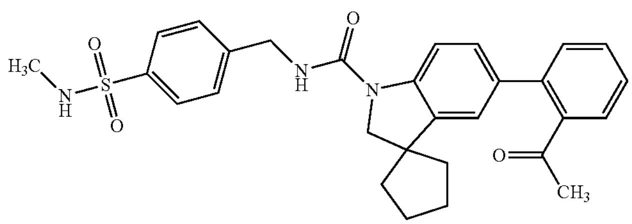 [SMILES: CNS(=O)(=O)c1ccc(CNC(=O)N2CC3(CCCC3)c3cc(-c4ccccc4C(C)=O)ccc32)cc1] |
| 28 | 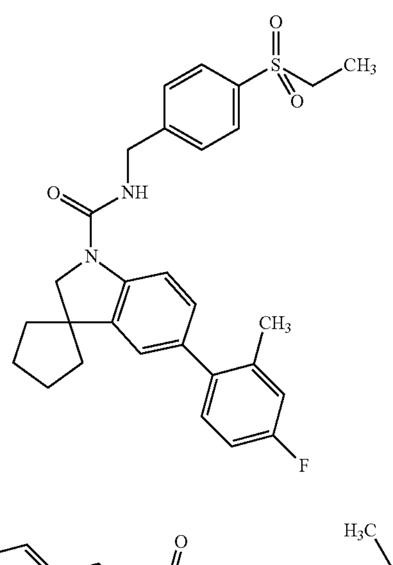 |
| 29 | 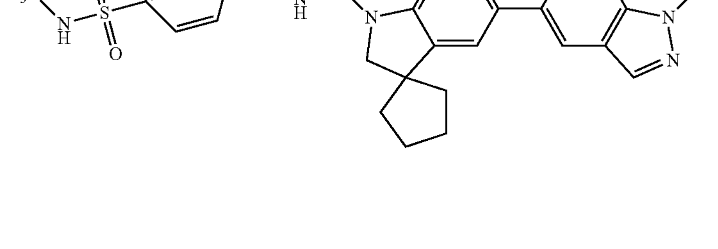 |

| Example | Structure |
|---|---|
| 30 | (chemical structure) |
| 31 | (chemical structure) |
| 32 | (chemical structure) |
| 33 | (chemical structure) |
| 34 | (chemical structure) |
| 35 | (chemical structure) |

-continued
| Example | Structure |
|---|---|
| 36 | 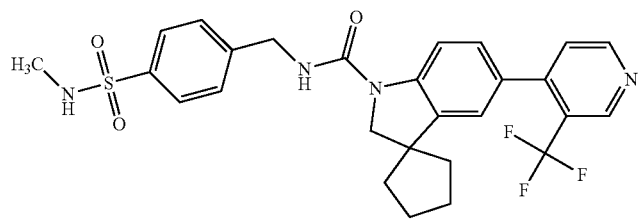 [SMILES: CNS(=O)(=O)c1ccc(CNC(=O)N2CC3(CCCC3)c3cc(-c4ccncc4C(F)(F)F)ccc32)cc1] |
| 37 | 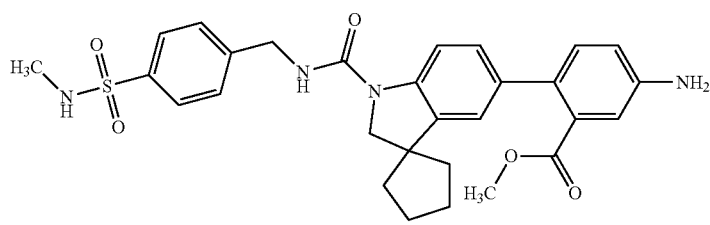 [SMILES: CNS(=O)(=O)c1ccc(CNC(=O)N2CC3(CCCC3)c3cc(-c4ccc(N)cc4C(=O)OC)ccc32)cc1] |
| 38 | 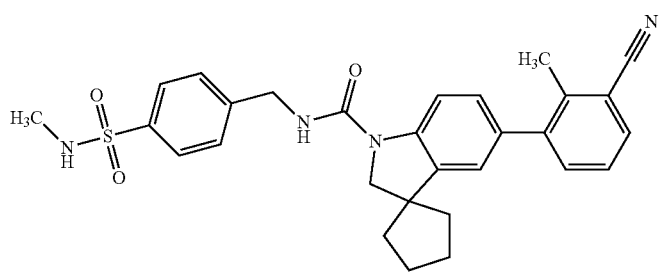 [SMILES: CNS(=O)(=O)c1ccc(CNC(=O)N2CC3(CCCC3)c3cc(-c4cccc(C#N)c4C)ccc32)cc1] |
| 39 | 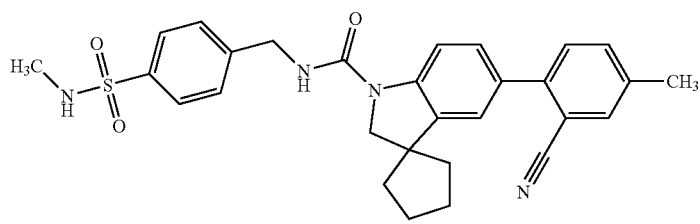 |
| 40 | 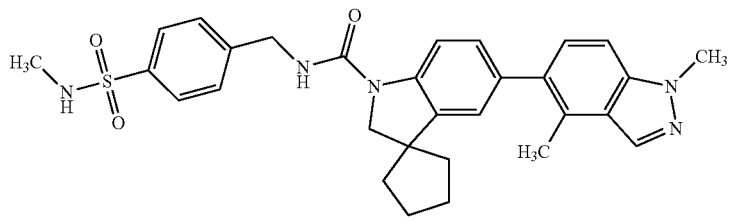 |
| 41 | 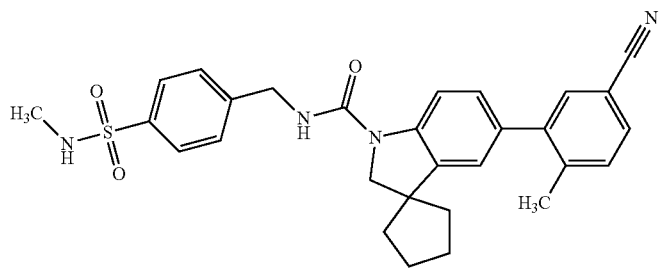 [SMILES: CNS(=O)(=O)c1ccc(CNC(=O)N2CC3(CCCC3)c3cc(-c4cc(C#N)ccc4C)ccc32)cc1] |

| Example | Structure |
|---|---|
| 42 | 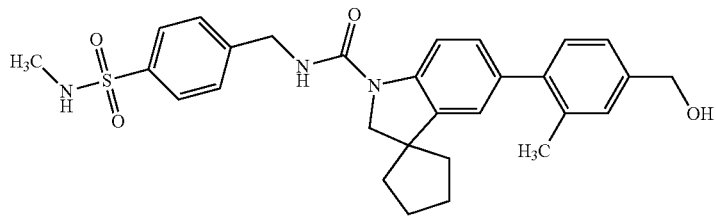 |
| 43 | 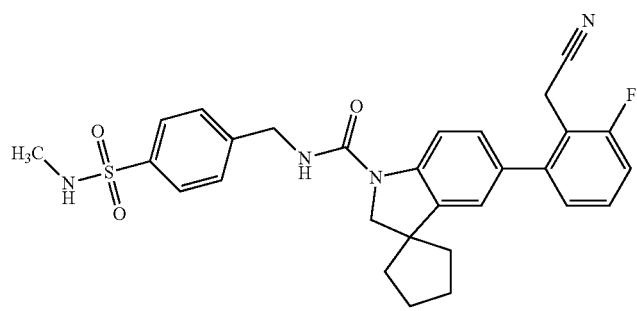 [SMILES: CNS(=O)(=O)c1ccc(CNC(=O)N2CC3(CCCC3)c3cc(-c4cccc(F)c4CC#N)ccc32)cc1] |
| 44 | 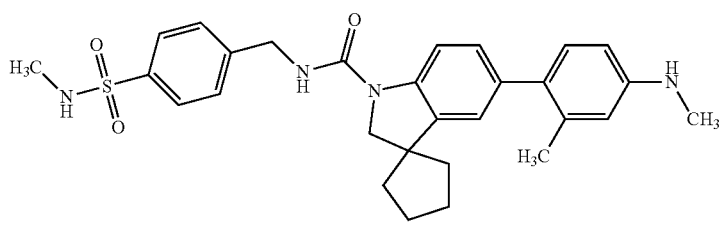 |
| 45 | 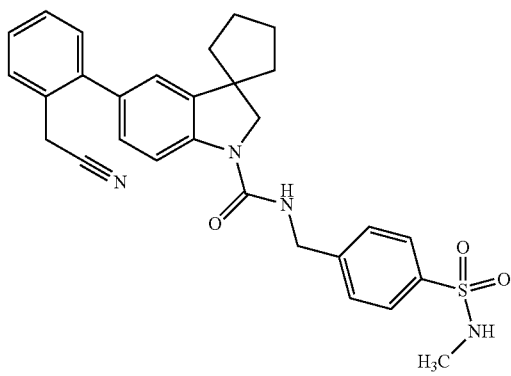 [SMILES: CNS(=O)(=O)c1ccc(CNC(=O)N2CC3(CCCC3)c3cc(-c4ccccc4CC#N)ccc32)cc1] |
| 46 | 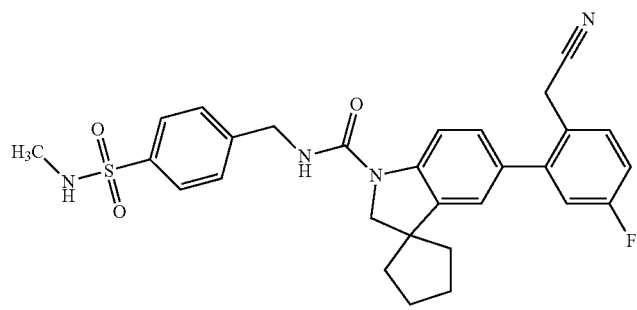 [SMILES: CNS(=O)(=O)c1ccc(CNC(=O)N2CC3(CCCC3)c3cc(-c4cc(F)ccc4CC#N)ccc32)cc1] |

-continued
| Example | Structure |
|---|---|
| 47 | 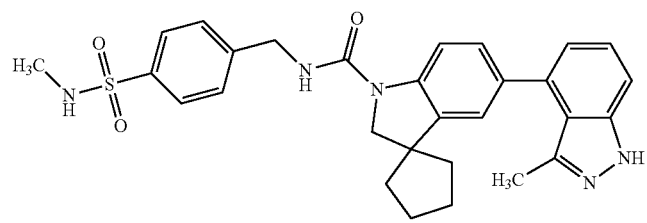 [SMILES: CNS(=O)(=O)c1ccc(CNC(=O)N2CC3(CCCC3)c3cc(-c4cccc5[nH]nc(C)c45)ccc32)cc1] |
| 48 | 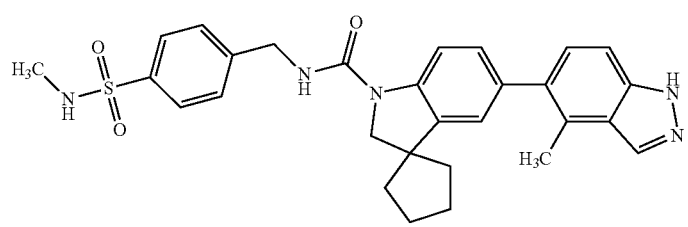 [SMILES: CNS(=O)(=O)c1ccc(CNC(=O)N2CC3(CCCC3)c3cc(-c4ccc5[nH]ncc5c4C)ccc32)cc1] |
| 49 | 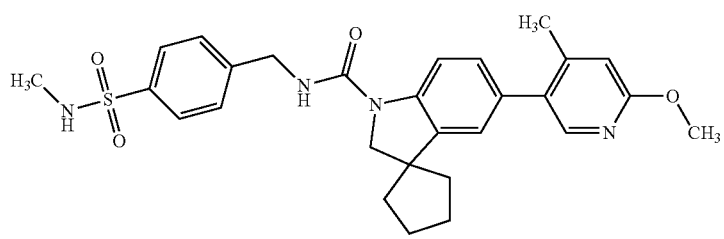 |
| 50 | 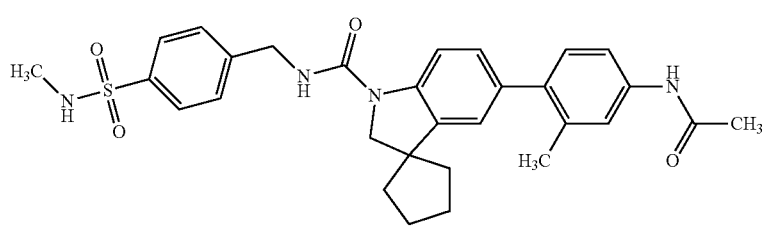 [SMILES: CNS(=O)(=O)c1ccc(CNC(=O)N2CC3(CCCC3)c3cc(-c4ccc(NC(C)=O)cc4C)ccc32)cc1] |
| 51 | 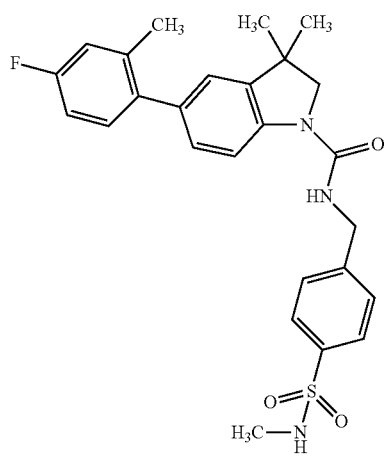 [SMILES: CNS(=O)(=O)c1ccc(CNC(=O)N2CC(C)(C)c3cc(-c4ccc(F)cc4C)ccc32)cc1] |

-continued
| Example | Structure |
|---|---|
| 52 | 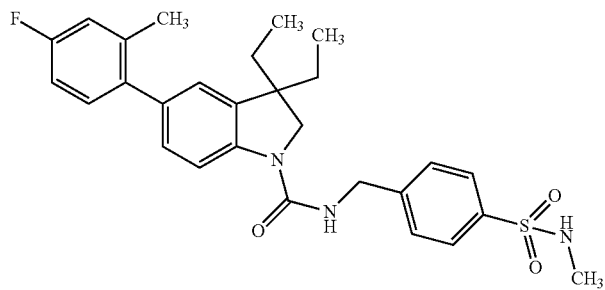 [SMILES: CCC1(CC)CN(C(=O)NCc2ccc(S(=O)(=O)NC)cc2)c2ccc(-c3ccc(F)cc3C)cc21] |
| 53 | 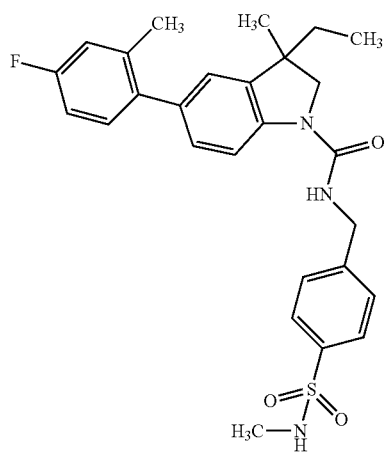 [SMILES: CCC1(C)CN(C(=O)NCc2ccc(S(=O)(=O)NC)cc2)c2ccc(-c3ccc(F)cc3C)cc21] |
| 54 | 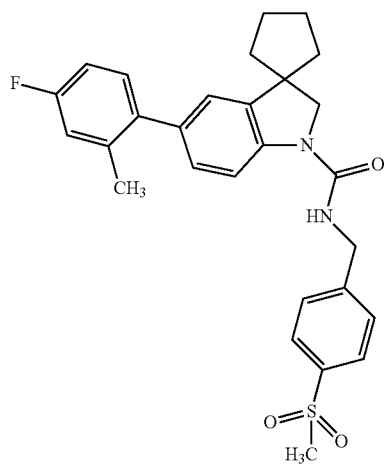 [SMILES: Cc1cc(F)ccc1-c1ccc2c(c1)C1(CCCC1)CN2C(=O)NCc1ccc(S(C)(=O)=O)cc1] |
| 55 | 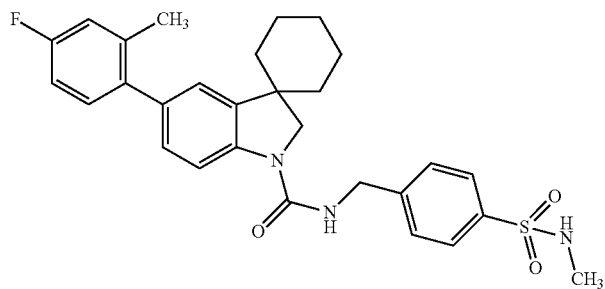 |

-continued
| Example | Structure |
|---|---|
| 56 | 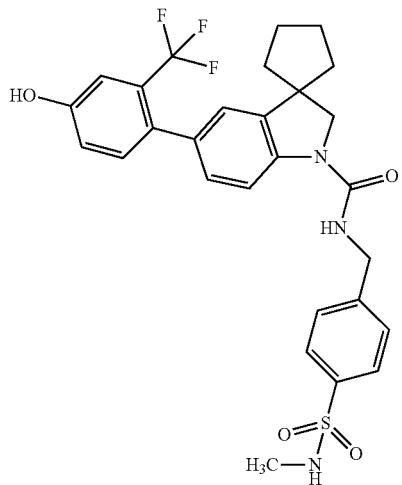 [SMILES: CNS(=O)(=O)c1ccc(CNC(=O)N2CC3(CCCC3)c3cc(-c4ccc(O)cc4C(F)(F)F)ccc32)cc1] |
| 57 | 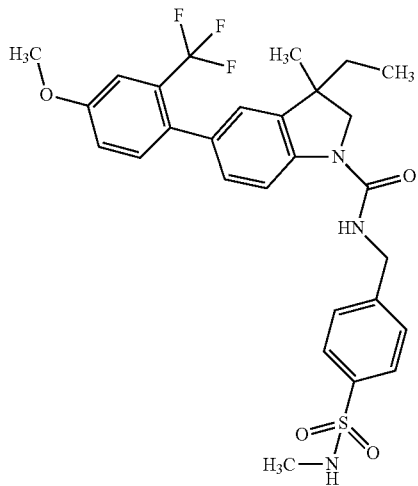 [SMILES: CCC1(C)CN(C(=O)NCc2ccc(S(=O)(=O)NC)cc2)c2ccc(-c3ccc(OC)cc3C(F)(F)F)cc21] |
| 58 | 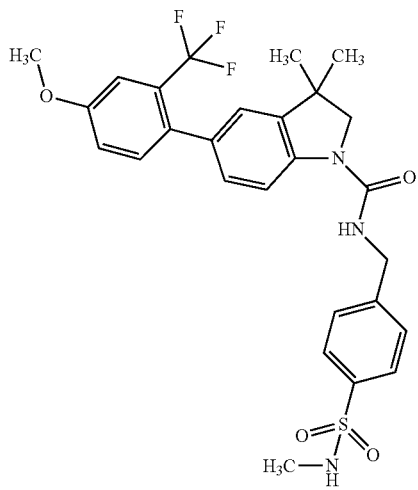 [SMILES: CNS(=O)(=O)c1ccc(CNC(=O)N2CC(C)(C)c3cc(-c4ccc(OC)cc4C(F)(F)F)ccc32)cc1] |

-continued
| Example | Structure |
|---|---|
| 59 | 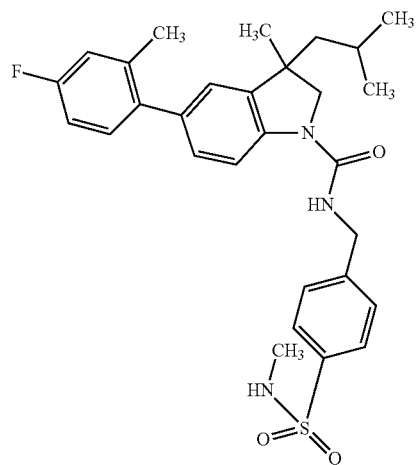 [SMILES: CNS(=O)(=O)c1ccc(CNC(=O)N2CC(C)(CC(C)C)c3cc(-c4ccc(F)cc4C)ccc32)cc1] |
| 60 | 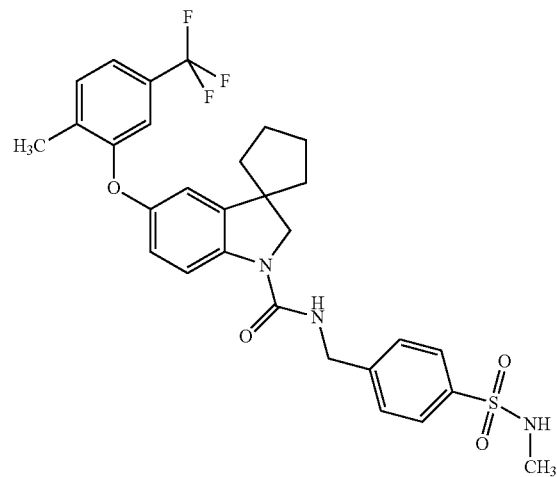 |
| 61 | 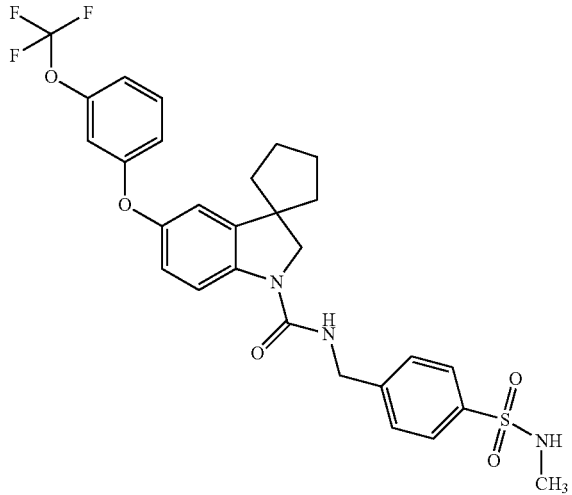 [SMILES: CNS(=O)(=O)c1ccc(CNC(=O)N2CC3(CCCC3)c3cc(Oc4cccc(OC(F)(F)F)c4)ccc32)cc1] |

-continued
| Example | Structure |
|---|---|
| 62 | 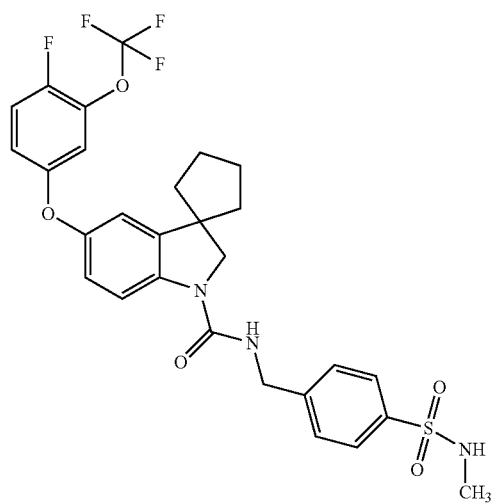 [SMILES: CNS(=O)(=O)c1ccc(CNC(=O)N2CC3(CCCC3)c3cc(Oc4ccc(F)c(OC(F)(F)F)c4)ccc32)cc1] |
| 63 | 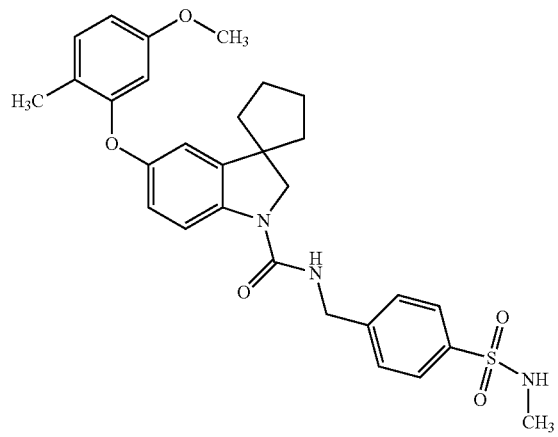 |
| 64 | 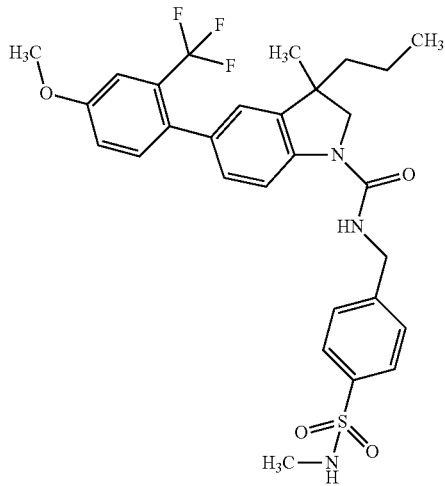 [SMILES: CCCC1(C)CN(C(=O)NCc2ccc(S(=O)(=O)NC)cc2)c2ccc(-c3ccc(OC)cc3C(F)(F)F)cc21] |

| Example | Structure |
|---|---|
| 65 | 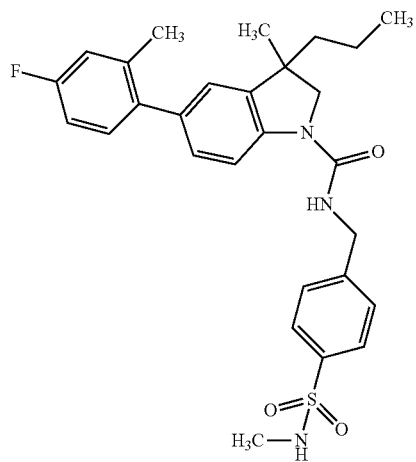 [SMILES: CCCC1(C)CN(C(=O)NCc2ccc(S(=O)(=O)NC)cc2)c2ccc(-c3ccc(F)cc3C)cc21] |
| 66 | 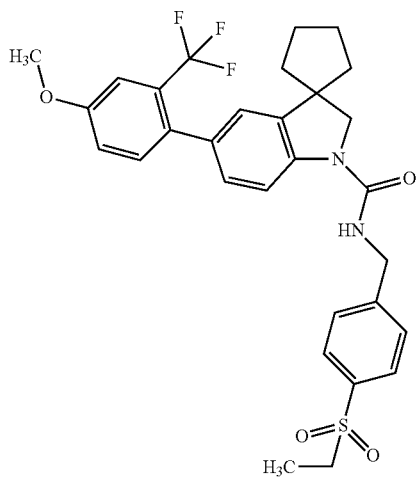 [SMILES: CCS(=O)(=O)c1ccc(CNC(=O)N2CC3(CCCC3)c3cc(-c4ccc(OC)cc4C(F)(F)F)ccc32)cc1] |
| 67 | 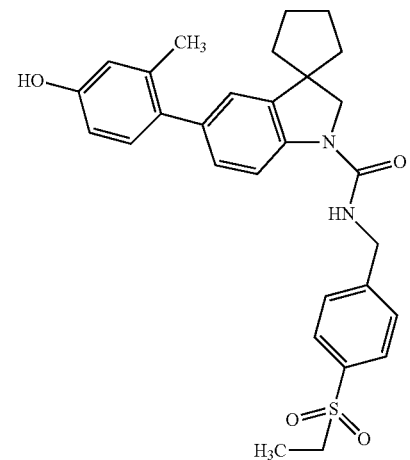 [SMILES: CCS(=O)(=O)c1ccc(CNC(=O)N2CC3(CCCC3)c3cc(-c4ccc(O)cc4C)ccc32)cc1] |

| Example | Structure |
|---|---|
| 68 | 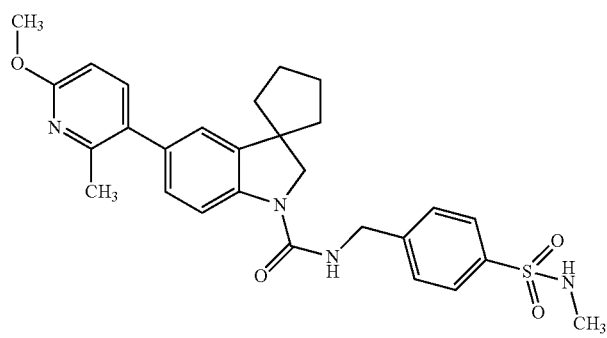 [SMILES: CNS(=O)(=O)c1ccc(CNC(=O)N2CC3(CCCC3)c3cc(-c4ccc(OC)nc4C)ccc32)cc1] |
| 69 | 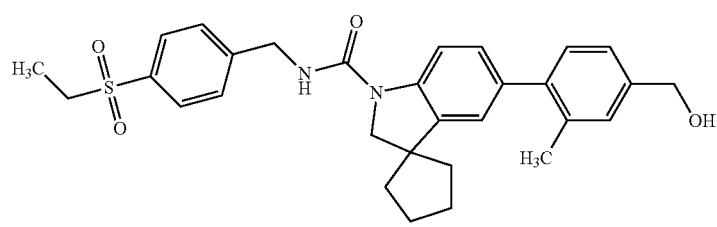 [SMILES: CCS(=O)(=O)c1ccc(CNC(=O)N2CC3(CCCC3)c3cc(-c4ccc(CO)cc4C)ccc32)cc1] |
| 70 | 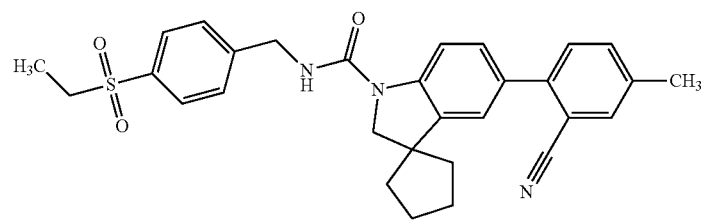 [SMILES: CCS(=O)(=O)c1ccc(CNC(=O)N2CC3(CCCC3)c3cc(-c4ccc(C)cc4C#N)ccc32)cc1] |
| 71 | 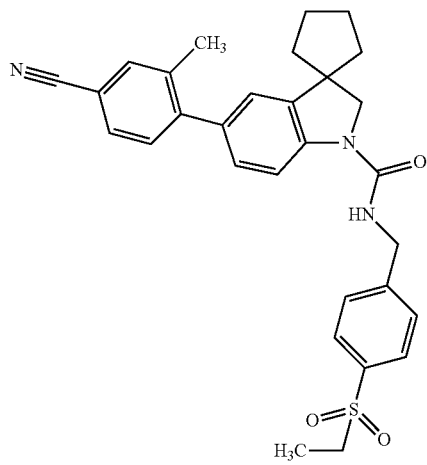 [SMILES: CCS(=O)(=O)c1ccc(CNC(=O)N2CC3(CCCC3)c3cc(-c4ccc(C#N)cc4C)ccc32)cc1] |
| 72 | 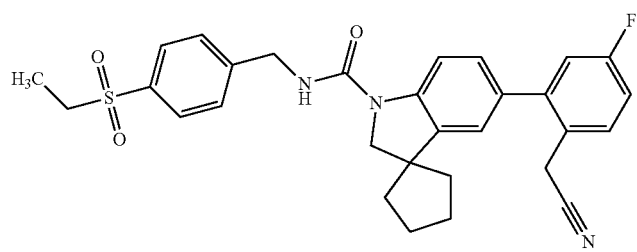 [SMILES: CCS(=O)(=O)c1ccc(CNC(=O)N2CC3(CCCC3)c3cc(-c4cc(F)ccc4CC#N)ccc32)cc1] |

-continued
| Example | Structure |
|---|---|
| 73 | 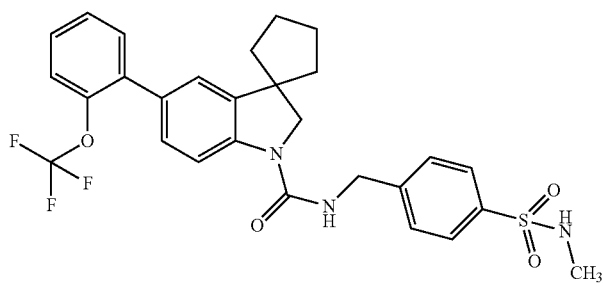 |
| 74 | 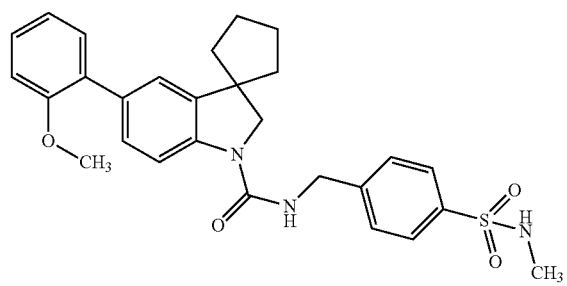 [SMILES: CNS(=O)(=O)c1ccc(CNC(=O)N2CC3(CCCC3)c3cc(-c4ccccc4OC)ccc32)cc1] |
| 75 | 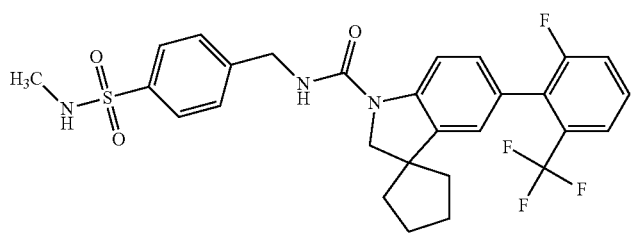 [SMILES: CNS(=O)(=O)c1ccc(CNC(=O)N2CC3(CCCC3)c3cc(-c4c(F)cccc4C(F)(F)F)ccc32)cc1] |
| 76 | 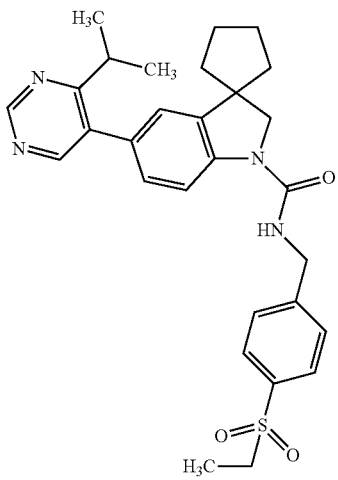 [SMILES: CCS(=O)(=O)c1ccc(CNC(=O)N2CC3(CCCC3)c3cc(-c4cncnc4C(C)C)ccc32)cc1] |
| 77 | 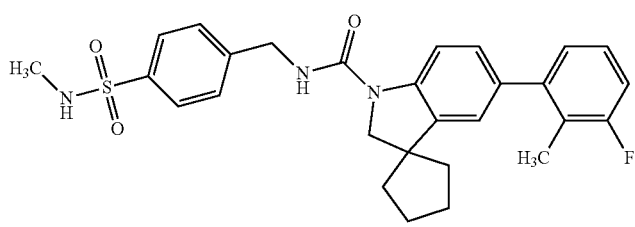 [SMILES: CNS(=O)(=O)c1ccc(CNC(=O)N2CC3(CCCC3)c3cc(-c4cccc(F)c4C)ccc32)cc1] |

-continued
| Example | Structure |
|---|---|
| 78 | 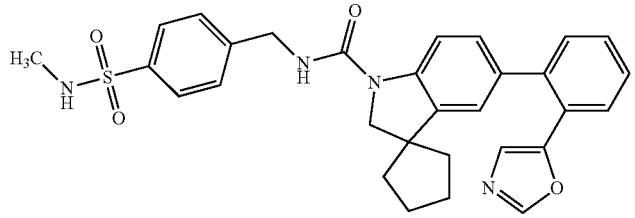 [SMILES: CNS(=O)(=O)c1ccc(CNC(=O)N2CC3(CCCC3)c3cc(-c4ccccc4-c4cnco4)ccc32)cc1] |
| 79 | 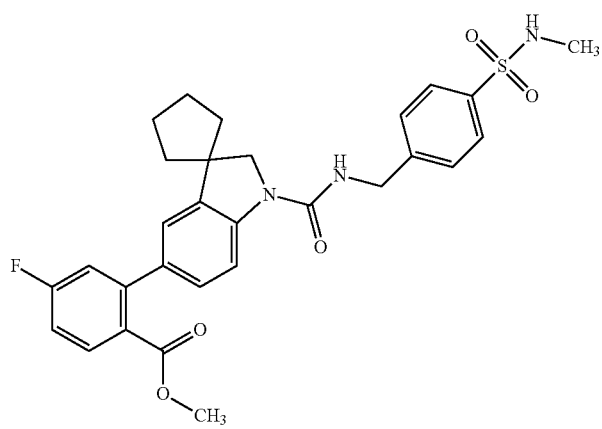 [SMILES: CNS(=O)(=O)c1ccc(CNC(=O)N2CC3(CCCC3)c3cc(-c4cc(F)ccc4C(=O)OC)ccc32)cc1] |
| 80 | 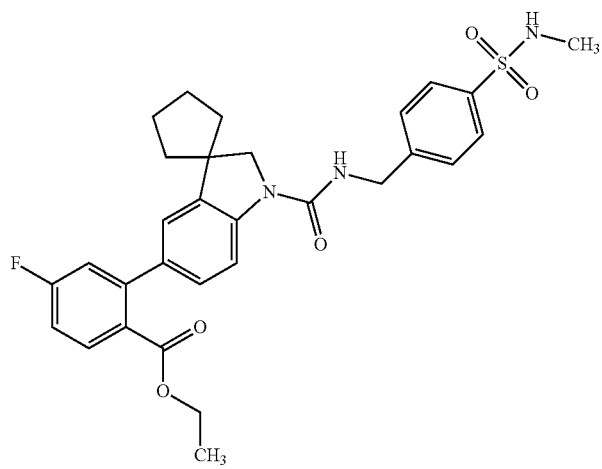 [SMILES: CCOC(=O)c1ccc(F)cc1-c1ccc2c(c1)C1(CCCC1)CN2C(=O)NCc1ccc(S(=O)(=O)NC)cc1] |
| 81 | 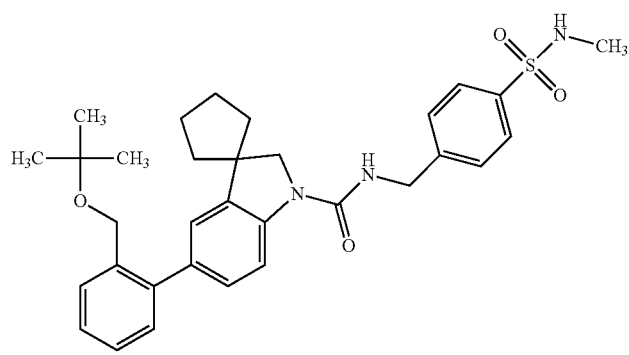 [SMILES: CNS(=O)(=O)c1ccc(CNC(=O)N2CC3(CCCC3)c3cc(-c4ccccc4COC(C)(C)C)ccc32)cc1] |

| Example | Structure |
|---|---|
| 82 | 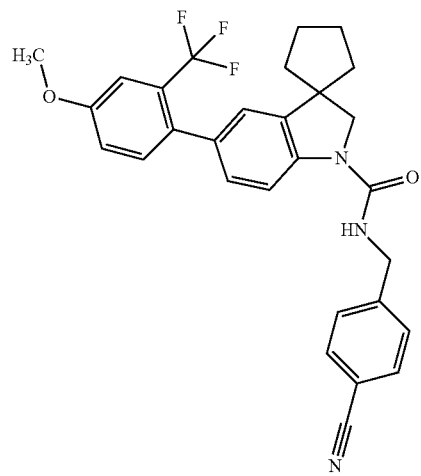 [SMILES: COc1ccc(-c2ccc3c(c2)C2(CCCC2)CN3C(=O)NCc2ccc(C#N)cc2)c(C(F)(F)F)c1] |
| 83 | 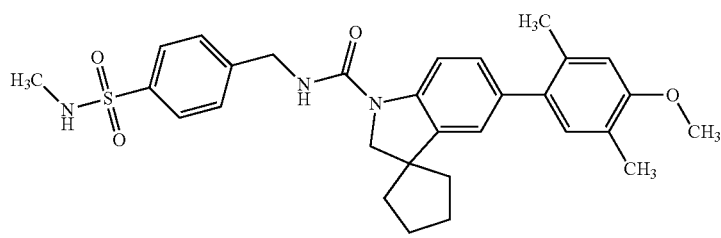 |
| 84 | 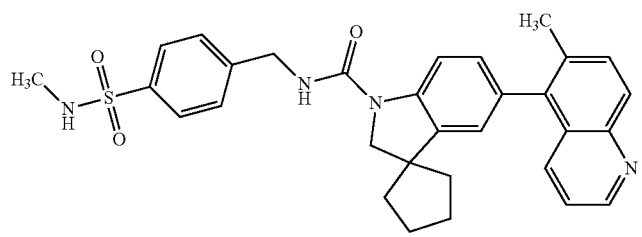 [SMILES: CNS(=O)(=O)c1ccc(CNC(=O)N2CC3(CCCC3)c3cc(-c4c(C)ccc5ncccc45)ccc32)cc1] |
| 85 | 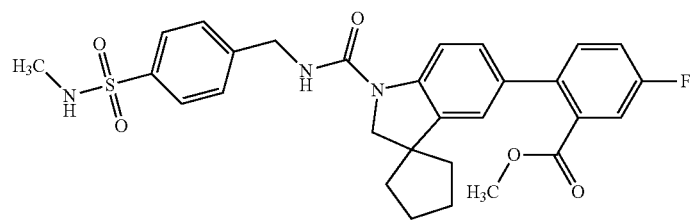 [SMILES: CNS(=O)(=O)c1ccc(CNC(=O)N2CC3(CCCC3)c3cc(-c4ccc(F)cc4C(=O)OC)ccc32)cc1] |
| 86 | 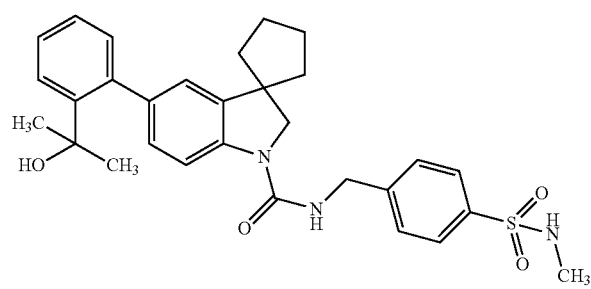 [SMILES: CNS(=O)(=O)c1ccc(CNC(=O)N2CC3(CCCC3)c3cc(-c4ccccc4C(C)(C)O)ccc32)cc1] |

-continued
| Example | Structure |
|---|---|
| 87 | 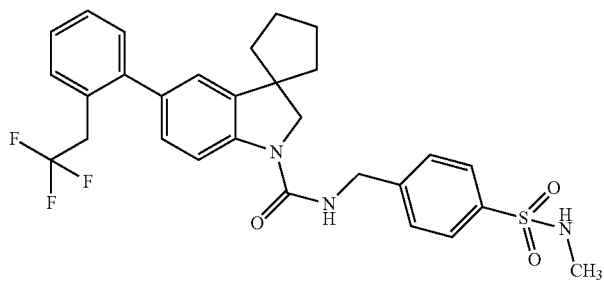 [SMILES: CNS(=O)(=O)c1ccc(CNC(=O)N2CC3(CCCC3)c3cc(-c4ccccc4CC(F)(F)F)ccc32)cc1] |
| 88 | 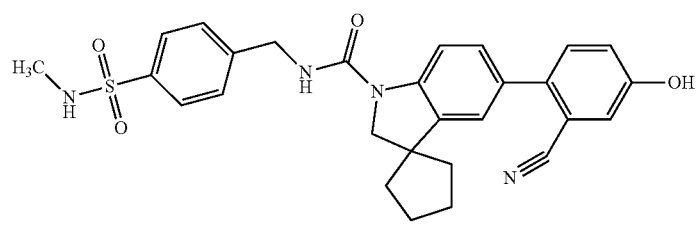 [SMILES: CNS(=O)(=O)c1ccc(CNC(=O)N2CC3(CCCC3)c3cc(-c4ccc(O)cc4C#N)ccc32)cc1] |
| 89 | 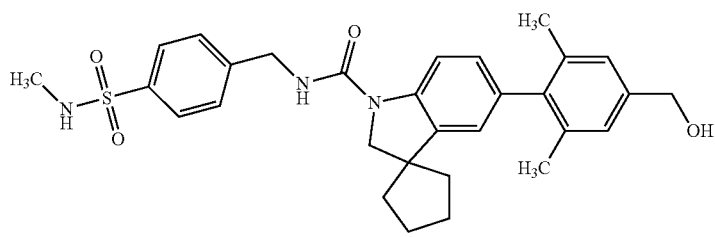 [SMILES: CNS(=O)(=O)c1ccc(CNC(=O)N2CC3(CCCC3)c3cc(-c4c(C)cc(CO)cc4C)ccc32)cc1] |
| 90 | 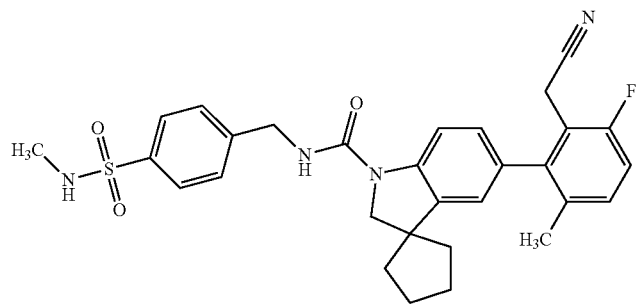 [SMILES: CNS(=O)(=O)c1ccc(CNC(=O)N2CC3(CCCC3)c3cc(-c4c(C)ccc(F)c4CC#N)ccc32)cc1] |
| 91 | 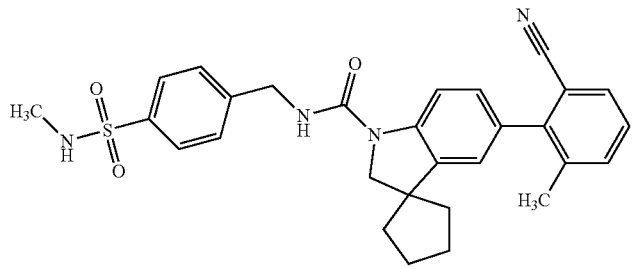 |
| 92 | 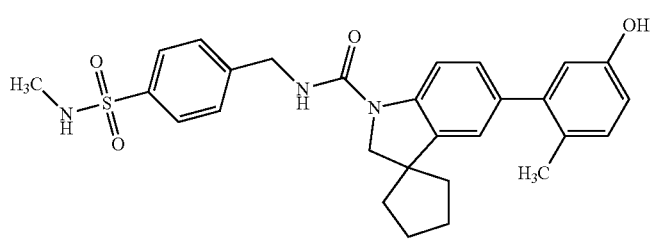 [SMILES: CNS(=O)(=O)c1ccc(CNC(=O)N2CC3(CCCC3)c3cc(-c4cc(O)ccc4C)ccc32)cc1] |

-continued
| Example | Structure |
|---|---|
| 93 | 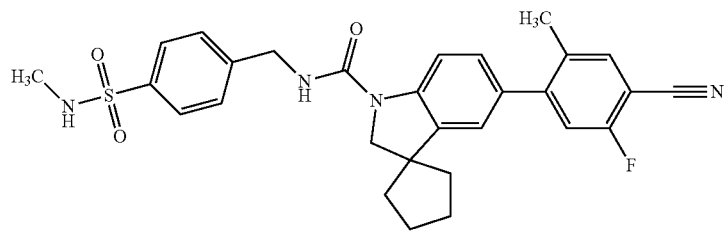 [SMILES: CNS(=O)(=O)c1ccc(CNC(=O)N2CC3(CCCC3)c3cc(-c4cc(F)c(C#N)cc4C)ccc32)cc1] |
| 94 | 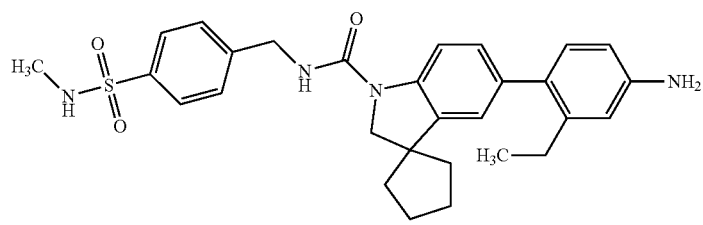 |
| 95 | 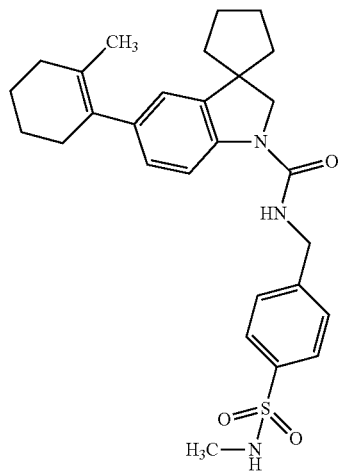 [SMILES: CNS(=O)(=O)c1ccc(CNC(=O)N2CC3(CCCC3)c3cc(C4=C(C)CCCC4)ccc32)cc1] |
| 96 | 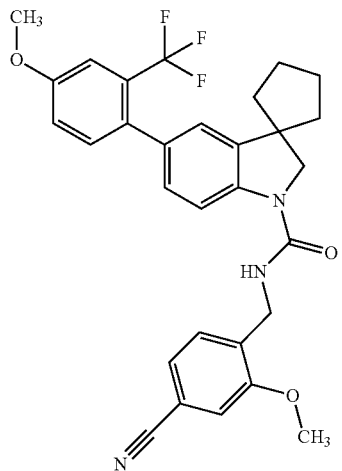 [SMILES: COc1ccc(-c2ccc3c(c2)C2(CCCC2)CN3C(=O)NCc2ccc(C#N)cc2OC)c(C(F)(F)F)c1] |

| Example | Structure |
|---|---|
| 97 | 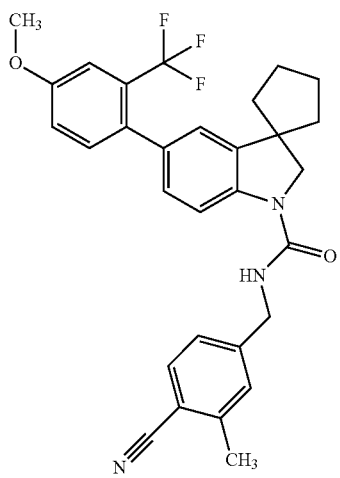 [SMILES: COc1ccc(-c2ccc3c(c2)C2(CCCC2)CN3C(=O)NCc2ccc(C#N)c(C)c2)c(C(F)(F)F)c1] |
| 98 | 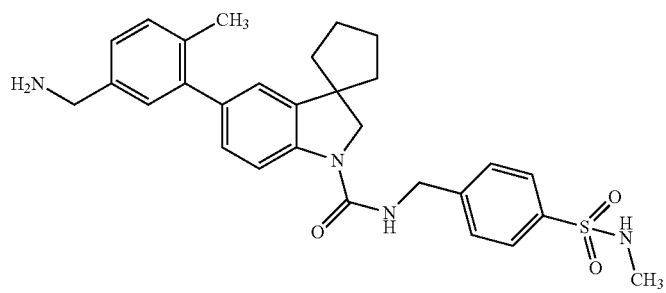 [SMILES: CNS(=O)(=O)c1ccc(CNC(=O)N2CC3(CCCC3)c3cc(-c4cc(CN)ccc4C)ccc32)cc1] |
| 99 | 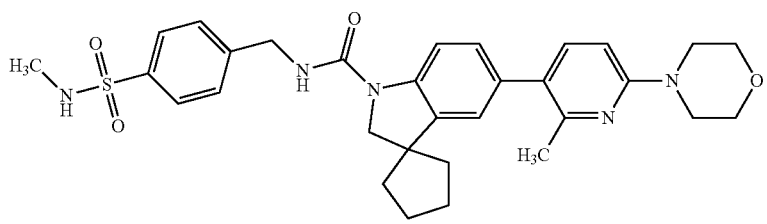 [SMILES: CNS(=O)(=O)c1ccc(CNC(=O)N2CC3(CCCC3)c3cc(-c4ccc(N5CCOCC5)nc4C)ccc32)cc1] |
| 100 | 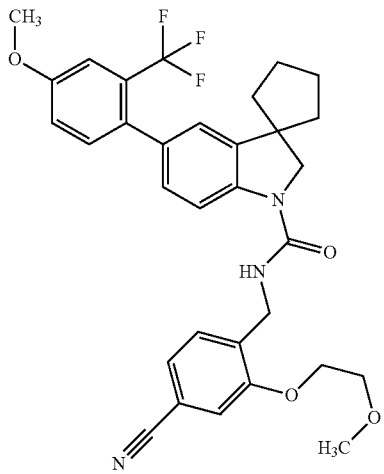 [SMILES: COCCOc1cc(C#N)ccc1CNC(=O)N1CC2(CCCC2)c2cc(-c3ccc(OC)cc3C(F)(F)F)ccc21] |

-continued
| Example | Structure |
|---------|-----------|
| 101 | 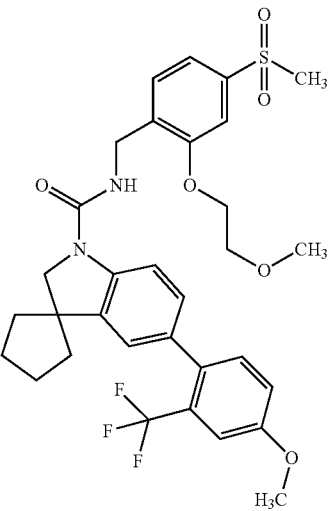 [SMILES: COCCOc1cc(S(C)(=O)=O)ccc1CNC(=O)N1CC2(CCCC2)c2cc(-c3ccc(OC)cc3C(F)(F)F)ccc21] |
| 102 | 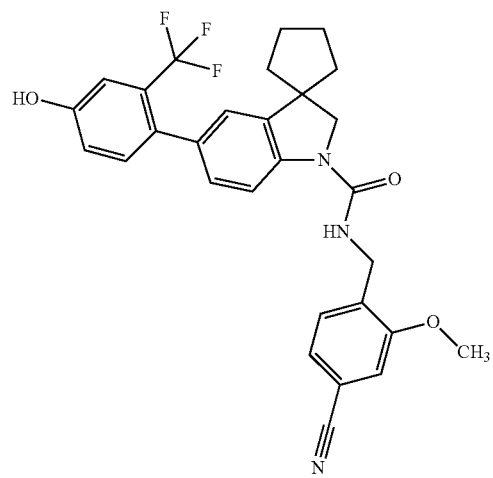 [SMILES: COc1cc(C#N)ccc1CNC(=O)N1CC2(CCCC2)c2cc(-c3ccc(O)cc3C(F)(F)F)ccc21] |
| 103 | 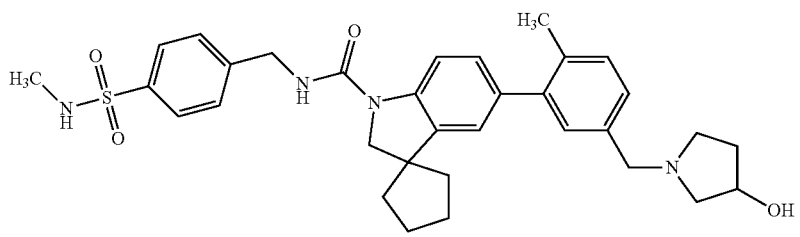 [SMILES: CNS(=O)(=O)c1ccc(CNC(=O)N2CC3(CCCC3)c3cc(-c4cc(CN5CCC(O)C5)ccc4C)ccc32)cc1] |

| Example | Structure |
|---|---|
| 104 | 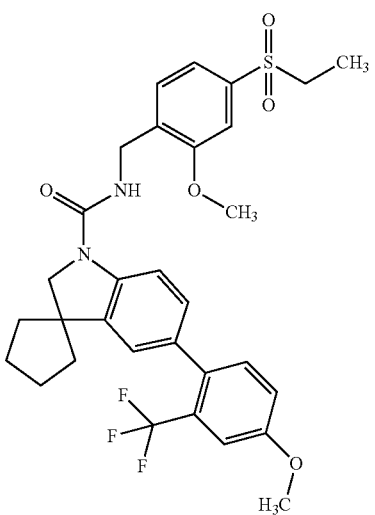 [SMILES: CCS(=O)(=O)c1ccc(CNC(=O)N2CC3(CCCC3)c3cc(-c4ccc(OC)cc4C(F)(F)F)ccc32)c(OC)c1] |
| 105 | 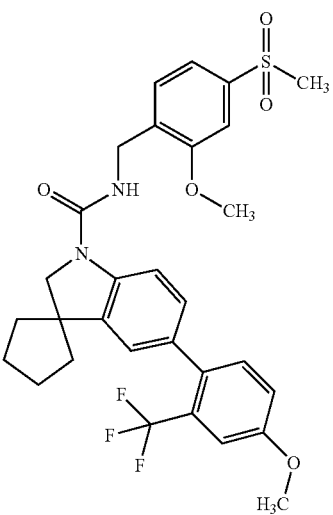 [SMILES: COc1ccc(-c2ccc3c(c2)C2(CCCC2)CN3C(=O)NCc2ccc(S(C)(=O)=O)cc2OC)c(C(F)(F)F)c1] |
| 106 | 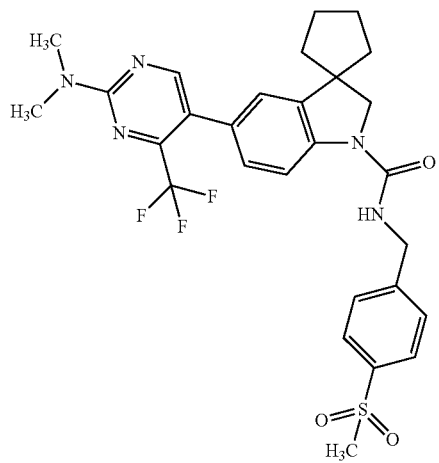 [SMILES: CN(C)c1ncc(-c2ccc3c(c2)C2(CCCC2)CN3C(=O)NCc2ccc(S(C)(=O)=O)cc2)c(C(F)(F)F)n1] |

| Example | Structure |
|---|---|
| 107 | 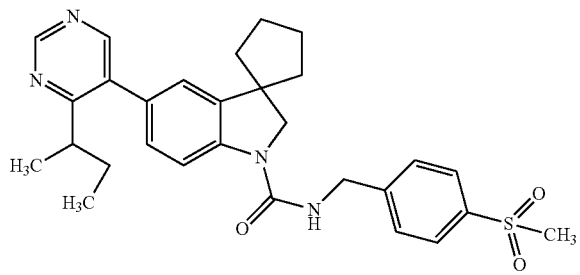 [SMILES: CCC(C)c1ncncc1-c1ccc2c(c1)C1(CCCC1)CN2C(=O)NCc1ccc(S(C)(=O)=O)cc1] |
| 108 | 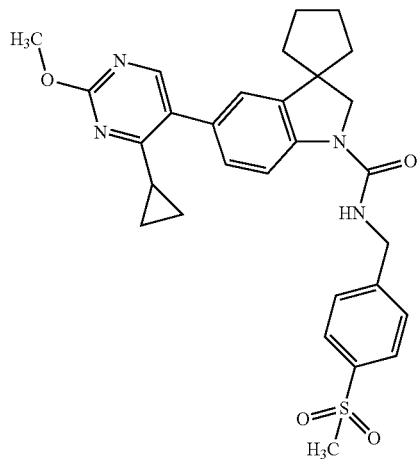 [SMILES: COc1ncc(-c2ccc3c(c2)C2(CCCC2)CN3C(=O)NCc2ccc(S(C)(=O)=O)cc2)c(C2CC2)n1] |
| 109 | 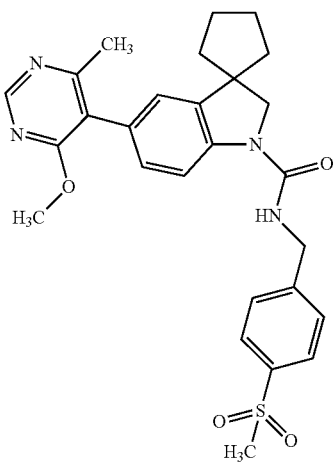 [SMILES: COc1ncnc(C)c1-c1ccc2c(c1)C1(CCCC1)CN2C(=O)NCc1ccc(S(C)(=O)=O)cc1] |

| Example | Structure |
|---|---|
| 110 | 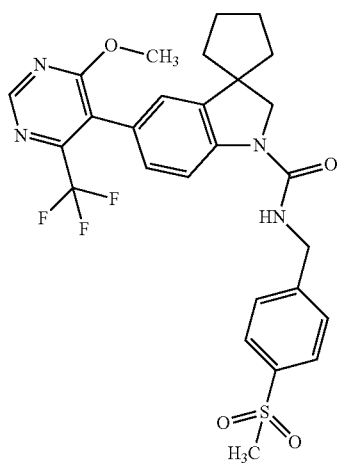 [SMILES: COc1ncnc(C(F)(F)F)c1-c1ccc2c(c1)C1(CCCC1)CN2C(=O)NCc1ccc(S(C)(=O)=O)cc1] |
| 111 | 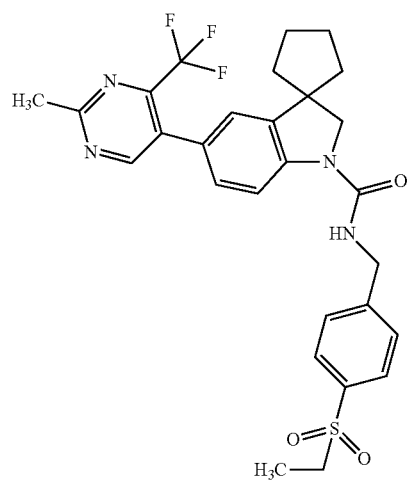 [SMILES: CCS(=O)(=O)c1ccc(CNC(=O)N2CC3(CCCC3)c3cc(-c4cnc(C)nc4C(F)(F)F)ccc32)cc1] |
| 112 | 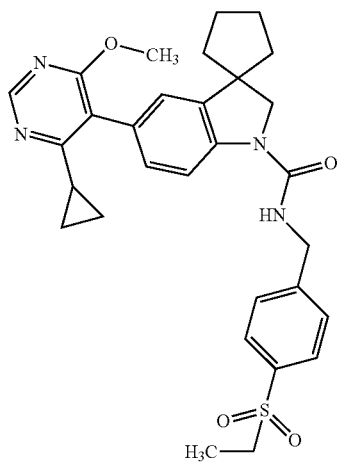 [SMILES: CCS(=O)(=O)c1ccc(CNC(=O)N2CC3(CCCC3)c3cc(-c4c(OC)ncnc4C4CC4)ccc32)cc1] |

-continued
| Example | Structure |
|---|---|
| 113 | 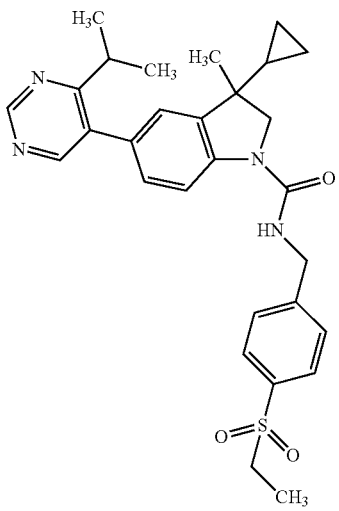 [SMILES: CCS(=O)(=O)c1ccc(CNC(=O)N2CC(C)(C3CC3)c3cc(-c4cncnc4C(C)C)ccc32)cc1] |
| 114 | 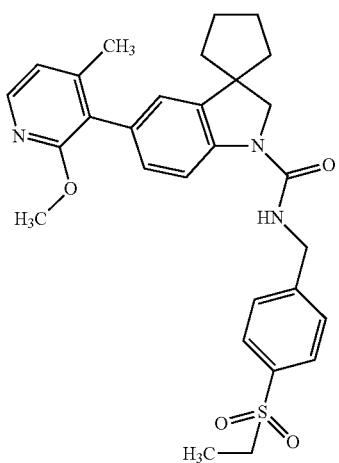 [SMILES: CCS(=O)(=O)c1ccc(CNC(=O)N2CC3(CCCC3)c3cc(-c4c(C)ccnc4OC)ccc32)cc1] |
| 115 | 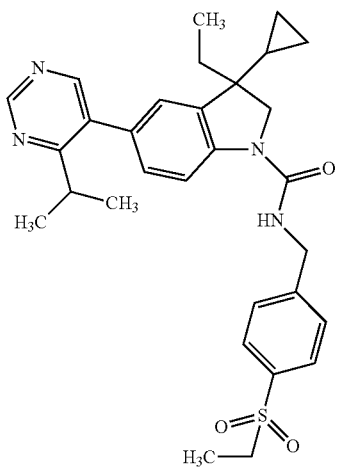 [SMILES: CCC1(C2CC2)CN(C(=O)NCc2ccc(S(=O)(=O)CC)cc2)c2ccc(-c3cncnc3C(C)C)cc21] |

| Example | Structure |
|---|---|
| 116 | 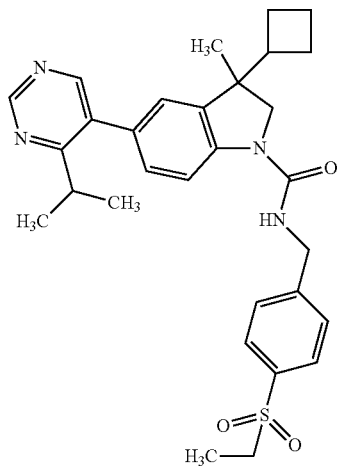 [SMILES: CCS(=O)(=O)c1ccc(CNC(=O)N2CC(C)(C3CCC3)c3cc(-c4cncnc4C(C)C)ccc32)cc1] |
| 117 | 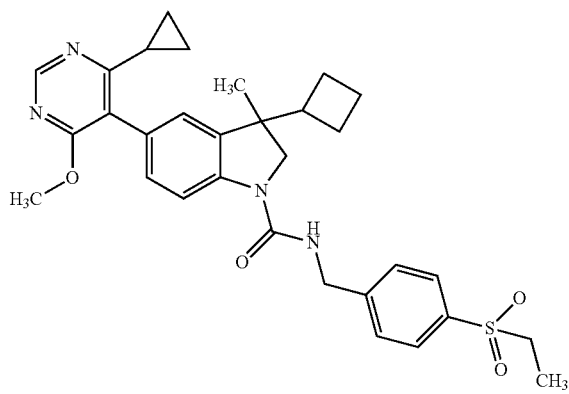 |
| 118 | 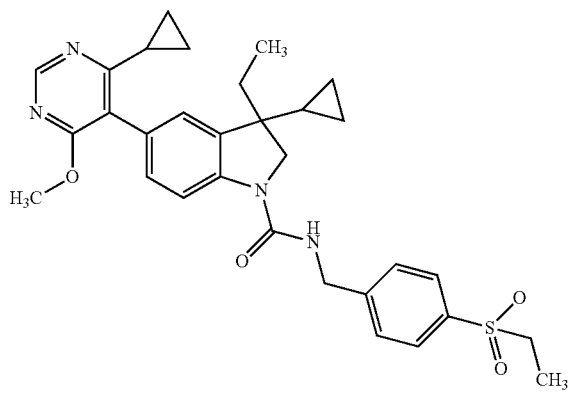 |

-continued
| Example | Structure |
|---|---|
| 119 | 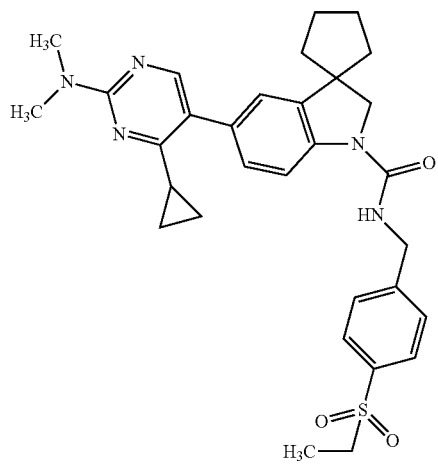 [SMILES: CCS(=O)(=O)c1ccc(CNC(=O)N2CC3(CCCC3)c3cc(-c4cnc(N(C)C)nc4C4CC4)ccc32)cc1] |
| 120 | 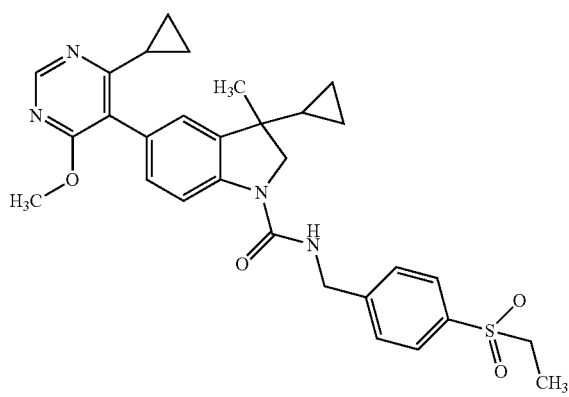 |
| 121 | 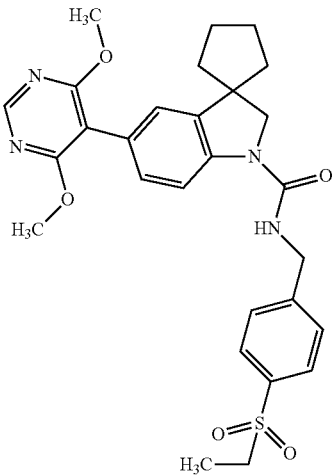 [SMILES: CCS(=O)(=O)c1ccc(CNC(=O)N2CC3(CCCC3)c3cc(-c4c(OC)ncnc4OC)ccc32)cc1] |

-continued
| Example | Structure |
|---|---|
| 122 | 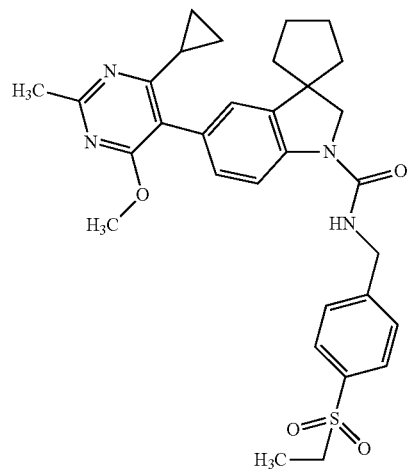 [SMILES: CCS(=O)(=O)c1ccc(CNC(=O)N2CC3(CCCC3)c3cc(-c4c(OC)nc(C)nc4C4CC4)ccc32)cc1] |
| 123 | 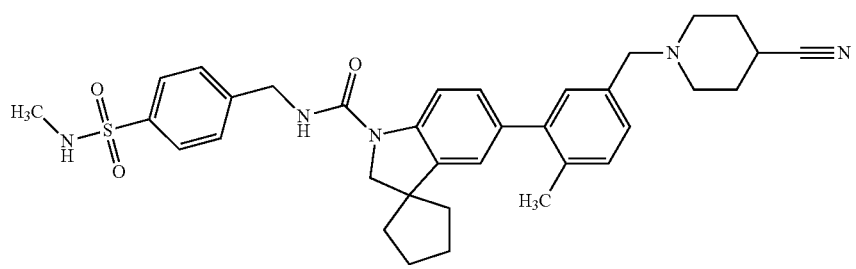 [SMILES: CNS(=O)(=O)c1ccc(CNC(=O)N2CC3(CCCC3)c3cc(-c4cc(CN5CCC(C#N)CC5)ccc4C)ccc32)cc1] |
| 124 | 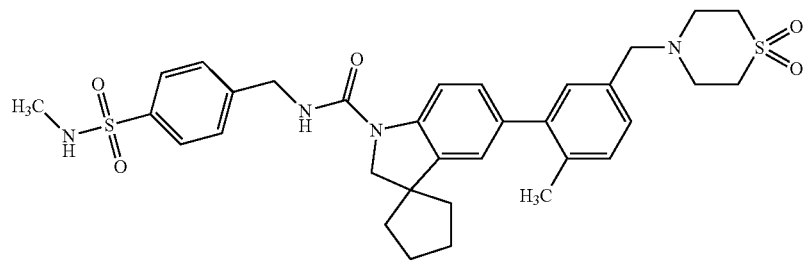 [SMILES: CNS(=O)(=O)c1ccc(CNC(=O)N2CC3(CCCC3)c3cc(-c4cc(CN5CCS(=O)(=O)CC5)ccc4C)ccc32)cc1] |
| 125 | 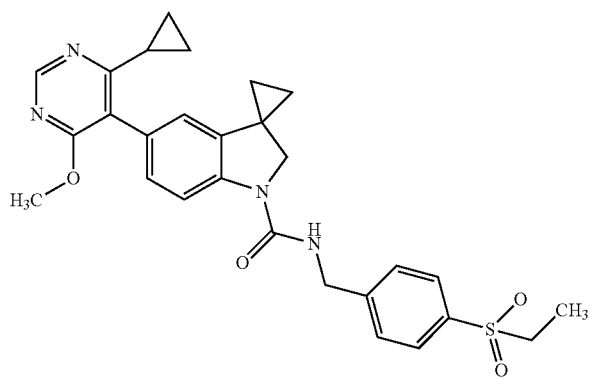 |

| Example | Structure | |
|---|---|---|
| 126 | 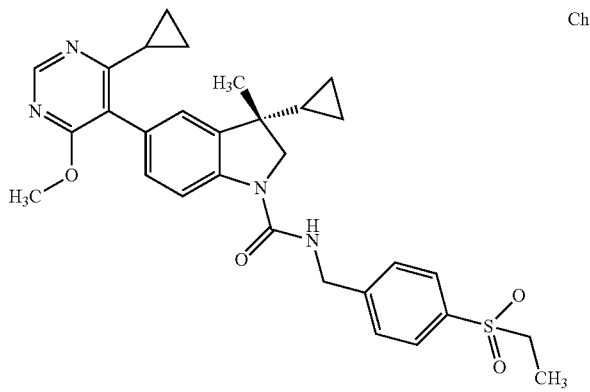 | Chiral |
| 127 | 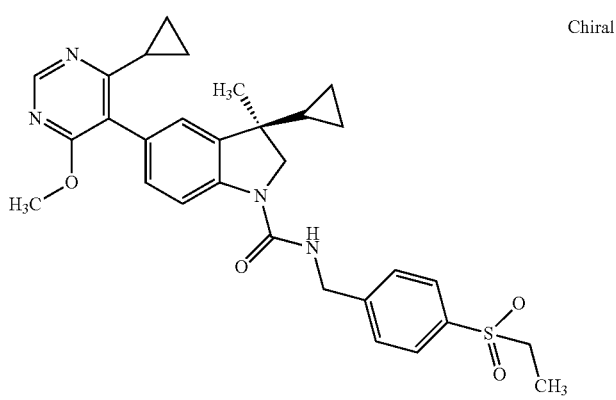 | Chiral |
| 128 | 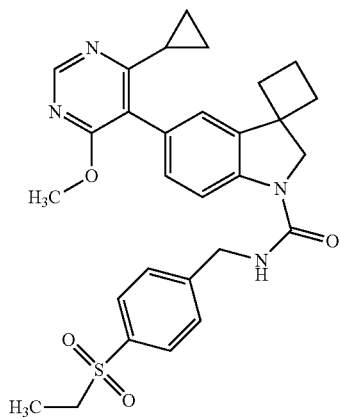 [SMILES: CCS(=O)(=O)c1ccc(CNC(=O)N2CC3(CCC3)c3cc(-c4c(OC)ncnc4C4CC4)ccc32)cc1] | |

| Example | Structure |
|---|---|
| 129 | 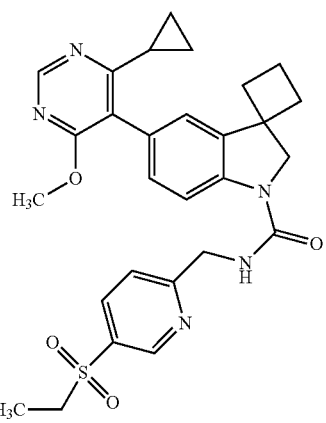 |
| 130 | 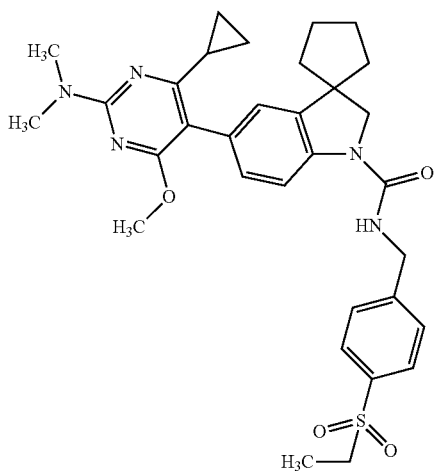 [SMILES: CCS(=O)(=O)c1ccc(CNC(=O)N2CC3(CCCC3)c3cc(-c4c(OC)nc(N(C)C)nc4C4CC4)ccc32)cc1] |
or a pharmaceutically acceptable salt thereof.
12. A pharmaceutical composition comprising a compound of formula (I) according to claim 1, or a pharmaceutically acceptable salt thereof, and at least one pharmaceutically acceptable carrier.
* * * * *